(12) United States Patent
Heaven et al.

(10) Patent No.: US 11,083,448 B2
(45) Date of Patent: Aug. 10, 2021

(54) SYSTEM AND METHOD FOR ATTACHING SOFT TISSUE TO BONE

(71) Applicant: Conmed Corporation, Utica, NY (US)

(72) Inventors: Malcolm Heaven, Reno, NV (US); Mikxay Sirivong, Escondido, CA (US); Rudy Pretti, Auburn, CA (US); Michael Ko, Mission Viejo, CA (US); John P. Greelis, Carlsbad, CA (US)

(73) Assignee: Conmed Corporation, Utica, NY (US)

( * ) Notice: Subject to any disclaimer, the term of this patent is extended or adjusted under 35 U.S.C. 154(b) by 447 days.

(21) Appl. No.: 15/612,722

(22) Filed: Jun. 2, 2017

(65) Prior Publication Data

US 2017/0265854 A1 Sep. 21, 2017

Related U.S. Application Data

(62) Division of application No. 13/972,652, filed on Aug. 21, 2013, now Pat. No. 9,706,984, which is a division
(Continued)

(51) Int. Cl.
*A61B 17/04* (2006.01)

(52) U.S. Cl.
CPC .. *A61B 17/0401* (2013.01); *A61B 2017/0409* (2013.01); *A61B 2017/0424* (2013.01)

(58) Field of Classification Search
CPC ............ A61B 17/0401; A61B 17/0487; A61B 17/3468; A61B 17/70; A61B 2017/0409; A61B 2017/0411; A61B 2017/0414; A61B 2017/042; A61B 2017/0422; A61B 2017/0424; A61B 2017/0425; A61B 2017/0445; A61B 2017/0464;
(Continued)

(56) References Cited

U.S. PATENT DOCUMENTS

| | | | | |
|---|---|---|---|---|
| 5,268,001 A | * | 12/1993 | Nicholson | .......... A61B 17/0401 606/104 |
| 7,037,324 B2 | * | 5/2006 | Martinek | ........... A61B 17/0401 606/139 |

(Continued)

*Primary Examiner* — Todd J Scherbel
(74) *Attorney, Agent, or Firm* — Bond, Schoeneck & King, PLLC; Frederick J. M. Price

(57) ABSTRACT

Disclosed herein are methods and devices for securing soft tissue to a rigid material such as bone. A bone anchor is described that comprises an anchor body with expandable tines and a spreader that expands the tines into bone. Also disclosed is a bone anchor that comprises a base and a top such that suture material may be attached to apertures in the anchor top or else compressed between surfaces on the base and top to secure the suture to the anchor. Also described is an inserter that can be used to insert the bone anchor into bone and move the spreader relative to the anchor body attach suture material. Also described is an inserter that can be used to insert the bone anchor into bone and move the anchor top relative to the anchor body or anchor base to attach to or clamp suture material there between. Methods are described that allow use of single bone anchor to secure tissue to bone or also to use more than one bone anchor to provide multiple lengths of suture material to compress a large area of soft tissue against bone.

2 Claims, 57 Drawing Sheets

Related U.S. Application Data of application No. 12/697,138, filed on Jan. 29, 2010, now Pat. No. 8,523,902.

(60) Provisional application No. 61/148,805, filed on Jan. 30, 2009, provisional application No. 61/251,199, filed on Oct. 13, 2009.

(58) Field of Classification Search
CPC ........... A61B 2017/0496; A61F 2/0811; A61F 2002/0817; A61F 2002/0823; A61F 2002/0835; A61F 2002/0841
See application file for complete search history.

(56) References Cited

U.S. PATENT DOCUMENTS

| | | | | |
|---|---|---|---|---|
| 8,523,902 B2* | 9/2013 | Heaven | ............... | A61B 17/0401 606/232 |
| 9,706,984 B2* | 7/2017 | Heaven | ............... | A61B 17/0401 |
| 2006/0235413 A1* | 10/2006 | Denham | ............ | A61B 17/0401 606/232 |
| 2007/0142835 A1* | 6/2007 | Green | ................ | A61B 17/0401 606/327 |

* cited by examiner

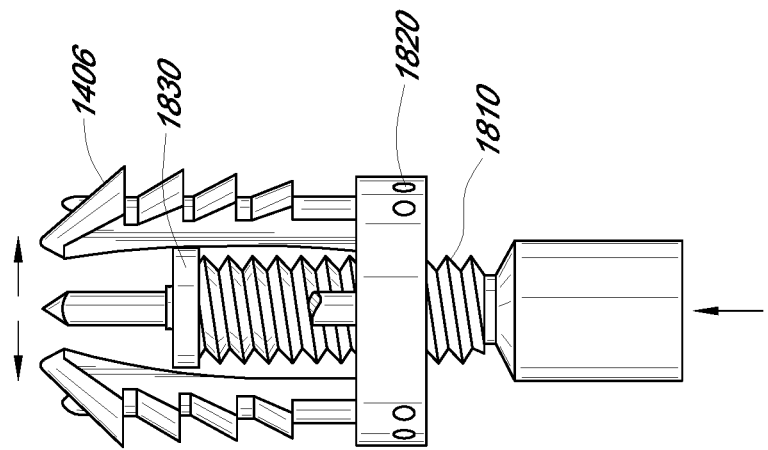
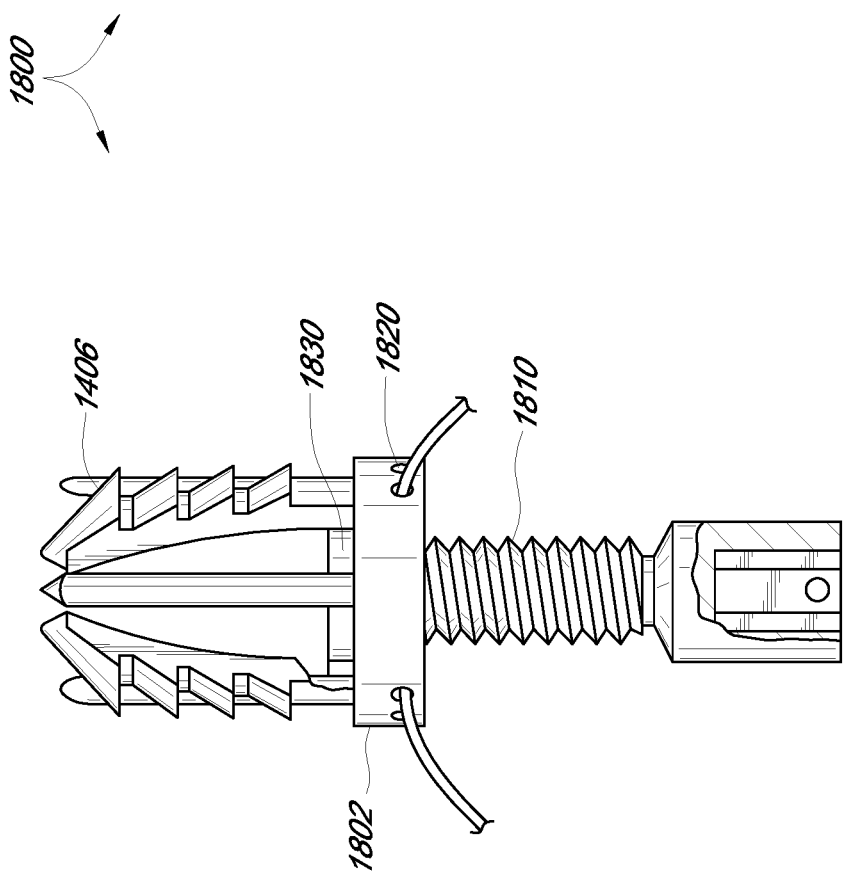

SYSTEM AND METHOD FOR ATTACHING SOFT TISSUE TO BONE

RELATED APPLICATIONS

This application is a divisional of U.S. application Ser. No. 13/972,652 filed Aug. 21, 2013, which is a divisional of U.S. application Ser. No. 12/697,138, now issued as U.S. Pat. No. 8,523,902 filed Jan. 29, 2010, which claims the benefit of U.S. Provisional Application Nos. 61/148,805, filed Jan. 30, 2009, and 61/251,199, filed Oct. 13, 2009, each of which is herein incorporated by reference in their respective entireties.

BACKGROUND

Field of the Invention

The present invention relates to medical devices. Some embodiments relate to a bone anchor for securing body tissue to bone.

Description of the Related Art

There are several medical procedures where a surgeon needs to attach soft tissue such as tendons or other soft connective tissue to bone. One common example is a torn rotator cuff, where the supraspinatus tendon has separated from the humerus causing pain and loss of ability to elevate and externally rotate the arm. To repair a torn rotator cuff, typically a surgical procedure is used to suture the torn tendon to the bone using a variety of methods. Some procedures utilize large incisions and involve complete detachment of the deltoid muscle from the acromion. Small diameter holes are made in the bone for passing suture material through the bone to secure the tendon. Such large incision procedures are traumatic, causing prolonged pain and recovery time. Other procedures make small incisions and use arthroscopic techniques to attach sutures using either small diameter holes or a bendable tine. Other injuries requiring similar techniques include biceps tendonitis (e.g., a biceps tenodesis procedure) and a torn ACL.

Currently, there are various staple and anchor devices for attaching soft tissue to bone. However, many of these devices suffer from low pull-out strength, a lack of adequate suture attachment sites, a requirement to tie complicated knots with the sutures, complicated threading routines, a failure to assist the surgeon in positioning soft tissue into contact with bone prior to suturing to maximize bonding of the soft tissue to bone, and an overall difficulty in physically handling the devices during surgery.

Generally, injury to joints such as the shoulder and knee involve the tearing or separation of ligaments from their natural position on the bone. The injury leads to a chronic instability in the joint which requires surgical intervention. Modernly, the surgery involves use of one or more arthroscopic devices. These devices include surgical cannulas through which a camera or surgical device are passed. The arthroscopic methods usually involve reduced trauma to the patient than previous methods and can predict a faster recovery.

In brief, the surgical procedures involve visualization and localization of the damage, preparation of the bone surface, implantation of a soft tissue anchor, and suturing of the tissue to the anchor. By tightly contacting the ligament or other soft tissue to a properly prepared bone surface, the two materials bond during the healing process.

However, it is difficult to manipulate sutures within the surgical site using arthroscopic techniques. In some techniques, such as knot tying, it is difficult to properly adjust the tension of the suture while tightening the knot. Thus, there is a need for improved methods and devices that allow easy arthroscopic repair of soft tissue injuries. It is understood that the methods and devices described herein are applicable to other surgical procedures, whether the surgery is arthroscopic or open.

SUMMARY

One embodiment disclosed herein includes an anchor for attaching tissue to bone that includes an anchor body comprising an axial bore, a plurality of bone-engaging tines extending distally from the anchor body, a spreader comprising an axial bore, and a suture loop extending through the axial bore, wherein the suture loop is secured against being pulled through the axial bore, the spreader is configured to be positioned between the bone-engaging tines, and the spreader is configured to expand the tines outward upon distal or proximal movement of the spreader relative to the anchor body.

Another embodiment disclosed herein includes a bone anchor that includes a anchor body comprising an axial bore, a plurality of bone-engaging tines extending distally from the anchor body, and a spreader positioned between the bone-engaging tines, wherein the spreader is configured to expand the tines outward upon distal movement of the spreader relative to the anchor body, wherein the spreader comprises two suture channels configured in a cross pattern, wherein each channel is configured to receive a suture loop.

Another embodiment disclosed herein includes a bone anchor inserter that includes a proximal handle portion, an outer tube coupled to the handle portion, an actuator coupled to the handle portion, an inner tube coupled to the actuator and located inside of the outer tube, wherein the actuator is configured such that movement of the actuator relative to the handle portion causes the inner tube or rod to move axially relative to the outer tube, and an aperture in the handle portion configured to allow the passing of sutures from the inner tube to outside of the inserter.

Another embodiment disclosed herein includes a bone anchor and anchor inserter combination, wherein the bone anchor includes a anchor body comprising an axial bore, a plurality of bone-engaging tines extending distally from the anchor body, and a spreader positioned between the bone-engaging tines, wherein the spreader is configured to expand the tines outward upon distal or proximal movement of the spreader relative to the anchor body, and at least one suture loop threaded within the spreader. The anchor inserter can include a handle portion, an outer tube coupled to the handle portion, an actuator coupled to the handle portion and the inner tube, and an inner tube coupled to the actuator and located inside of the outer tube, wherein the inner tube is also coupled to the spreader, wherein the actuator is configured to such that movement of the actuator causes the inner tube and hence the spreader to move axially relative to the outer tube.

Another embodiment disclosed herein includes a method of attaching tissue to bone including inserting a bone anchor in a pre-formed bone hole using an insertion tool, advancing a spreader into the bone anchor using the insertion tool to cause expansion of the anchor against bone, disengaging the insertion tool from the proximal end of the anchor, passing sutures which are secured to the spreader through the tissue, and fixedly securing the sutures on top of the tissue.

Another embodiment comprises a bone anchor including, an anchor body comprising an axial bore, a plurality of bone-engaging tines extending distally from the anchor body, a spreader positioned between the bone-engaging tines, wherein the spreader is configured to expand the tines outward upon distal or proximal movement of the spreader relative to the anchor body; and one or more expandable suture capture tabs coupled to the anchor body, wherein the tabs are configured to collapse inward upon contact with sides of a pre-drilled bone hole.

Another embodiment comprises a bone anchor that is cylindrical in shape. Yet another embodiment provides an anchor body with exterior threads. Still another embodiment provides a bone anchor of claim where the axial bore has interior threads.

Another embodiment provides a bone anchor, wherein the bone-engaging tines comprise teeth adapted to resist removal of the anchor from the bone. In one embodiment, the bone-engaging tines extend from a distal end of the anchor body or where they extend from a proximal end of the anchor body.

Another embodiment comprises a bone anchor where the spreader comprises a distal head and a proximal shaft. In one embodiment of a bone anchor, the spreader comprises exterior threads. In another embodiment for a bone anchor, the axial bore comprises interior threads configured to engage the exterior threads of the spreader.

Another embodiment provides for a bone anchor, wherein the spreader comprises a proximal hexagonal socket. In another embodiment, the spreader tapers distally.

Another embodiment provides for a bone anchor, comprising a cap configured to engage with a proximal end of the anchor body. In yet another embodiment, the cap is coupled to the spreader.

Another embodiment provides for a bone anchor where the spreader comprises one or more suture apertures.

Another embodiment provides for a bone anchor, wherein the tabs extend distally from the distal end of the anchor body. In another embodiment, the tabs extend laterally from an outside surface of the anchor body. In one embodiment, the tabs comprise a cut away portion of the anchor body.

Another embodiment provides for a bone anchor, including, an anchor body comprising an axial bore, a plurality of bone-engaging tines extending distally from the anchor body, a spreader positioned between the bone-engaging tines, wherein the spreader is configured to expand the tines outward upon distal movement of the spreader relative to the anchor body, and an anchor cap configured to engage the spreader and be secured within the axial bore.

Another embodiment provides for a bone anchor, wherein the anchor cap is configured to be secured within the axial bore by snapping into the bore. Yet another embodiment provides for a bone anchor, wherein an inside surface of the axial bore comprises threads and wherein an outside surface of the anchor cap comprises corresponding threads and the anchor cap is configured to be secured within the axial bore by screwing into the bore.

Another embodiment provides for a bone anchor wherein the anchor cap comprises one or more suture apertures. In another embodiment, the anchor cap suture apertures comprise pre-threaded sutures.

Another embodiment provides for a bone anchor inserter including a proximal handle portion, an outer tube coupled to the handle portion, wherein the outer tube comprises an anchor coupling member at its distal end, an inner tube or rod coupled to the handle portion and located inside of the outer tube, and an actuator coupled to the handle portion and the inner tube or rod, wherein manipulation of the actuator causes the inner tube or rod to move axially relative to the outer tube.

Another embodiment provides for an inserter wherein the outer tube is reversibly coupled to the anchor by snapping or screwing. In yet another embodiment for an inserter, the anchor coupling member comprises threads on an interior surface of the outer tube configured to engage corresponding threads on a bone anchor.

Another embodiment provides for an inserter wherein the actuator comprises a lever and cam mechanism, wherein the cam mechanism contacts a proximal end of the inner tube or rod.

Another embodiment provides for an inserter wherein the actuator comprises a rotatable handle coupled to the inner tube or rod and wherein an outside surface of the inner tube or rod comprises threads engaged with corresponding threads on another component of the inserter.

Another embodiment provides for an inserter coupled to a bone anchor that comprises, an anchor body comprising an axial bore, a plurality of bone-engaging tines extending distally from the anchor body, and a spreader positioned between the bone-engaging tines, wherein the spreader is configured to expand the tines outward upon distal or proximal movement of the spreader relative to the anchor body, wherein the anchor coupling member is coupled to the anchor body and the inner tube or rod is coupled to the spreader. Another embodiment further comprises an anchor cap configured to engage the spreader and be secured within the axial bore. Another embodiment provides for an inserter wherein the inner tube engages with the cap which attaches by snapping or screwing to the shaft of the spreader.

Another embodiment provides for an anchor and inserter combination the bone anchor including, an anchor body comprising an axial bore, a plurality of bone-engaging tines extending distally from the anchor body, a spreader positioned between the bone-engaging tines, wherein the spreader is configured to expand the tines outward upon distal or proximal movement of the spreader relative to the anchor body, and an anchor cap configured to be secured within the axial bore, the anchor cap comprising at least one suture aperture, the anchor inserter including, a handle portion, an elongated anchor engaging portion extending distally from the handle portion, the elongated anchor engaging portion comprising an anchor coupling member configured to couple with the anchor body and a cap coupling member configured to couple with the anchor cap, and at least one wire expanding from the handle portion through at least one aperture in the anchor cap. Another embodiment provides for the combination wherein the anchor coupling member is configured to be disengageable from the anchor body. Another embodiment provides for a combination wherein the anchor coupling member is configured to be snapped off the anchor body or be twisted off the anchor body. Another embodiment provides for an anchor and inserter combination wherein the at least one wire is configured to capture sutures through the apertures in the anchor cap. Another embodiment provides for a combination wherein the at least one wire is a nitinol wire. Another embodiment provides for an anchor and inserter combination wherein the at least one wire forms a loop. Another embodiment provides for an anchor and inserter combination wherein the at least one wire is slidably disposed within the elongated anchor engaging portion and at least one aperture.

Yet another embodiment provides for a bone anchor and anchor inserter combination, the bone anchor including, an anchor body comprising an axial bore, a plurality of bone-engaging tines extending distally from the anchor body, and a spreader positioned between the bone-engaging tines, wherein the spreader is configured to expand the tines outward upon distal or proximal movement of the spreader relative to the anchor body; the anchor inserter including, a handle portion, an outer tube coupled to the handle portion, wherein the outer tube comprises an anchor coupling member at its distal end that is coupled to the anchor body, an inner tube or rod coupled to the handle portion and located inside of the outer tube, wherein the inner tube or rod is coupled to the spreader, and an actuator coupled to the handle portion and the inner tube or rod, wherein manipulation of the actuator causes the inner tube or rod and hence the spreader to move axially relative to the outer tube.

Yet another embodiment provides for an anchor and inserter combination wherein the anchor coupling member is configured to be disengageable from the anchor body. In another embodiment for an anchor and inserter combination, the outer tube comprises a shoulder or stopper piece at its distal end so that distal force may be provided by the inserter tool to the top of the anchor while preventing the anchor from progressing too far into the bone. In yet another embodiment provides for an anchor and inserter combination, the handle portion comprises a rotatable portion configured to move the inner tube or rod proximally or distally upon rotation.

Another embodiment provides for an anchor and inserter combination wherein the handle portion comprises a slidable portion configured to move the inner tube or rod proximally or distally upon sliding. In another embodiment for an anchor and inserter combination, the handle portion comprises a lever configured to move the inner tube or rod proximally or distally upon activation.

Another embodiment provides for a method of securing a bone anchor into bone, the method including, positioning a bone anchor according to claim 1 in proximity to a pre-drilled bone hole, placing one or more suture strands behind one or more of the expandable suture capture tabs, inserting the bone anchor into the bone hole, thereby collapsing the suture tabs and securing the suture strands; and moving the spreader proximally or distally to cause the bone-engaging tines to expand outward.

Another embodiment provides for a method wherein the spreader is moved, distally or proximally relative to the anchor body, by a surgeon with the use of an insertion tool to hold the spreader in place while the surgeon exerts distal or proximal force. Yet another embodiments provides for a method wherein the spreader is moved proximally or distally with an insertion tool to cause the bone-engaging tines to expand outward.

Another embodiment provides for a method wherein the spreader locks into position and remains in the anchor upon full expansion of the tines. Another Another embodiment provides for a method comprising removing the insertion tool after the spreader has caused the tines to expand and become engaged with the bone. Yet another embodiment provides for a method wherein the anchor is even with or below the bone's surface when the tines are fully expanded outward and the anchor is fixed in the bone.

Another embodiment provides for a method wherein the sutures can be released by partially removing the anchor from the bone hole, thereby releasing the tabs.

Another embodiment provides for a method of securing a bone anchor into bone, the method including, inserting a bone anchor in a pre-drilled bone hole, moving the spreader distally to cause the bone-engaging tines to expand outward, and securing the anchor cap within the axial bore.

Another embodiment provides for a method wherein the anchor cap comprising one or more suture apertures. Yes another embodiment, provides a method further comprising passing at least one length of suture through at least one suture aperture.

Still yet another embodiment provides for a method wherein fixedly securing the anchor cap to the bone anchor causes the sutures to be clamped between the anchor cap on another component of the bone anchor.

Yet another embodiment provides for a method wherein the anchor cap is advanced to the bone anchor by an insertion tool comprising an outer tube and an inner rod wherein the outer tube is coupled to the bone anchor and the inner rod is coupled to the anchor cap.

Another embodiment provides for a method wherein the sutures are also coupled with another bone anchor already inserted and engaged with the bone such that after fixedly securing the anchor cap to the bone anchor, suture is secured between the two bone anchors.

Another embodiment provides for a method wherein the anchor cap is secured within the axial bore by engaging with threads on the spreader in a screwing motion or by snap-fitting onto the spreader.

Another embodiment provides for a method of attaching suture to a bone anchor, the method including, inserting a first bone anchor in a pre-drilled bone hole, the first bone anchor comprising an anchor cap configured to be fixedly secured to a proximal end of the bone anchor, the anchor cap comprising one or more suture apertures, advancing one or more wires through one or more of the suture apertures, coupling one or more sutures with the one or more wires, withdrawing the wires through the suture apertures, thereby pulling the sutures through the apertures, and fixedly securing the anchor cap to the proximal end of the first bone anchor. In one embodiment, fixedly securing the anchor cap to the first bone anchor causes the sutures to be clamped between the anchor cap and another component of the first bone anchor. In another embodiment, the method provides advancing the anchor cap to the first bone anchor using an insertion tool comprising an outer tube and an inner rod wherein the outer tube is coupled to the first bone anchor and the inner rod is coupled to the anchor cap.

Another embodiment provides for a method, wherein the wires are at least partially contained within the outer tube of the insertion tool.

Another embodiment provides for a method wherein the sutures are also coupled with a second bone anchor, wherein the second bone anchor is inserted and engaged with the bone prior to insertion of the first bone anchor such that after fixedly securing the anchor cap to the first bone anchor, suture is secured between the two bone anchors.

Another embodiment provides for a method wherein the one or more wires comprise a loop and coupling the one or more sutures with the one or more wires comprises passing one or more sutures through the loop.

Another embodiment provides for a method of attaching suture to a bone anchor, the method including, inserting a bone anchor in a pre-drilled bone hole, passing one or more suture strands through one or more suture apertures in an anchor top configured to couple to the proximal end of the bone anchor, wherein during said passing, the anchor top is not coupled to the bone anchor, sliding the anchor top down the suture strands until the anchor top is in proximity to the bone anchor; and fixedly securing the anchor top to the proximal end of the bone anchor.

Another embodiment provides for a method wherein passing the one or more suture strands through the one or more suture apertures is conducted outside of a patient's body.

Yet another embodiment provides for a method where sliding the anchor top down the suture strands comprises transporting the anchor top through a cannula inserted into the patient's body.

In another embodiment provides for a method wherein fixedly securing the anchor cap to the bone anchor causes the sutures to be clamped between the anchor cap and another component of the bone anchor.

Another embodiment provides for a method wherein the bone anchor is fully inserted and secured to the bone before the anchor top is fixedly secured onto the bone anchor.

Yet another embodiment provides for a method wherein the anchor cap comprises ridges in a region where the sutures are clamped between the anchor cap and another component of the bone anchor.

Another embodiment provides for a method wherein the sutures are tensioned before final insertion of the cap is fixedly secured to the bone anchor.

Still another embodiment provides a method of manufacturing a bone anchor, including, cutting a pattern into a flat piece of material and stamping the flat piece of material with successive dies to obtain the bone anchor shape. In one embodiment, the flat piece of material is one of: titanium stainless steel, plastic, polymeric materials and fiberglass.

Another method provides where the pattern is cut into the flat piece of material by a laser or by chemical etching and then is stamped into a sheet of material and bent or folded to form a three-dimensional anchor.

The present embodiment is particularly suited for use in arthroscopic procedures, including but not limited to rotator cuff surgery, biceps tenodesis, and repair of a torn ACL. More broadly, it can be used in any procedure in which it is desired to fix soft tissue to bone, including not only arthroscopic procedures, but also open surgery, and can be used for such diverse purposes as bladder neck suspension, tendon and ligament affixation or repair, prosthetic attachment, and rotator cuff repair.

BRIEF DESCRIPTION OF THE DRAWINGS

FIGS. 18A and 18B depict an embodiment of a piercing bendable tine in an un-deployed (FIG. 18A) and deployed (FIG. 18B) state. FIGS. 18A and 18B depict an embodiment of the anchor with an insertion tool that uses a hex and screw configuration.

DETAILED DESCRIPTION OF CERTAIN EMBODIMENTS

Various embodiments include an anchor that can be inserted into bone and to which sutures can be attached. In one embodiment, the anchor comprises expandable tines that secure the anchor in bone after insertion. In some embodiments, a spreader is provided that can be used to expand the tines. Some embodiments include one or more suture lengths that are pre-attached to the spreader.

Figure 1A:
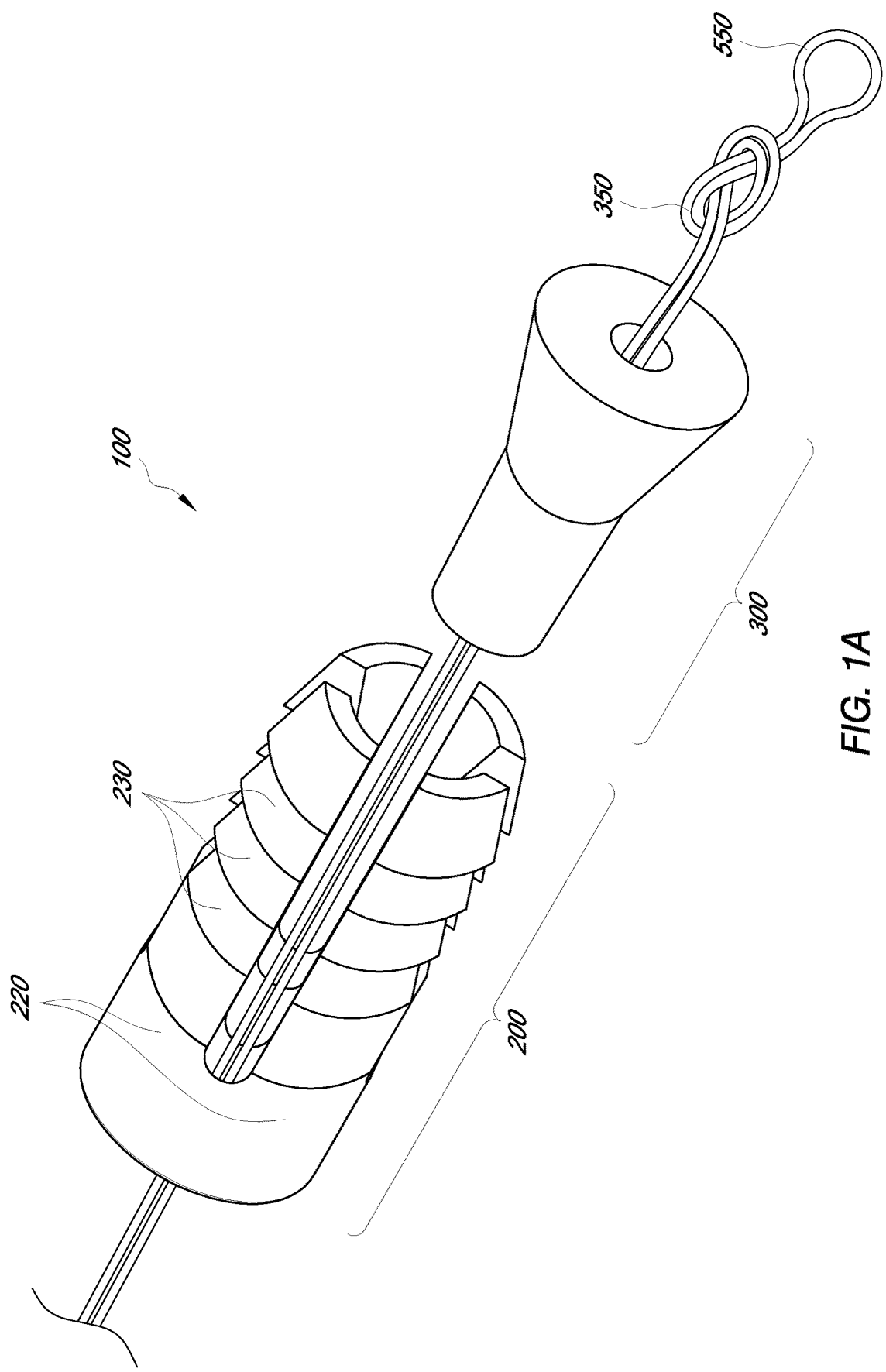
FIG. 1A shows a side perspective view of one embodiment of a suture anchor in an undeployed or unexpanded state.

In various embodiments, soft tissue may be attached to bone utilizing one or more suture anchors. FIG. 1A depicts a side perspective view of a suture anchor 100 comprising an anchor body 200 and a spreader 300. The anchor body 200 is comprised of tines 220 and teeth 230. The tines 220 expand from the distal end of the anchor body 200 when the spreader 300 is engaged with the anchor body 200. The proximal end of the spreader 300 is configured to fit into the distal end of the anchor body 200. In FIG. 1A, the suture anchor 100 is in the undeployed, or unexpanded position. A suture loop 550 extends through the anchor body 200 and the spreader 300 where it is securely knotted 350 outside of the distal end of the spreader 300. The knotted suture 350 is tightened, such that suture loop 550 forms a tightened knot that cannot pass back through the spreader 300 or the anchor body 200 but rather is fixed outside of the spreader 300. Alternatively, the suture loop may be secured against being pulled through the spreader 300 using securement mechanisms other than knot, such as cross-pin or biocompatible adhesive.

Figure 1B:
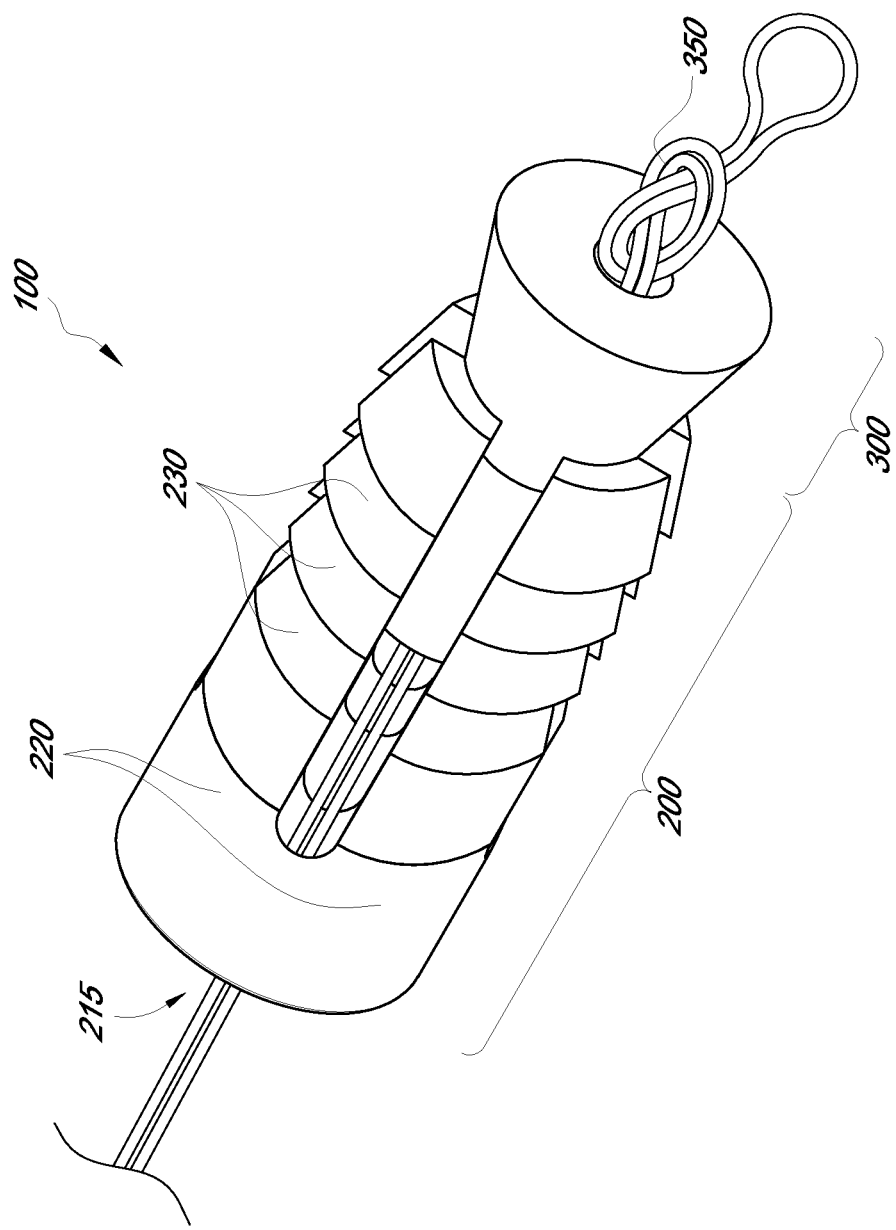
FIG. 1B shows a perspective view of one embodiment of an undeployed suture anchor wherein the spreader is partially inserted into the bone anchor.

FIG. 1B shows another side perspective view of the unexpanded suture anchor 100. In this embodiment, the spreader 300 is slightly inserted in the axial bore 215 at the distal end of the anchor body 200.

Figure 1C:
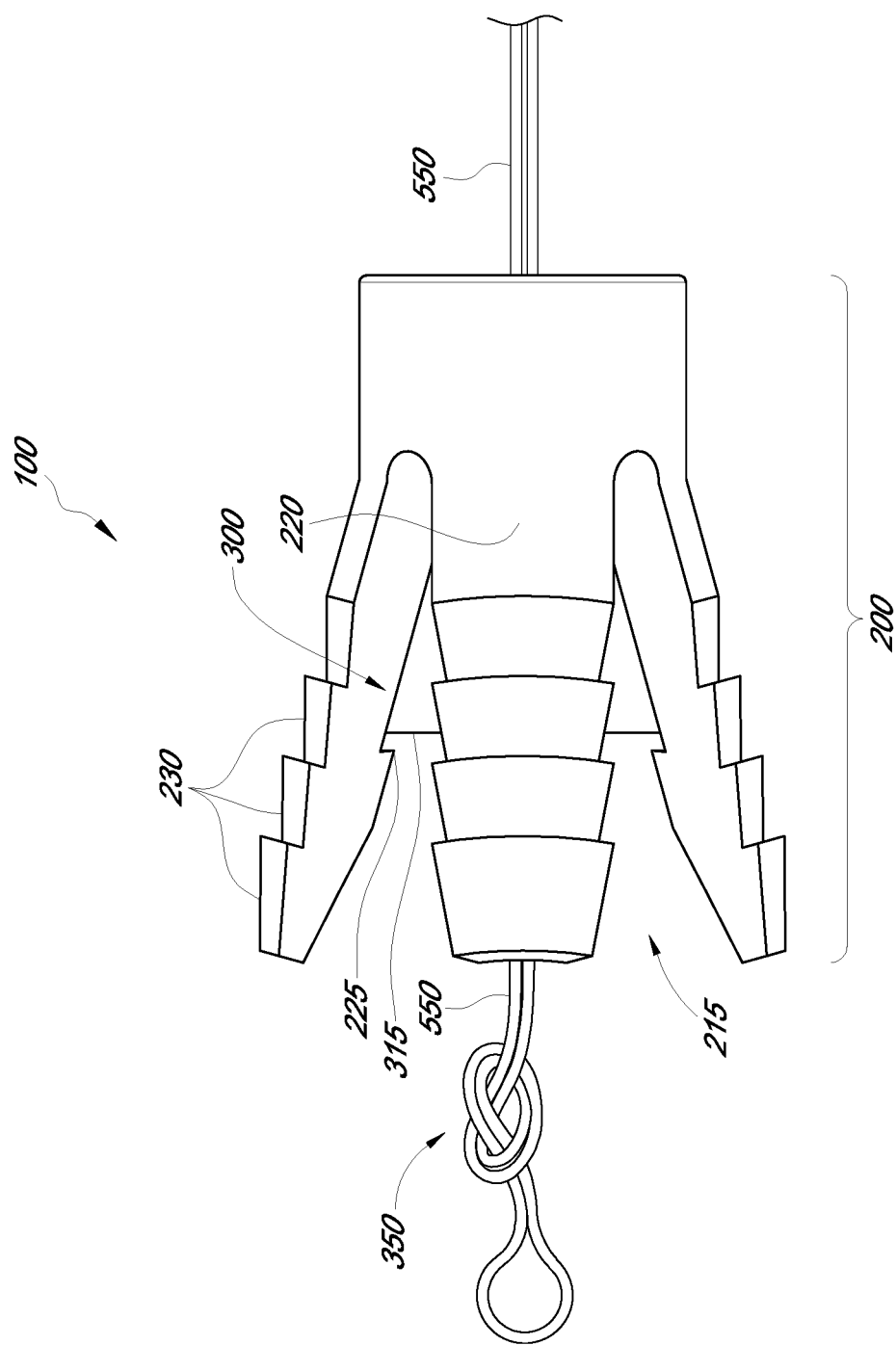
FIG. 1C shows a side view of one embodiment of a suture anchor in the deployed or expanded state.

FIG. 1C shows a side view of the suture anchor 100 in the deployed or expanded position. In the deployed or expanded position, the spreader 300 has been drawn up into the anchor body 200 causing the tines 220 to expand from the distal end of the anchor body 200. When deployed, the teeth 230 engage with the bone, thereby securing the anchor within the bone.

The inside surface of the anchor body 200 may comprise a grooved surface 225 to engage with the ridge 315 of the spreader 300 to lock the spreader 300 into place when the anchor body 200 is fully deployed. In one embodiment, the grooved surface 225 is on the inside surface of one or more of the times 220. The grooved surface 225 is oriented such that the distal end of the spreader 300 can be easily moved in the proximal direction in axial bore 215 of the anchor body 200 with the ridge 315 snapping into the groove 225 as the distal end is moved proximally. However, when the ridge 315 is snapped into groove 225, distal movement of distal end is inhibited. In some embodiments, the groove 225 can exist at different locations on the inside surface of the axial bore or even along substantially the entire inside surface of the axial bore 215. In some embodiments the anchor body 200 may be coupled to the spreader 300 in several positions, such as by inclusion of multiple grooves. In other words, in one embodiment the spreader 300 need not be inserted into the anchor body 200 as far as it will go for it to be secured to the anchor body 200.

Although a grooved surface is illustrated, it will be appreciated that other shapes are also contemplated, including multiple concentric grooves, a series of protruding ridges, or any other suitable structure that permits a spreader 300 to be securely locked within the the anchor body 200.

Figure 1D:
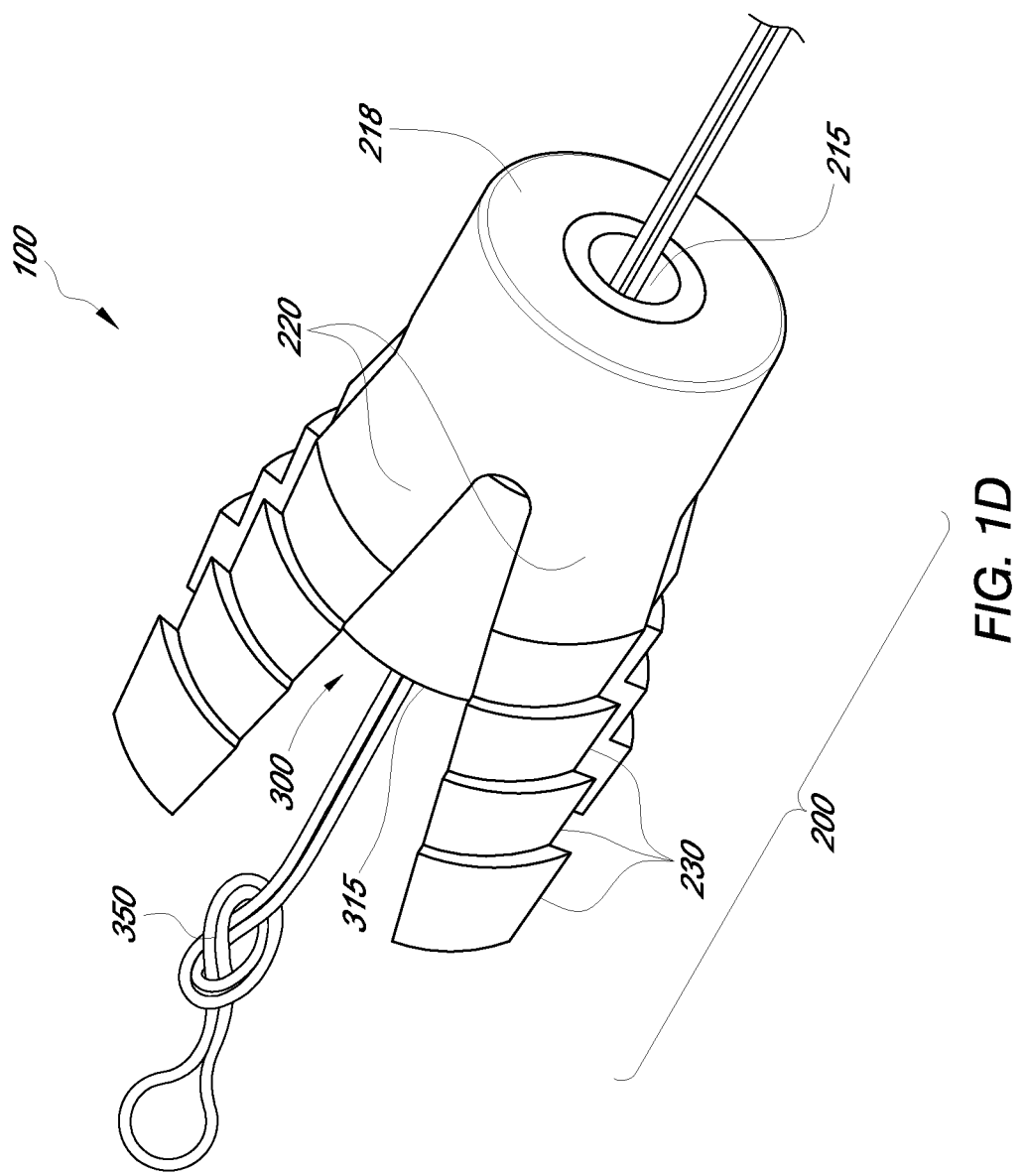
FIG. 1D shows a perspective view of one embodiment of a suture anchor in the deployed or expanded state.

With reference to FIG. 1D, which is a perspective view of the top and side of anchor body 200 engaged with the spreader 300, the top (proximal end) comprises a hole 215 in the center for receiving the suture. In some embodiments, the top surface 218 of the anchor body 200 may be textured such as with a scallop shape or grooves so as to inhibit movement of an insertion tool against this surface.

During deployment, the spreader 300 is drawn into the anchor body 200 causing the tines 220 to expand from the distal end of the anchor body 200. Also during deployment, the spreader 300 is drawn into the anchor body 200 until the ridge 315 of the spreader 300 passes a groove 225 (not shown) in the anchor body 200. When the spreader passes this point, the ridge 330 and groove 225 engage or click and the spreader 300 is locked into place and the anchor body 200 cannot undeploy or reverse and the spreader 300 cannot reverse direction.

Figure 1E:
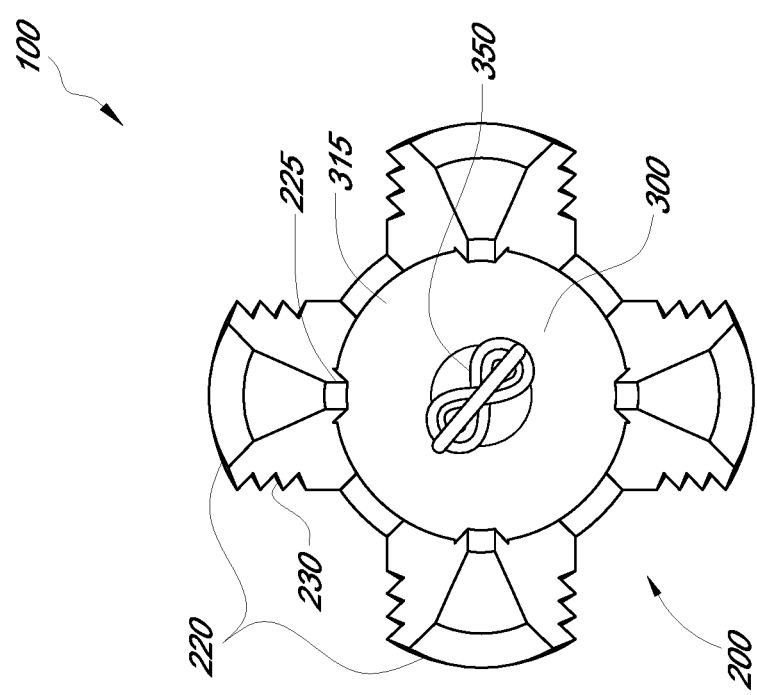
FIG. 1E shows another perspective view of one embodiment of a suture anchor in the deployed or expanded state.

FIG. 1E shows a distal view of the suture anchor 100. In this view the anchor body 200 is fully deployed. The spreader 300 is securely fixed into the anchor body 200 and the ridge 315 and groove 225 of the anchor body 200 will keep the spreader 300 from being uninserted or reversed from the anchor body 200. The spreader 300 will remain permanently located in the bone anchor 200 to help prevent collapse, movement or slipping of the components and of the anchor 200 as a whole.

Figure 2A:
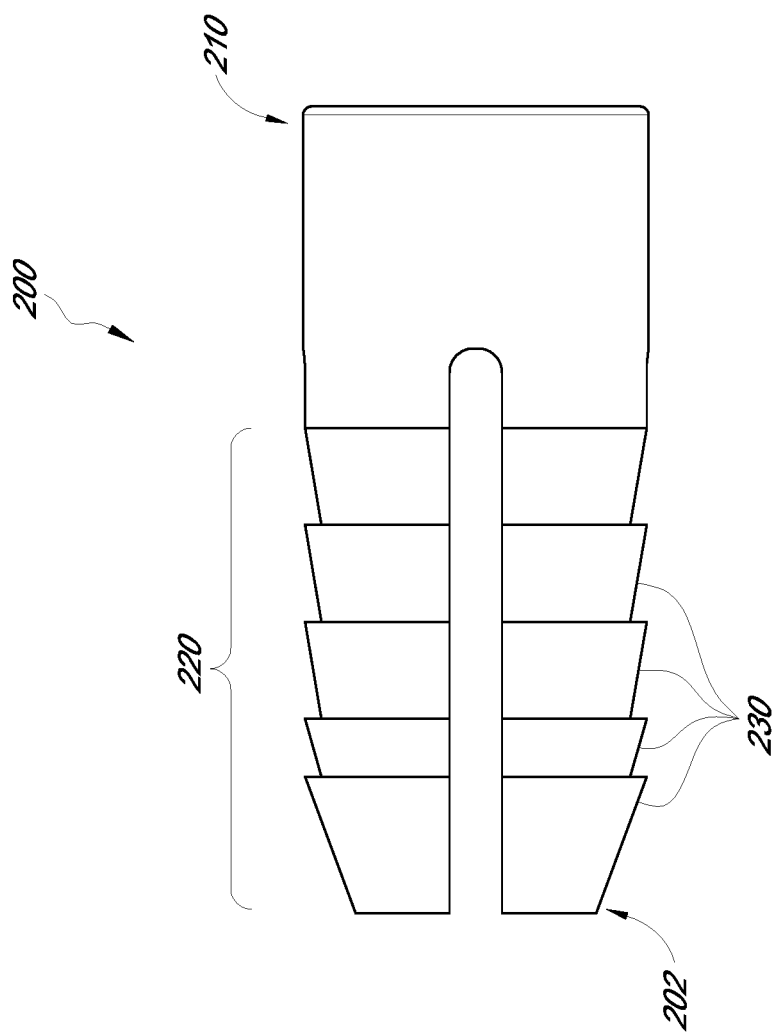
FIG. 2A depicts a side view of one embodiment of an anchor body.
Figure 2B:
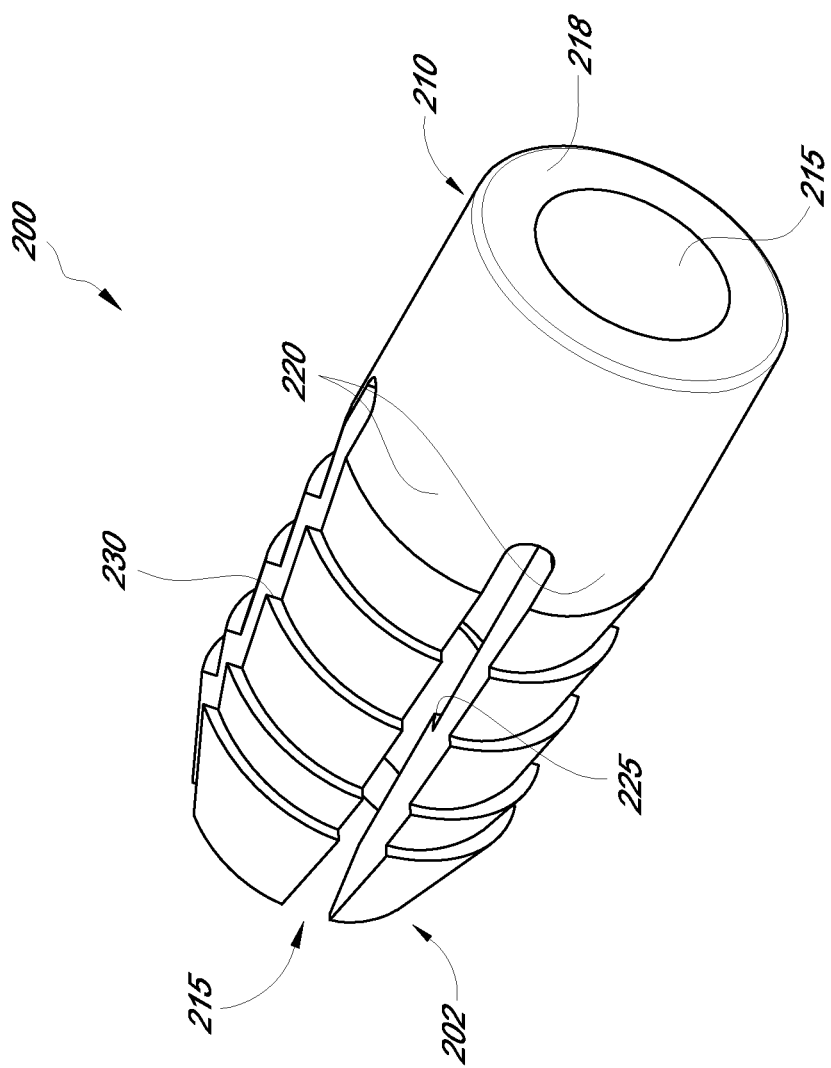
FIG. 2B depicts a perspective view of one embodiment of an anchor body.
Figure 2C:
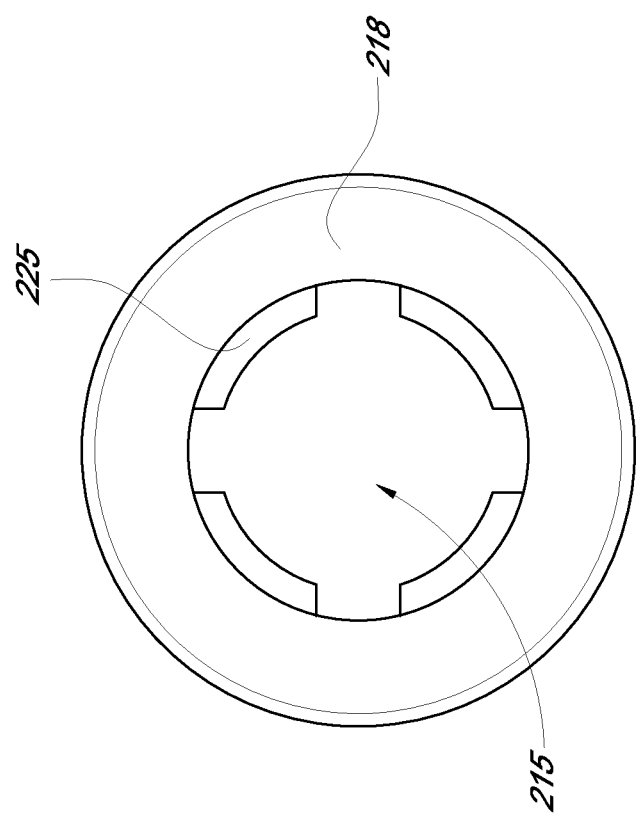
FIG. 2C depicts another perspective proximal view of one embodiment of an anchor body.
Figure 2D:
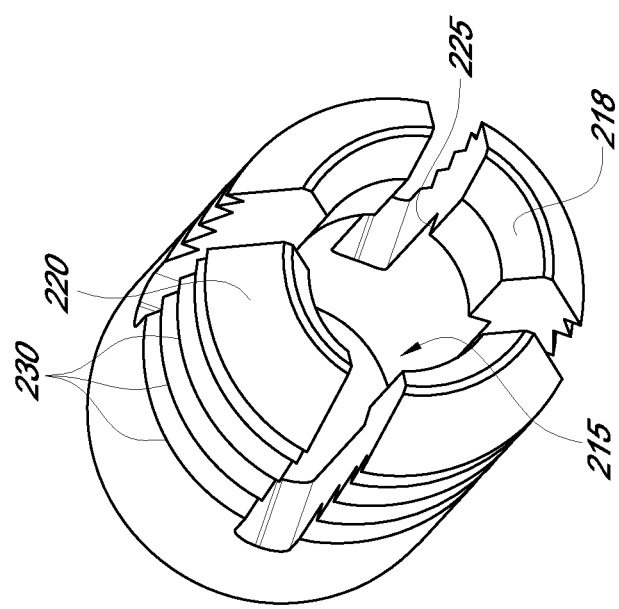
FIG. 2D depicts a perspective distal view of one embodiment of an anchor body.

FIGS. 2A-2D depict an embodiment of an undeployed anchor body 200. FIG. 2A depicts a side view of the anchor body 200. FIG. 2B depicts a perspective view of an embodiment of the anchor body 200. FIG. 2C depicts a view from the proximal end of the anchor body 200, and FIG. 2D depicts a perspective view from the distal end of the anchor body 200.

The anchor body 200 can generally have any shape, for example a circular shape, or a polygon of three or more sides. The proximal end 210 of the undeployed anchor body 200 is generally cylindrical in shape with a diameter larger than distal end 202. With reference to FIGS. 2B-2D, a hole 215 may advantageously be provided in the center of proximal end 210. With reference to FIG. 2B, the bottom of distal end 202 also contains a hole 215. Hole 215 comprises a central bore that extends through the anchor body 200. In one embodiment the anchor body 200 comprises a groove 225 in its inner surface, as shown in FIGS. 2C-2D. Thus, the inner surface of the anchor body 200 is not flat. In one embodiment, some or all of these surfaces may be textured such as with a scallop shape or grooves so as to inhibit movement of spreader 300 once it is withdrawn into the anchor body. In one embodiment, texturing in the inner surfaces of anchor body 200 matches texturing in the outer surfaces of the spreader 300. It will be appreciated that the illustrated embodiments represent only one possibility; thus, other shapes for the distal surface of proximal end 204 may also be used.

In the depicted embodiment, the anchor body 200 has a circular shape. The distal end 202 of the anchor body 200 is configured to receive the spreader 300 and sutures via an axial bore 215. The axial bore 215 in anchor body 200 is an opening into an axial bore into and through the anchor body 200. The sides of the bore preferably include a groove 225 for engaging with the spreader 300, described below. It will be appreciated that other methods of securing the spreader 300 within the anchor body 200 may be used, such as a frictional fit or threading. The axial bore 104 can generally be any shape, for example, a circle shape or a polygon shape. Circular forms are preferred for the axial bore 215.

The anchor body 200 is comprised of tines 220 which spread outwardly when engaged with the spreader 200. The tines 220 engage with the bone fixedly securing the anchor body 200 in the bone. The tines may comprise a plurality of teeth 230 which further engage with the bone in the deployed suture anchor 100. When the tines 220 are expanded (spread outward), the teeth 230 can engage the bone to hold the anchor in place. In one embodiment, the anchors described herein provide for increased suture pull-out strength and to retain the tissue by multiple sutures.

In one embodiment, the anchor body 200 has from about two to about six tines 220 extending therefrom. In a preferred embodiment, the anchor body 200 has four tines 220 extending therefrom. Each tine 220 may comprise, along its outward-facing edge, one or more teeth 230, preferably three to six in number, which can be engaged with the bone once the tines 220 are spread apart after insertion of the anchor 100. Each tine's distal end can be formed to a slant or pointed edge. In other embodiments, the distal end of each tine is either straight or any other effective shape.

The anchor is expandable at its distal end by the tines spreading outward. As the tines are spread apart with the spreader (described below), the teeth 230 of the tines 220 become engaged in bone material such that the anchor is securely attached to the bone. Distal expansion provides improved pull-out strength. Where multiple teeth 230 are present, they may increase in size as they are positioned more distally from the anchor body 200. The teeth 230 are preferably tapered to sharpened points that are able to penetrate tissue and/or the interior matrix (cancellous portion) of the bone. Once expanded, the spreader 300 remains in the anchor 200.

The tines 220 are preferably symmetrically positioned about the anchor body 200. In one embodiment, when the tines 220 are in their un-expanded configuration, the distal ends of the tines 220 are in a first internal lateral position, as depicted in FIG. 1A and FIG. 1B, such that they are parallel to or angled internal to the longitudinal axis. In one embodiment, the internal angle is from about 8° to about 15°. When in the internal lateral position, the teeth 230 may be at or within the cylindrical, axially extending region defined by the anchor body 200. During and after insertion of a spreader, as the distal ends of the tines 220 are moved to their second or external, more lateral position, the distance between the ends and the longitudinal axis of the anchor 100 will increase to place the tines 220 at or beyond the cylindrical axially extending region defined by the anchor body 200. (See FIGS. 1C and 1D).

The number of tines 220 and teeth 230 can vary. In one embodiment, there are four tines 200 with five teeth 230 per tine 220. The distal end 210 of the anchor body 200 is configured to receive a portion of an anchor inserter, which can be inserted through the hole 215 in the center of the anchor body 200 to couple with a spreader 300.

The distal end 202 of the anchor body 200 may advantageously be tapered to facilitate insertion of the anchor body 200 into bone. In one embodiment, the anchor body 200 has at its widest point, a diameter not larger than the widest point of the spreader 200.

Figure 2F:
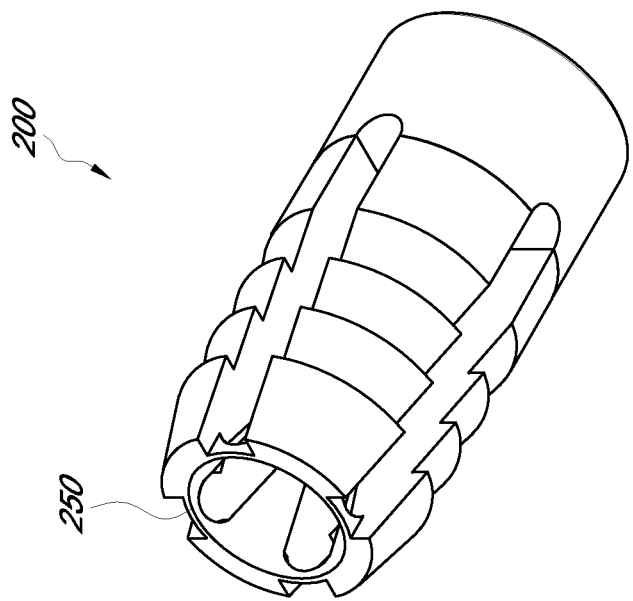
FIGS. 2E and 2F depict an alternate embodiment of an anchor body.
Figure 2E:
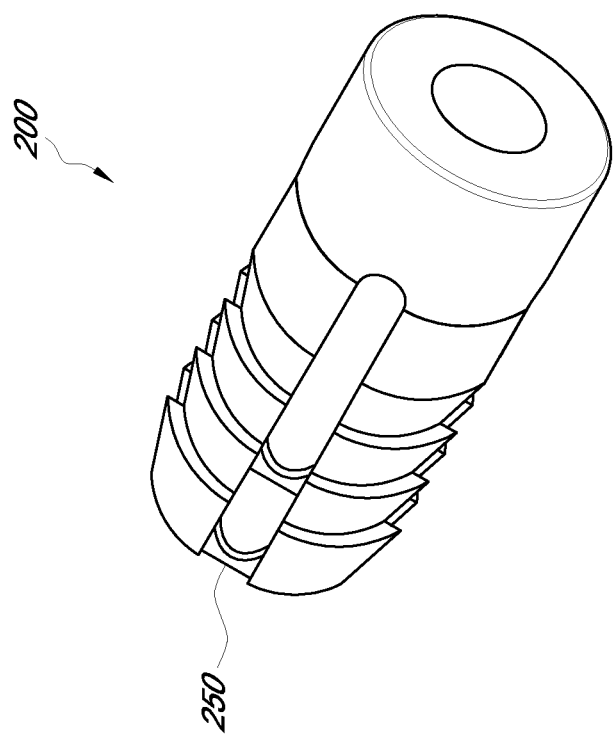

FIGS. 2E and 2F depict an alternate embodiment of an anchor body 200. In this embodiment, the anchor body also comprises webbed portions 250 across the distal ends of the tines 230. These webs 250 are easily broken when the spreader 300 is engaged with the anchor body 200. The webs 250 protect against premature deployment of the anchor upon insertion into the bone by keeping the tines 220 intact until they are expanded via the spreader 300.

The exact size and dimensions of the anchor can vary with its intended use and the patient size. The following overall dimensions are suited for the shoulder and knee joints of an adult human of average size, and can be modified for specific patients or uses. The diameter of the anchor can have, but is not limited to, a range from 3 to 10 mm.

The anchor can be made of any biocompatible or physiologically inert materials. In one embodiment, plastics, including but not limited to polyetheretherketone (PEEK) or other suitable materials, may be used. Other embodiments can include titanium and its alloys, stainless steel, and cobalt based alloys. Bioabsorbable materials can also be used.

Figure 3A:
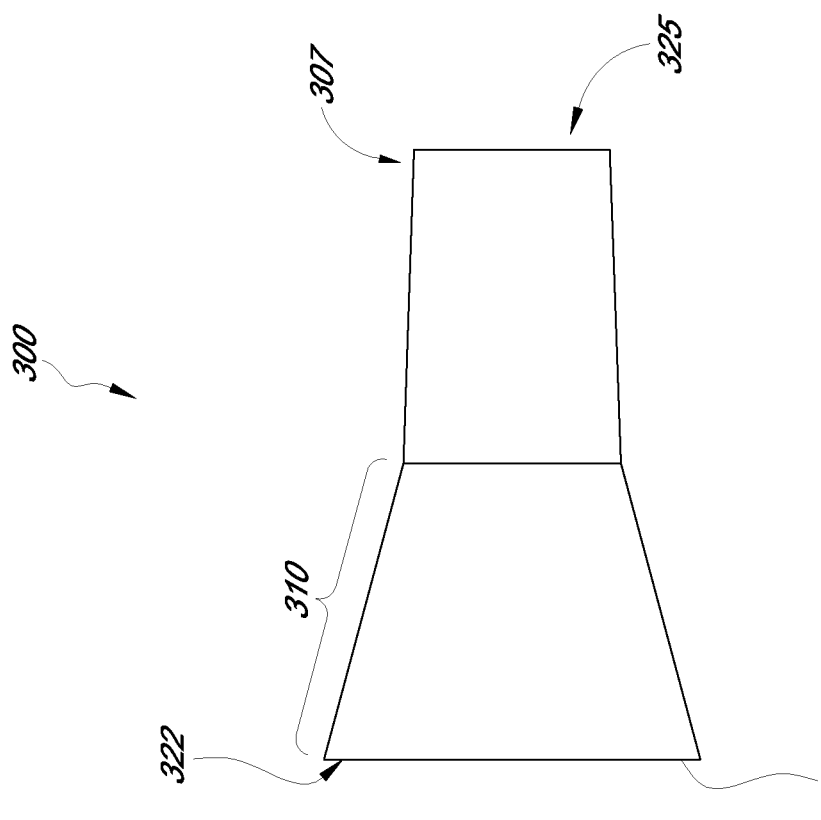
FIG. 3A depicts a side perspective view of one embodiment of a spreader.
Figure 3B:
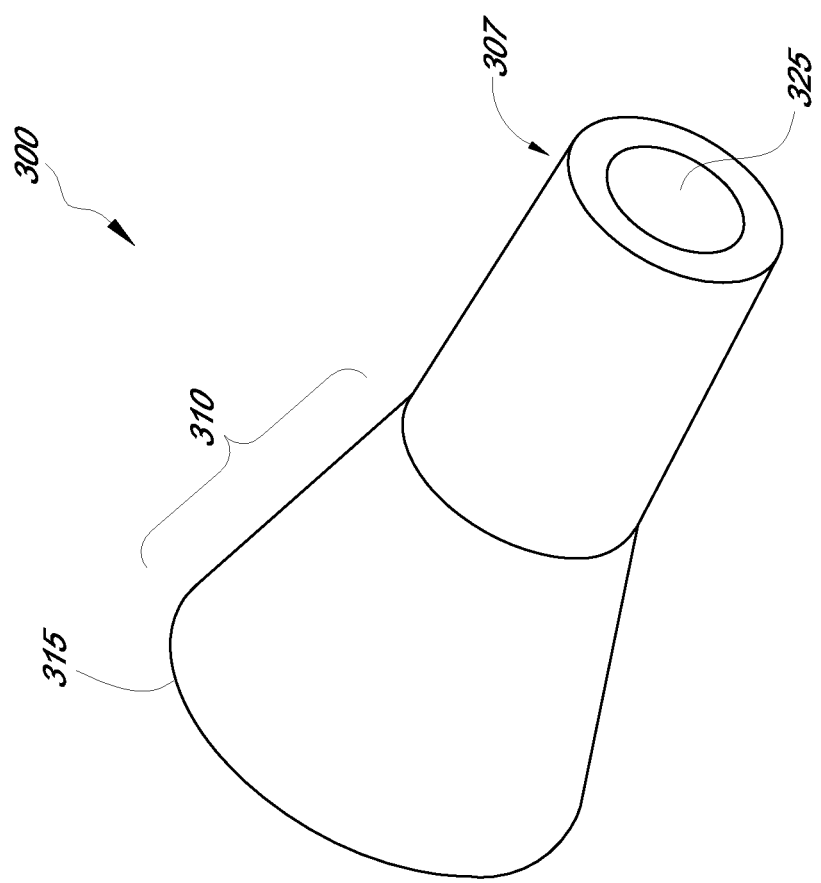
FIG. 3B depicts a perspective view of one embodiment of a spreader

FIG. 3A shows a side view of an embodiment of the spreader 300. FIG. 3B shows a perspective view of the spreader 300. The spreader 300 comprises a generally tube shaped base 310 at the proximal end 307 with a axial bore 325 for receiving sutures and an insertion tool, a generally conical shaped spreader at the distal end which is wider than the proximal end, and an optional ridge 315 at the tip of the distal end. The distal end can further comprises a flat area around the axial bore 325. The proximal end 307 is configured for receiving sutures and coupling with an inserter. For instance, in this embodiment, the proximal end 307 of the spreader 300 comprises a hole 325 that receives the inserter tool for coupling.

The spreader 300 comprises the base section which joins with the gradually expanding distal spreader end. The distal end is generally cylindrical-shaped or cone-shaped 310, meaning that it gradually widens in a conical shape from the base section to the distal end of the spreader 300 which comprises a flat area and through which the axial bore 325 extends. In one embodiment, the distal end may also comprise a ridge 315, which may optionally be slightly undercut 322 to result in a stronger lock in the bone then when the anchor is fully deployed.

The axial bore 325 may be used to receive sutures (see FIGS. 1A-1E). In one embodiment, a loop of suture is secured through the axial bore 325 such that two lengths of suture extend from the spreader for use in a surgical procedure. The distal end of the spreader 300 comprises one opening to the axial bore 325 through which the suture loop 550 extends. The resulting two suture lengths extend from the proximal end of the spreader through the axial bore 325. The suture loop 550 extending through the distal end of the spreader 300 can be secured, for example, by a knot 350 in the loop such that it cannot be moved or forced back through the axial bore 325.

The spreader 300 is configured to be drawn through the distal end of the anchor body 200 via an insertion tool. As the suture anchor 100 is deployed, the spreader 300 is further advanced into the anchor body 200, spreading the tines 220 of the anchor body 200 until the ridge 315 of the spreader 300 engages the groove 225 in the inside of the anchor body 200 at which point it locks into place. In one embodiment, the ridge 315 is undercut 322 providing even more security against reversing. In one embodiment, the ridge and groove is optional.

As discussed above, the tines 220 in the anchor may be in a low-profile streamlined position prior to insertion into bone. A spreader 300 is used after insertion to expand the tines 220 such that their teeth 225 engage bone. The spreader 300 may comprise any suitable shape configured to be inserted through the axial bore 215 in the anchor body 200 and make contact with the tines 225. The spreader 300 may be at least partially positioned within the axial bore of the anchor prior to tine expansion as depicted in FIG. 1B. As the spreader 300 is moved from a first lower position to a second upper position, the proximal end of the spreader 300 is designed to spread or force the tines 220 from a first low-profile position (for example, an internal lateral position) to a second external lateral position. In one embodiment, the proximal end of the spreader 300 may have ridges to assist in preventing slippage or mis-alignment.

The spreader 300 will remain in the anchor with the tines 220 in their fully spread position. The force provided by the tines' 220 interaction with the bone keeps the spreader 300 tightly engaged. Further protection against slipping or tilting of the spreader 300 is provided by the optionally ridged sides of the spreader 300. In one embodiment, the spreader 300 may have ridges or indentations to assist in a tight fit such that accidental slipping or adjustments are minimized. In one embodiment, one or more of the tines 220 have an indentation on a side facing the central axis of the anchor. A ridge on the spreader can then engage the indentation, thereby stabilizing the spreader 300 and preventing the spreader 300 from being advanced too far into the anchor. In an alternative embodiment, the spreader comprises an indentation (for example, an indentation in a ridge on the spreader 300) that can engage with a protrusion on a side of a tine facing the central axis of the anchor. In addition, to stabilizing the spreader 300 and preventing over insertion, this feature also prevents rotation of the spreader 300 relative to the anchor.

In a preferred embodiment, the anchor 100 is made entirely of a biocompatible engineering plastic such as polyether-ether-ketone (PEEK). Other embodiments include an anchor entirely or in part of a non-metallic substance that is biocompatible. Biocompatible materials such as poly ether ketone (PEK), polyethermide (ULTEM), ultrahigh molecular weight polyethylene (UHMPE), or some other engineering polymer materials known to those of skill in the art may be used. A non-metallic anchor system may provide certain advantages such as, for example, eliminating MRI artifacts.

Figure 4:
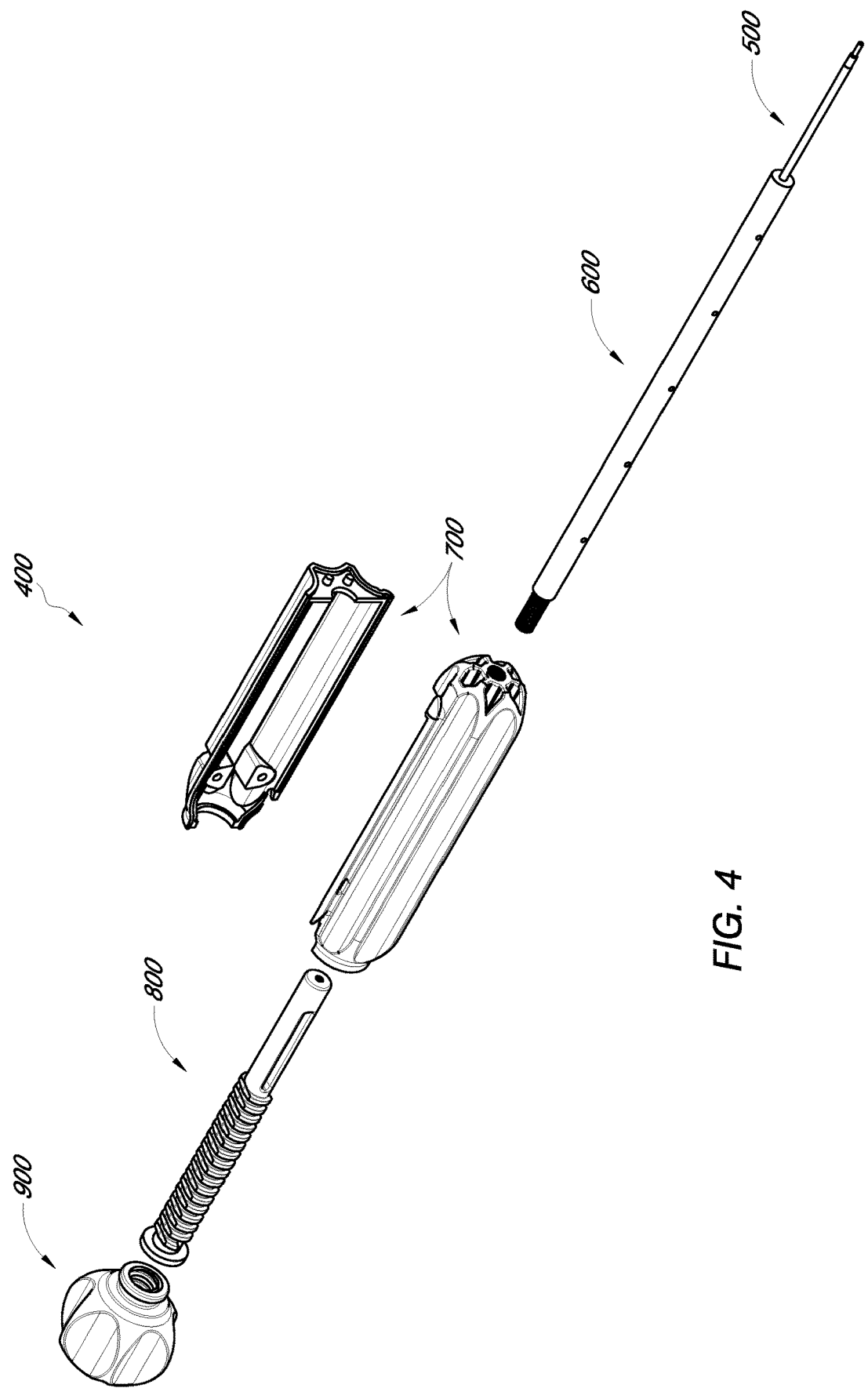
FIG. 4 shows an exploded view of one embodiment of an inserter tool.

FIG. 4 depicts individual components of an inserter tool. The inserter tool comprises an inner tube 500, an outer tube 600, a handle body 700, a threaded actuator shaft 800, and a deployment knob 900. In one embodiment, the inserter 400 is coupled to the suture anchor 100 during manufacturing. In a preferred embodiment, the inserter tool is disposable.

The inserter tool 400 is designed to insert and manipulate a suture anchor such as the suture anchor described in FIG. 1A and FIG. 1B. In one embodiment, the suture anchor is manufactured to be attached to the inserter tool before packaging. In other embodiments, the suture anchor is coupled to the inserter tool prior to insertion. In a basic configuration, the inserter tool is assembled as follows: the inserter tool 400 is configured such that the inner tube 500 is disposed within the outer tube 600. The outer tube is configured to fit against the proximal end of the anchor. The inner tube 500 extends through outer tube 600 and is configured to attach to the spreader 300 via threading on both the proximal hole in the spreader 300 and threading on the distal end of the inner tube 500. The proximal end of the outer tube 600 is connected to a handle 700 and the inner tube 500 extends through the proximal end of the outer tube 600 and screws into the threaded actuator shaft 800. The actuator shaft extends just past the proximal end of the handle 800 where it is configured to engage with a deployment knob 900.

The individual components of the inserter tool 400 are further described in detail below.

Figure 5A:
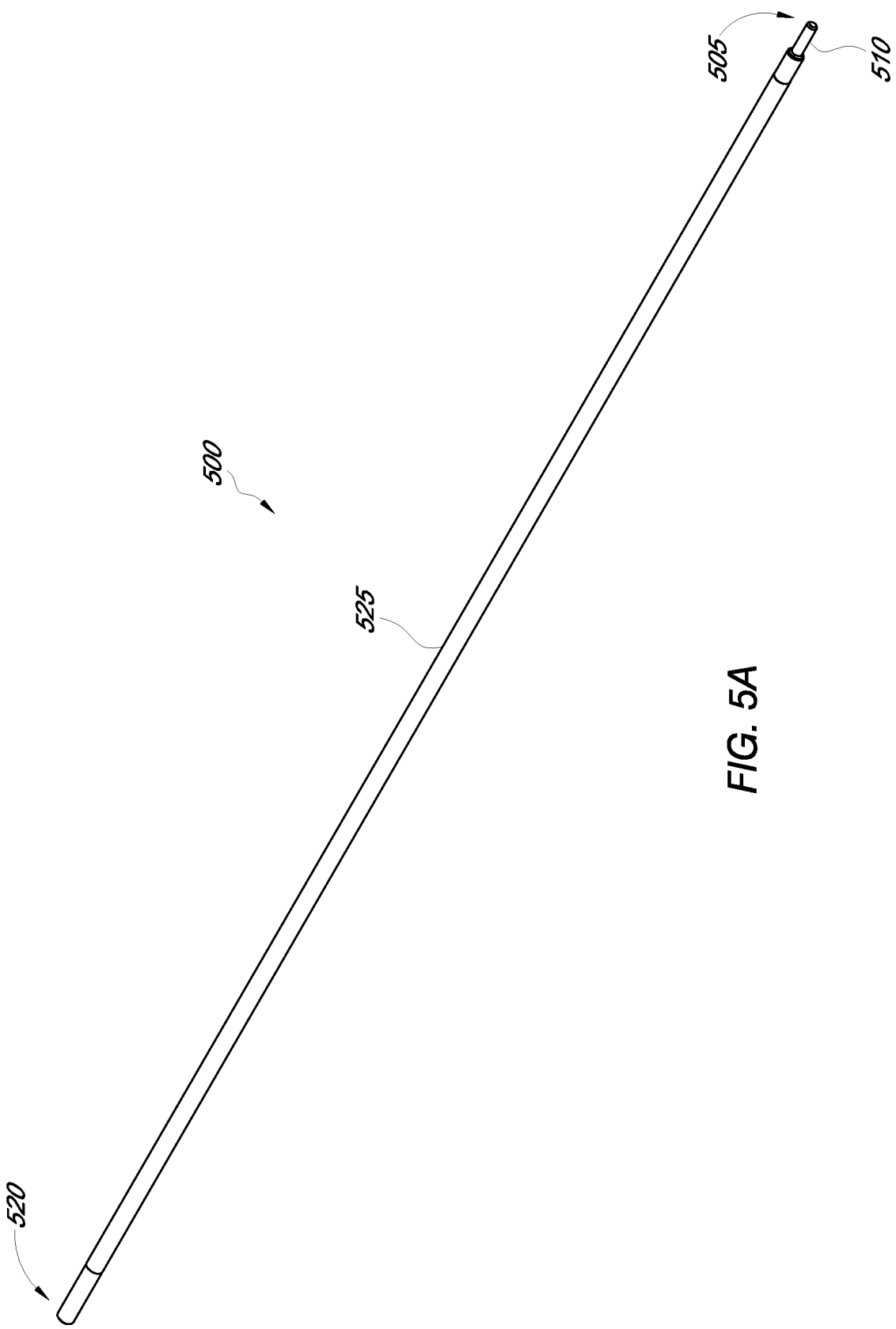
FIG. 5A shows a perspective view of one embodiment of an inner tube component of an insertion tool.

FIG. 5A shows a perspective view of an embodiment of the inner tube 500. The inner tube comprises a distal end configured to secure to the spreader 300 and receive sutures running through the inner tube, and a proximal end which is configured to interact with the other components of the inserter, for example, the actuator shaft 800. The inner tube 500 is configured such that its proximal end is advanced through the outer tube 600 and into the handle 700 where it is further secured within the actuator shaft 800 via threading. The distal end of the inner tube 500 is configured to be advanced through the axial bore in the anchor body 200 and then secured to the spreader 300 until the suture anchor 100 is fully deployed and the inner tube 500 is separated from the anchor 200.

The inner tube 500 extends through the axial bore 225 in the anchor body 200 before coupling with the spreader 300. In one embodiment, the inner tube 500 couples with the spreader 300 through threads on the end of the inner tube 500 and within the proximal end of the spreader 300. In other embodiments, the inner tube 500 may couple to the spreader 300 through other securing mechanisms such as adhesions, welding or frictional fit. In some embodiments, the inner tube 500 may be an inner rod.

Figure 5B:
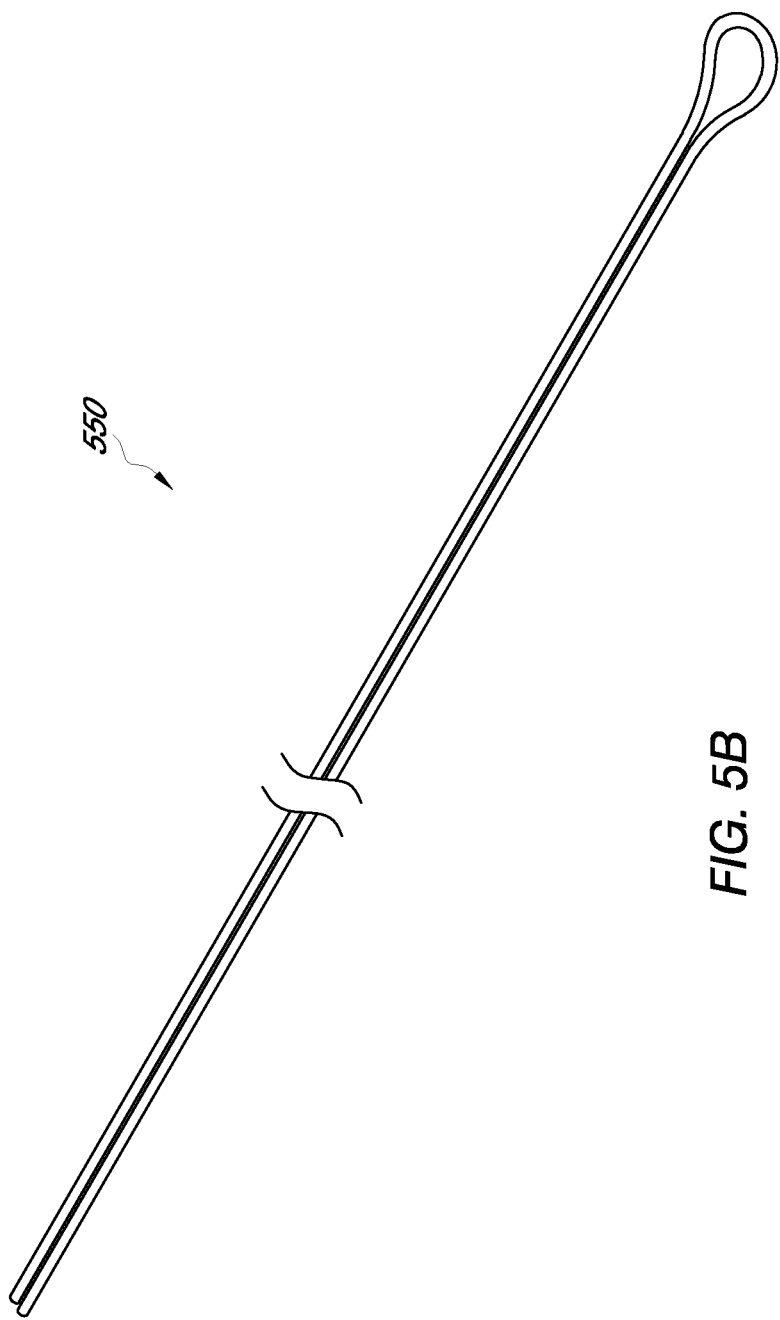
FIG. 5B shows a view of one embodiment a suture loop.

FIG. 5B shows an embodiment of the suture loop 550. In one embodiment, there is one suture loop. In other embodiments, there can be two or more suture loops. In the embodiment spreader shown in FIGS. 1A-1E, there is one suture loop 550. The suture loop 550 is knotted 350 at the end extending through the axial bore of the spreader 300 and therefore the suture 550 is not slidable through the inner tube 500. In other embodiments, the suture loop may be slidable.

Figure 6:
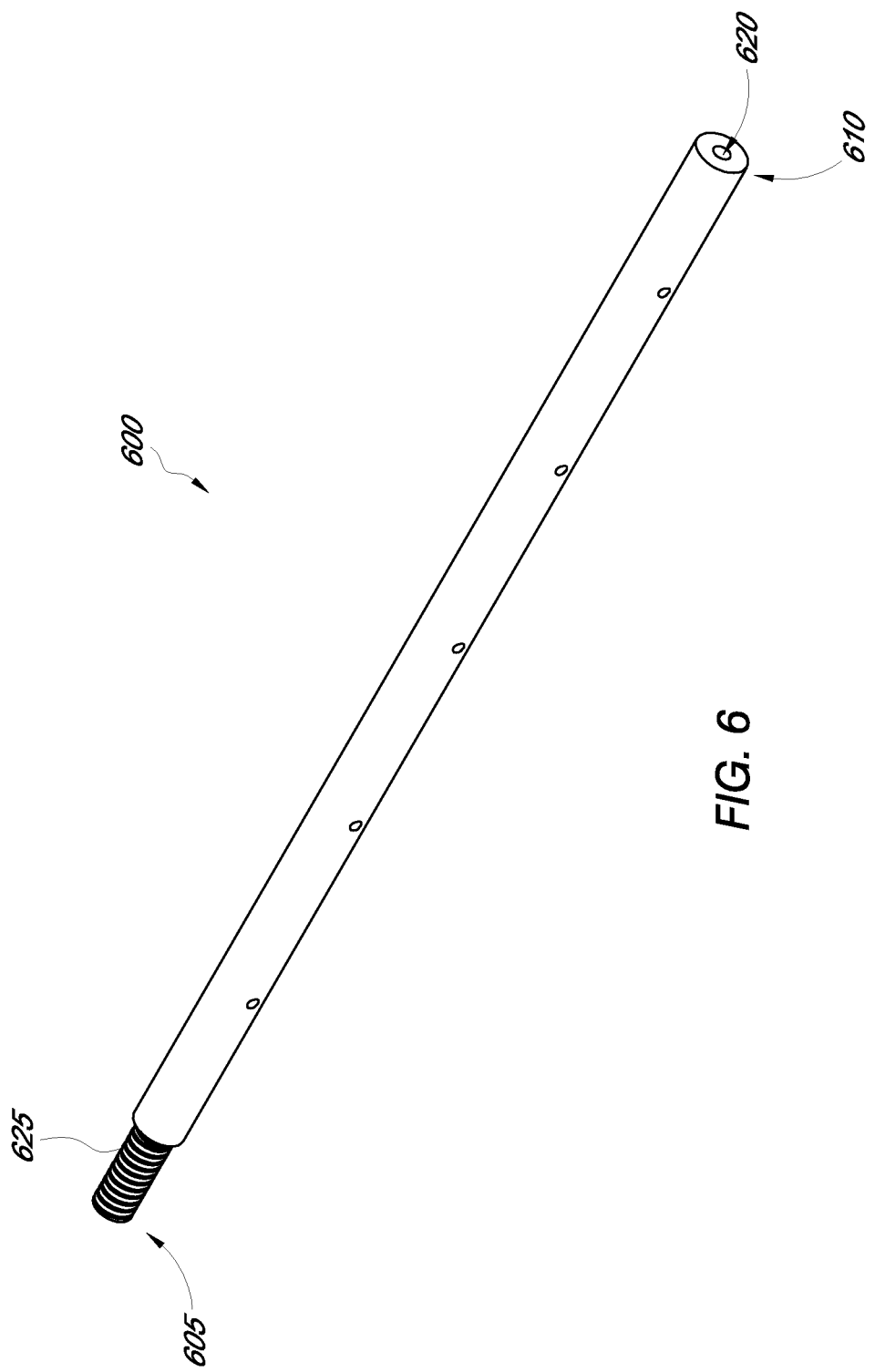
FIG. 6 shows a perspective view of one embodiment of an outer tube component of an insertion tool.

FIG. 6 shows an embodiment of the outer tube 600. The outer tube 600 is attached at its proximal end 605 to the distal end of handle 700 via threading 625. The distal end 610 of the outer tube 600 is configured such that the inner tube 500 is drawn into the outer tube 600 and through the distal end 610 of outer tube 600 where it is secured to the spreader 300. When the inner tube 500 is advanced far enough that the spreader 300 locks into place or cannot advance anymore, the outer tube 600 is surface 225 to surface 620 with the anchor body 200 so that when the anchor body 200 reaches the distal end of the outer tube 600, the inner tube 500 cannot advance any further and the continued rotation of the deployment knob and advancement of the actuator shaft and inner tube 500 strips the threading from the spreader 300 and the inner tube breaks off.

Figure 7A:
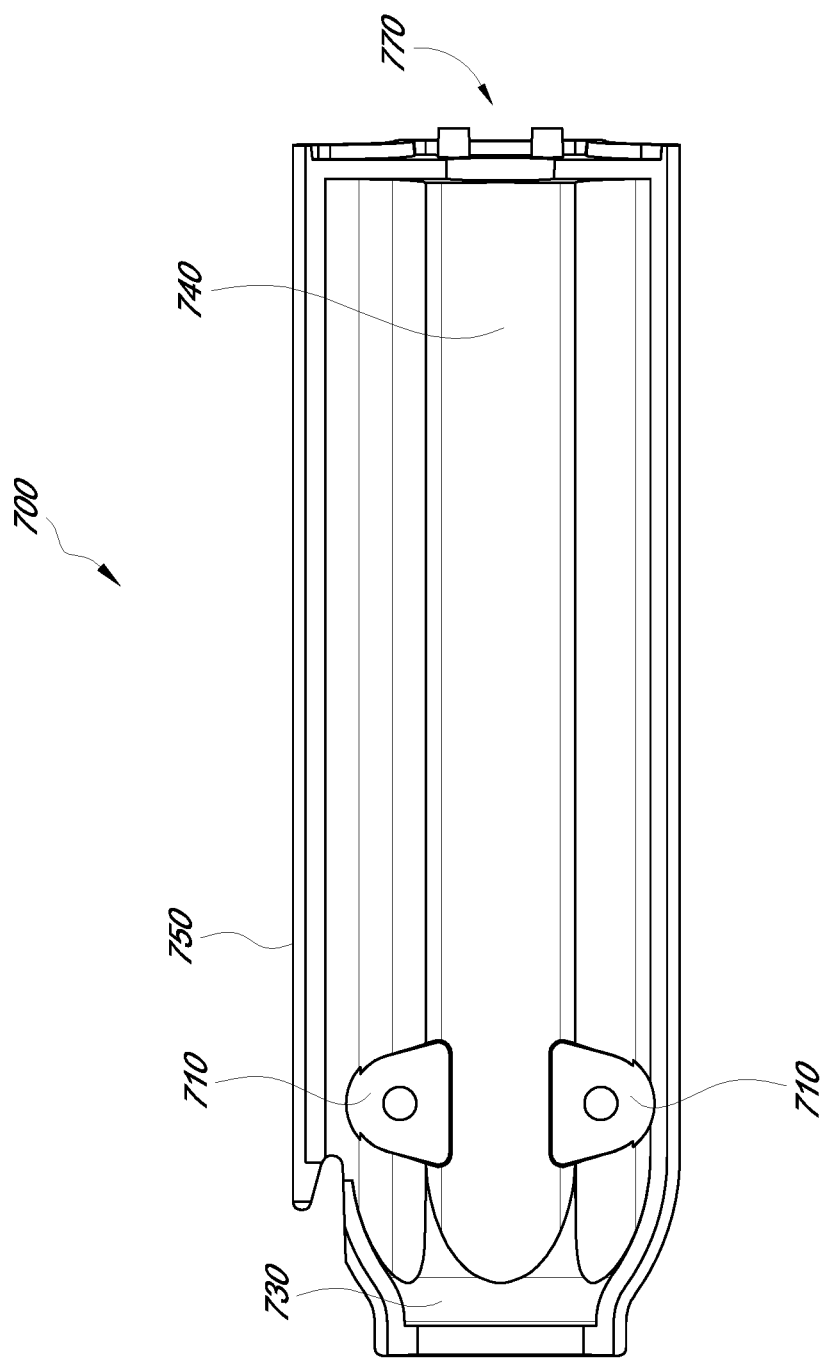
FIG. 7A shows a side view of one embodiment of a handle component of an insertion tool.
Figure 7B:
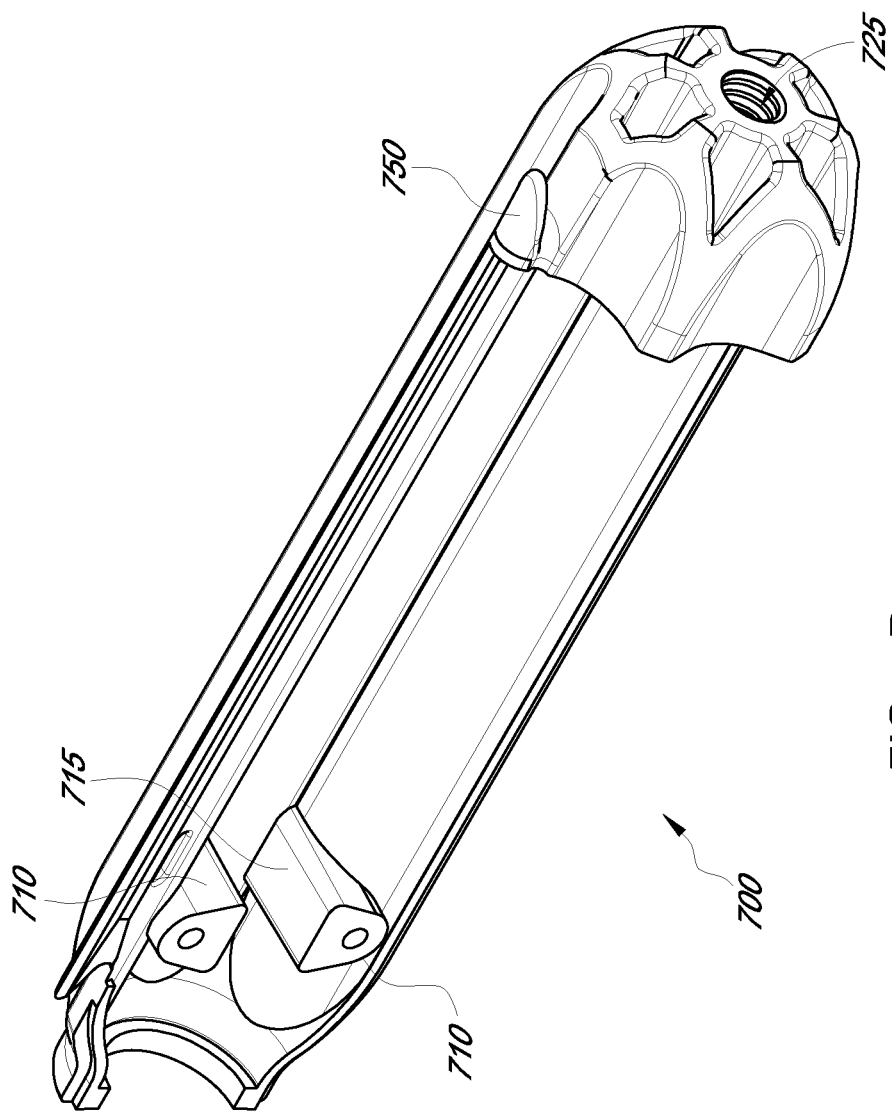
FIG. 7B shows a perspective view of one embodiment of a handle component of an insertion tool.

FIGS. 7A and 7B show embodiments of a handle body 700. FIG. 7A is a cut-away view of the handle body 700. The proximal end of the handle 700 is configured to receive the deployment knob 900 via the ridges 730 which hold the knob 900 secure. The actuator shaft 800 is housed within the handle body 700. A set of flat brackets or braces 710 secure the actuator shaft 800 within the handle 700. The distal end 770 of the handle is configured to receive the outer tube 600 via threads 625. The outer tube 600 is permanently affixed to the handle 700.

FIG. 7B depicts a cross-sectional view of one embodiment of a handle 700. In FIG. 7B the flat surface 715 of the bracket 710 is shown.

Handle 700 also comprises an aperture for passing sutures through the handle 700 and a cleat 750 for containing the sutures 550. The cleat 750 secures the suture that runs from the anchor from unraveling, moving or advancing through the inner tube 500.

Figure 8:
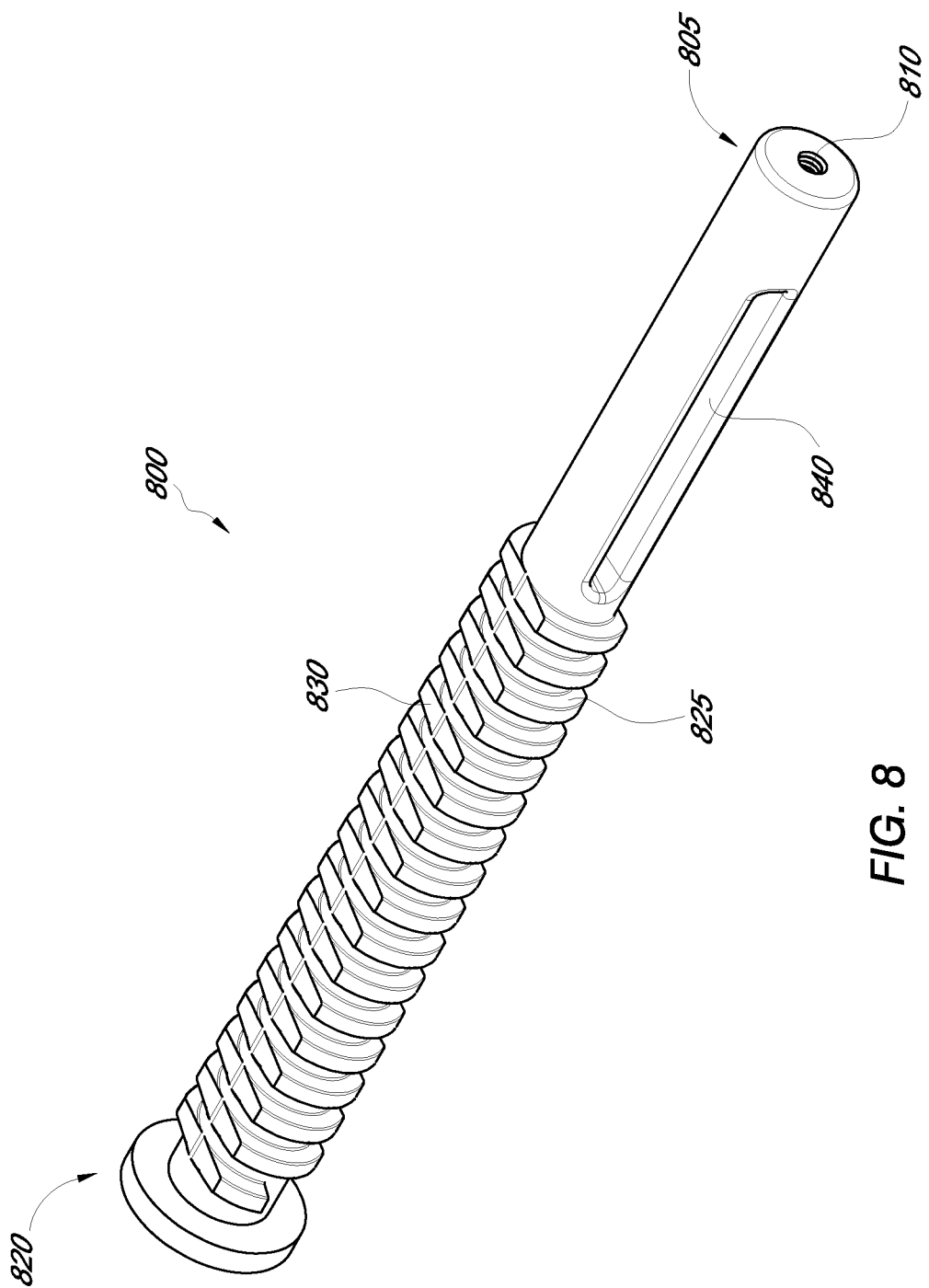
FIG. 8 shows one embodiment of an actuator shaft component of an insertion tool.

FIG. 8 depicts the threaded actuator shaft 800. The actuator shaft 800 is comprised of a distal end 805 comprising a threaded hole 810 which is configured to receive the inner tube 500, a second threaded portion 825 on the body of the shaft configured to advance the inner tube 500, and a proximal end 820 configured to secure within the deployment knob 900. The threading 825 of the actuator 800 has two flat areas 830, one on each side, where there is no threading. These flat areas 830 fit within the flat brackets 710 of the handle such that the actuator 800 cannot rotate within the handle, but can only advance through the handle while also advancing the inner tube 500.

The body of the actuator shaft 800 is configured with threading 825 to permit the shaft 800 to advance the inner tube 500. The body of the actuator shaft 800 is not perfectly round, but rather is oval shaped with flat sides 830 that are fit into the handle body in such a way that the actuator shaft 800 cannot itself rotate when the deployment knob 900 is turned and the shaft 800 advances via the knob 900. Thus, the threads do not go all the way around the shaft but rather flatten out on the flattened sides of the shaft. The actuator shaft is configured as a coaxial system. That is, the spreader 300, inner tube 500 and actuator 800 are configured to operate as one piece. The flat brackets 710 in the handle make the actuator shaft 800 stay on plane such that the actuator shaft 800 itself cannot rotate within the handle 700. The proximal end of the inner tube 500 couples with the distal end of the actuator shaft 800 via threading.

The sutures 550 are threaded through the inner tube 500 and exit the inner tube at its proximal end. When the sutures 550 exit the inner tube 500 they are within the actuator shaft 800 and exit the actuator shaft 800 at an aperture 850 and are threaded through a second aperture 770 in the handle body 700 and then are wound around a cleat 750 on the outside surface of the handle body 700.

Figure 9:
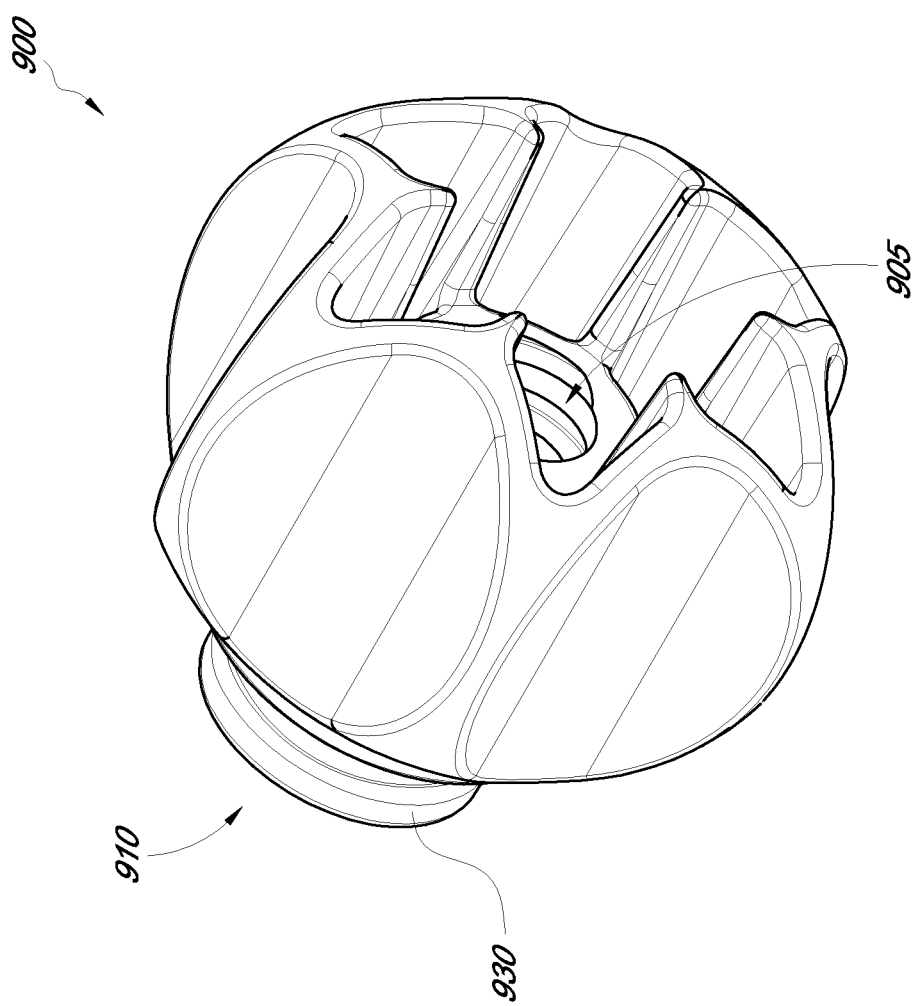
FIG. 9 shows one embodiment of a deployment knob component of an insertion tool.

Moving to FIG. 9, a deployment knob 900 is shown. The deployment knob 900 comprises an axial bore 910 which is configured with threading 905, and a groove 930 configured to be received by a corresponding ridge 730 of the handle 700. The threading 905 in the axial bore 910 is configured to receive the actuator shaft 800. The deployment knob 900 is configured to advance, relative to the deployment knob 900, the inner tube 500 via the actuator shaft 800. The actuator shaft 800 is joined at its proximal end to the distal end of the deployment knob 900 via threading 905 in the axial bore 910. The actuator shaft 800 is attached to the inner tube 500 by way of the proximal end of the inner tube 500 advancing into the distal end of the actuator shaft via threading so that when the deployment knob 900 is rotated, the mechanism of the shaft 800 advances the inner tube 500 proximally such that the spreader 300 is then advanced into the anchor body 200 to expand the anchor body 200 into bone and secure it in place. As the deployment handle is turned, the actuator shaft 800 is advanced in a proximal direction until the anchor body 200 is deployed and locked into place.

Figure 10:
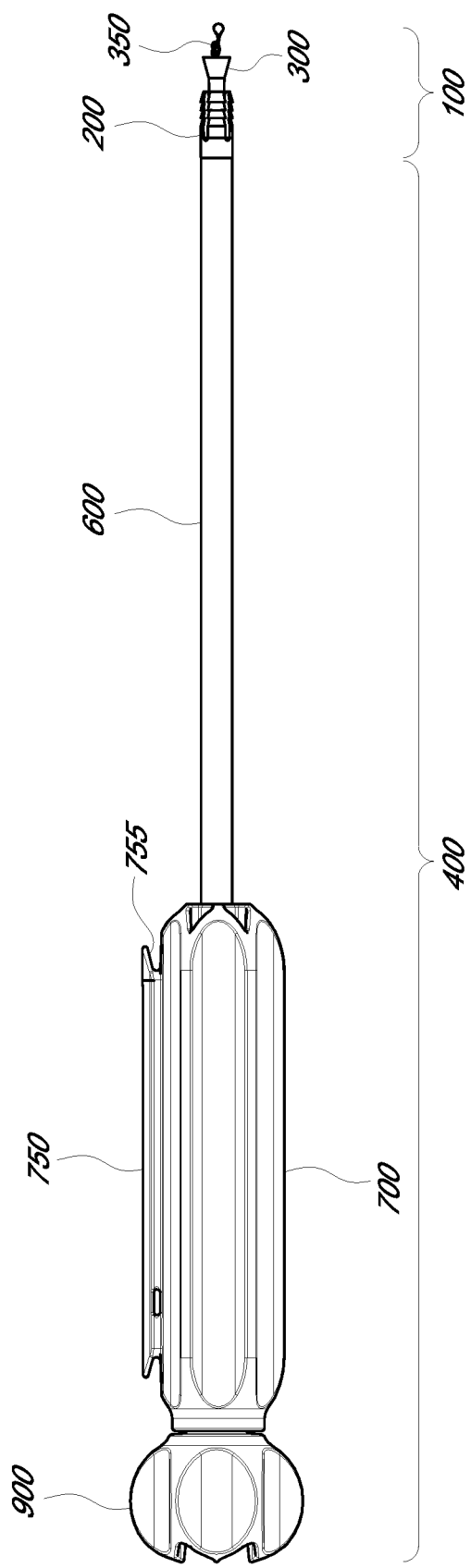
FIG. 10 shows the coupled inserter tool and suture anchor device in an unexpanded or undeployed state.

FIG. 10 shows a suture anchor 100 coupled to the inserter tool 400. The suture anchor 100 comprises the anchor body 200 and the spreader 300. The inserter tool 400, as shown, depicts the outer tube 600, the handle 800 and the deployment knob 900. The inner tube 500 (not shown) is positioned within the outer tube 600, and the outer tube is flush with the anchor body 200. The outer tube 600 may hold the anchor body 200 steady during insertion and deployment. The inner tube 500 extends through the anchor body 200 and couples with the spreader 300 via threading. The spreader 300 is configured to be pulled through the distal end of the anchor body 200 by the inner tube 500 via rotation of the deployment knob 900. The suture loop 550 is knotted 350 at the end of the spreader 300.

The inner tube 500 provides the mechanism to draw the spreader 300 into the axial bore 225 in the anchor body 200 to fully expand the anchor body 200. During deployment of the tissue capture anchor 100, the inner tube 500 is continually advanced via a screwing motion of the knob 900 until the spreader locks with the anchor body. As the deployment knob 900 continues to turn and the inner tube 500 continues to pull on the threads of the spreader 300, the inner tube 500 strips the threads from the inside of the spreader 300 and the insertion tool 400 snaps off at just below the base of the anchor body 200. Any thread shavings are contained within the outer tube 600. Alternatively, the inner tube 500 may be disengaged from the spreader by un-screwing the inserter from the anchor (for example, by rotating the entire inserter relative to the anchor).

Additional Embodiments of the Spreader

Figure 11A:
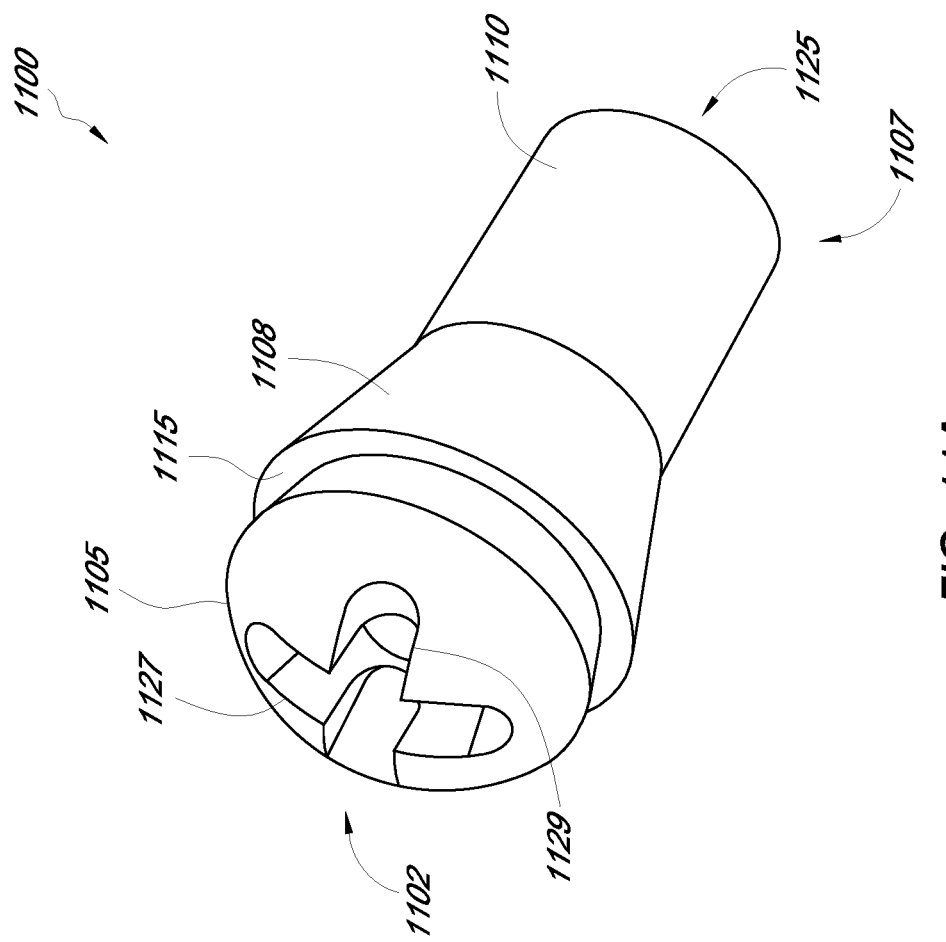
FIG. 11A shows a perspective view of an alternate embodiment of a spreader.
Figure 11B:
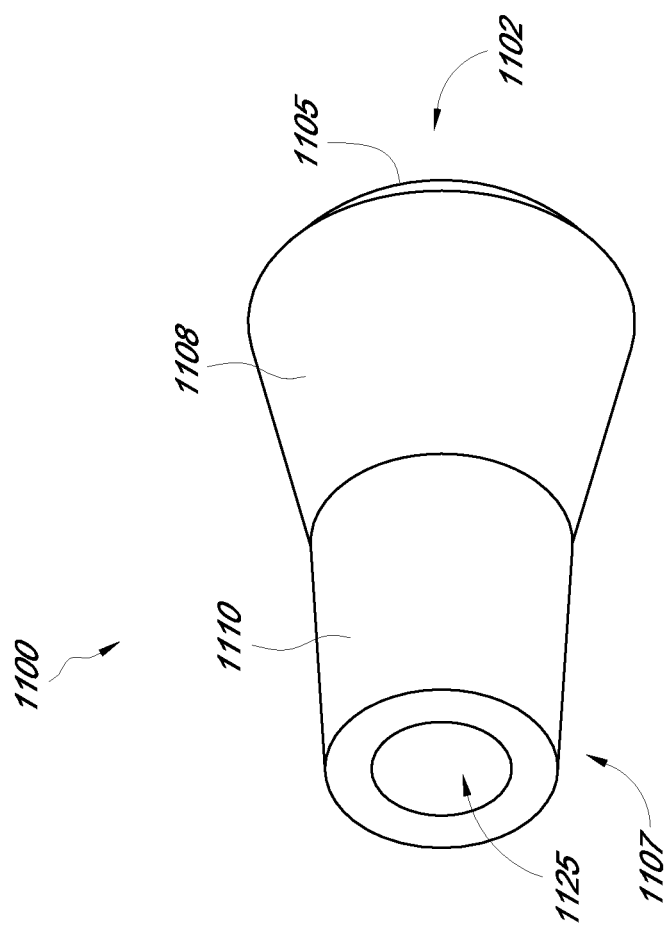
FIG. 11B shows another perspective view of an alternate embodiment of a spreader.
Figure 11C:
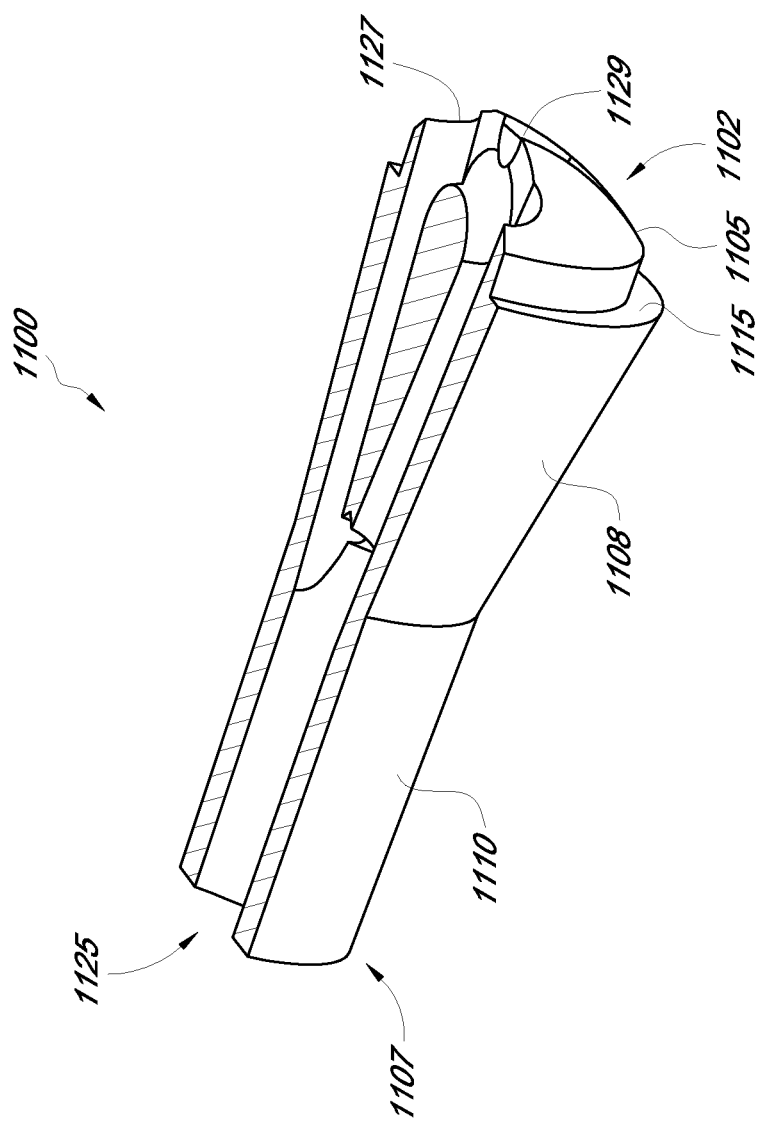
FIG. 11C shows a cross-sectional view of an alternate embodiment of a spreader.
Figure 11D:
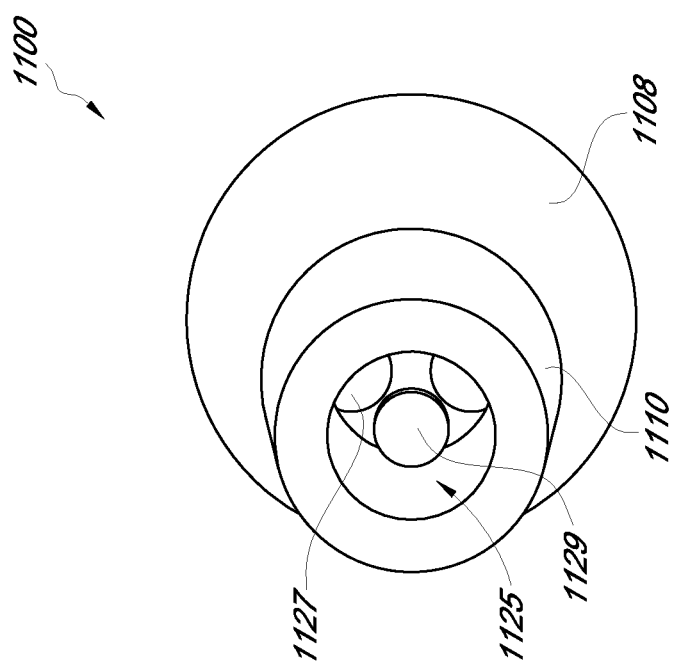
FIG. 11D shows a perspective end view of an alternate embodiment of a spreader.
Figure 11E:
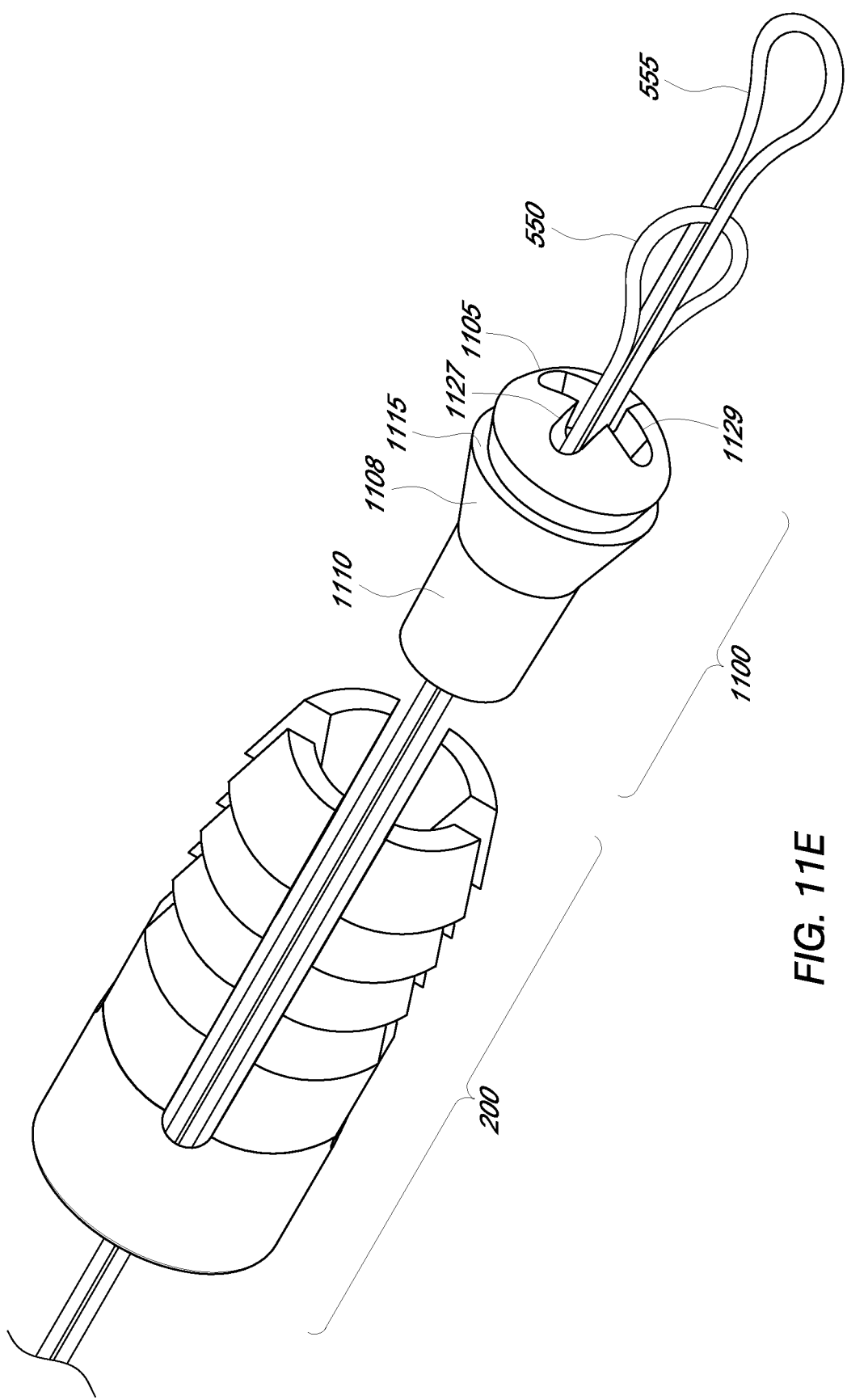
FIG. 11E shows a perspective exploded view of one embodiment of a suture anchor having an alternate spreader in an undeployed or unexpanded state.
Figure 11F:
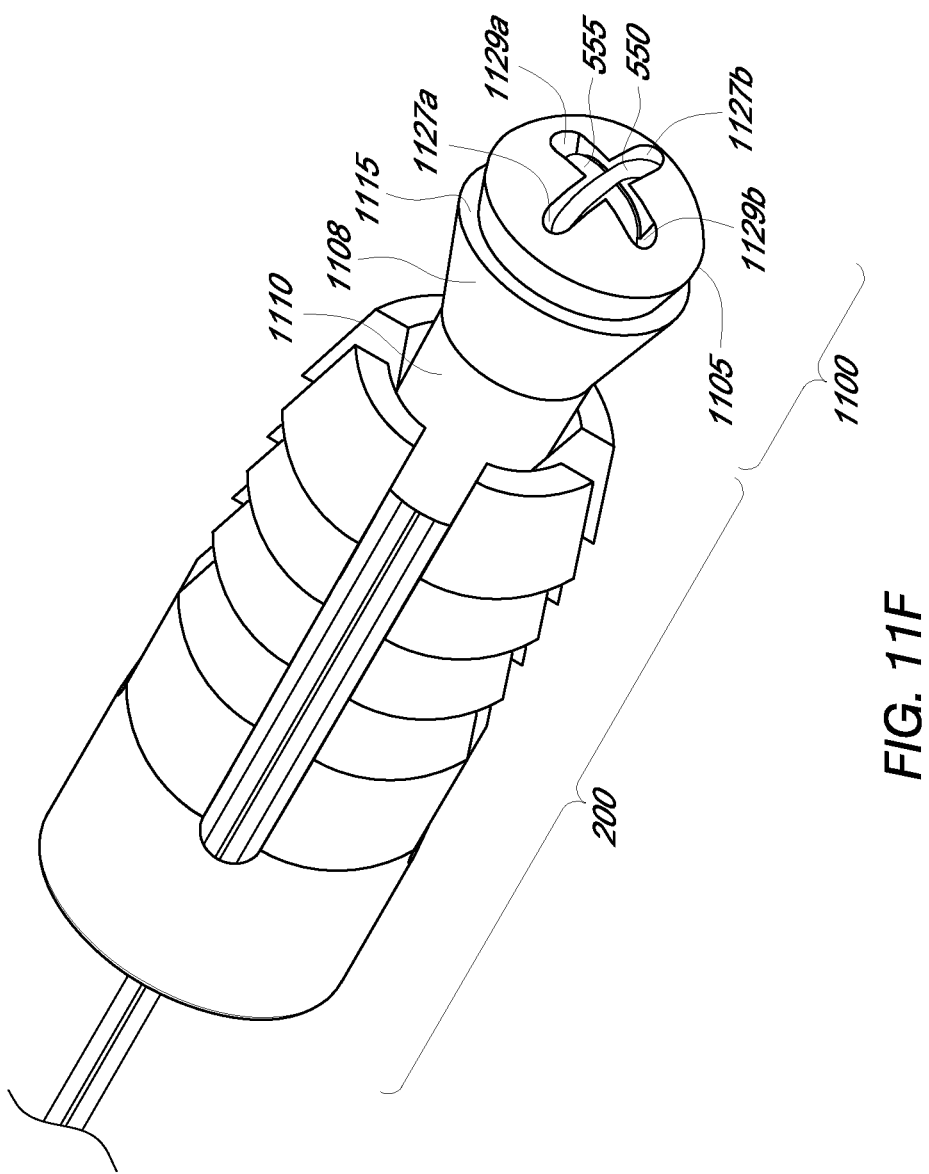
FIG. 11F shows a perspective view of one embodiment of a suture anchor having an alternate embodiment of the spreader wherein the spreader is partially inserted into the bone anchor.
Figure 11G:
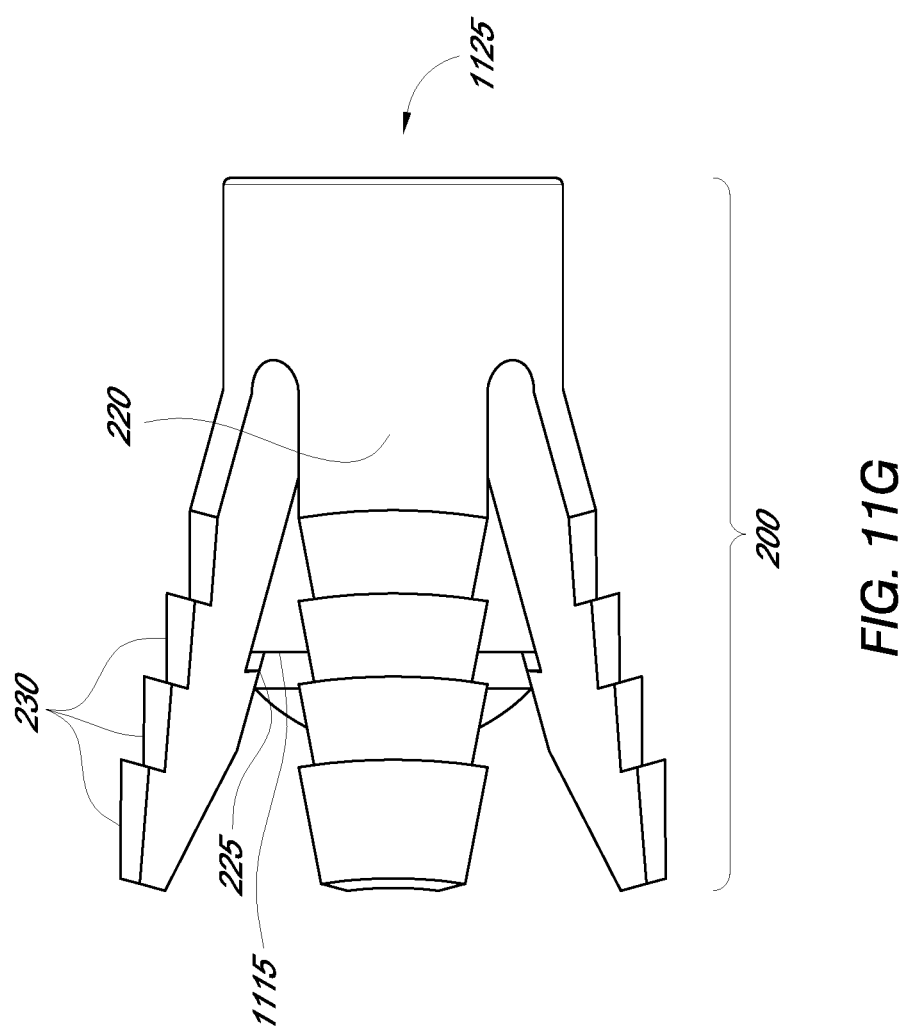
FIG. 11G shows a side view of one embodiment of a suture anchor having an alternate embodiment of the spreader in the deployed or expanded state.
Figure 11H:
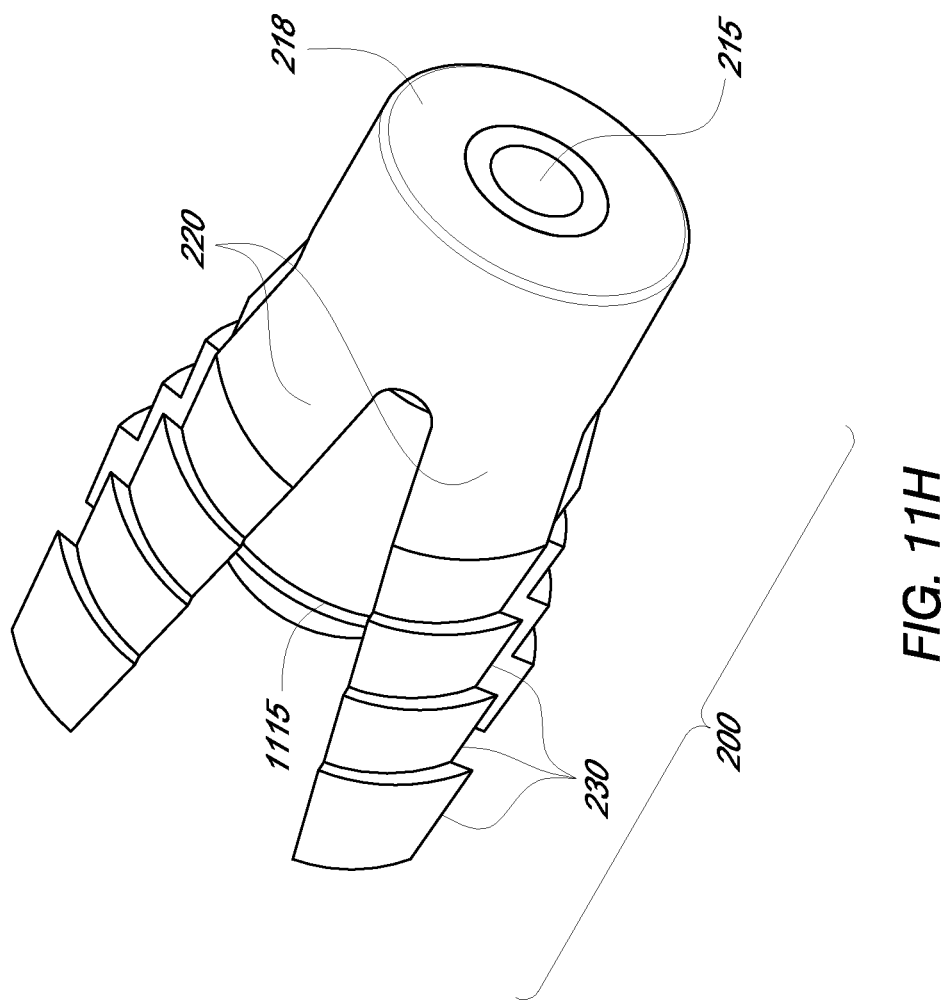
FIG. 11H shows a perspective view of one embodiment of a suture anchor having an alternate embodiment of the spreader in the deployed or expanded state.
Figure 11I:
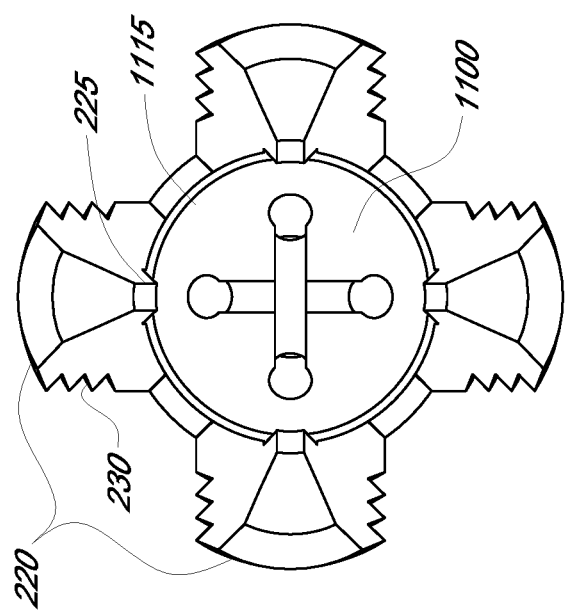
FIG. 11I shows an end view of one embodiment of a suture anchor having an alternate embodiment of the spreader in the deployed or expanded state.
Figure 11J:
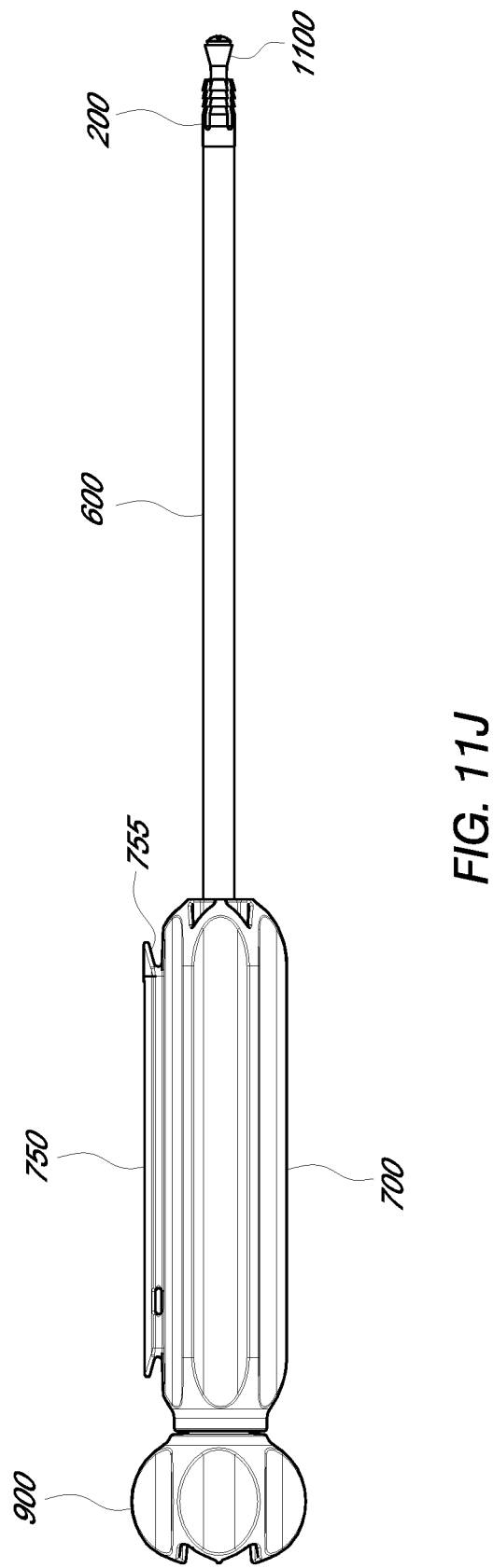
FIG. 11J shows a side view of one embodiment of a suture anchor having an alternate embodiment of the spreader coupled to an insertion tool.

FIGS. 11A-11J depict an alternate embodiment of the spreader 1100. FIG. 11A shows front or distal perspective view of an embodiment of the spreader 1100. FIG. 11B shows a back, or proximal perspective view of the spreader 1100. FIG. 11C shows a cross-sectional view of the spreader 1100. FIG. 11D shows a proximal perspective view of the spreader 1100. FIG. 11E shows a perspective view of the spreader 1100 with the anchor body 200, and sutures 550 and 555. FIG. 11F shows a perspective view of the spreader 1100 engaged with the anchor body 200 but not fully deployed. FIG. 11G shows a side view of the spreader 1100 engaged with the bone anchor 200 in the fully deployed position. FIG. 11H shows a proximal perspective view of the spreader 1100 and bone anchor 200 fully expanded. FIG. 11I depicts a front full view of the spreader. FIG. 11J shows this alternate embodiment of the spreader 1100 engaged with the insertion tool 400.

The spreader 1100 comprises a generally tube-shaped base section 1110 at the proximal end 1107 which joins with the gradually expanding upper end 1108 of the spreader 1100. The proximal end 1107 further comprises an axial bore 1125 for receiving sutures 550 and 555 and for receiving an insertion tool 400, a generally conical shaped spreader at the distal end 1102 which is wider than at the proximal end, and an optional ridge 1115 at the tip of the distal end for securing the spreader 1100 within the bone anchor 200. The generally cylindrical-shaped or cone-shaped upper end 1108 gradually widens in a conical shape from the proximal end of the base section 1110 to the distal end of the upper end 1108 of the spreader 1100. The distal end of the spreader 1100 comprises a rounded tip area 1105 through which suture channels 1127 and 1129 extend.

The distal end 1102 comprises a rounded area 1105 around channels 1127 and 1129 which are configured to receive sliding sutures 550 and 555. The channels 1127 and 1129 open into axial bore 1125. The channels 1127 and 1129 are configured such that the sutures 550 and 555 are arranged in a cross shape and are freely slidable through the spreader and the inner tube and in the hands of the surgeon. As can be seen in FIG. 11C, the channels 1127 and 1129 of the axial bore 1125 allow for two distinct suture loops to be threaded through the spreader 1100. The arrangement provides for four suture limbs extending through the axial bore 1125 and available for use by the surgeon. The sutures are slidable relative to the spreader such that when the surgeon pulls on one suture limb, the corresponding limb on the other side of the loop will be shortened. In one embodiment, the distal end may also comprise a ridge 1115, which may be slightly undercut 1122 resulting in a stronger hold in the bone when then the anchor is fully deployed.

As further shown in FIGS. 11C, 11D, 11E and 11F, the spreader 1100 comprises channels 1129 and 1127 for receiving the sutures 550 and 555. The channels 1127 and 1129 are arranged in a cross shaped pattern, that is with one channel being perpendicular to the other and one channel being deeper (i.e., more proximal) than the other channel. This arrangement prevents one suture 550 from touching the other suture 555 allowing the two sutures to slide independently without interference. FIG. 11D shows the spreader 1100 from the proximal end 1107 and illustrates how the axial bore 1125 feeds the two channels 1127 and 1129. FIG. 11E shows the spreader 1100 loaded with sutures 550 and 555 and additionally illustrates the two suture loops extending from the channels 1127 and 1129.

The proximal end 1107 is configured for receiving sutures 550 and 555 and coupling the spreader 1100 with an inserter. For instance, in this embodiment, the proximal end 1107 of the spreader 1100 comprises a hole 1125 that receives the inserter tool for coupling with the anchor body 200.

As described above and depicted in FIG. 11F, the distal end of the spreader 1100 comprises channels 1127a,b and 1129a,b opening to the axial bore 1125 through which the sutures 550 and 555 extend. The sutures 550, 555 each are threaded through the proximal end of the spreader 1100, through the axial bore 1125 and then each into one of the channels 1127a and 1129a. The sutures 550 and 555 extend out of each channel at the distal end of the spreader 1100 and are looped back through the spreader 1100 into its corresponding channel 1127b and 1129b and through the proximal end of the spreader 1100. The sutures 550 and 555 are configured to freely slide.

The spreader 1100 is configured to be drawn through the distal end of the anchor body 200 via an insertion tool 400. FIG. 11F illustrates the anchor body 200 partially engaged with the spreader 1100. As the suture anchor 100 is deployed, the spreader 1100 is further advanced into the anchor body 200, spreading the tines 220 of the anchor body 200 until the ridge 1115 of the spreader 1100 engages the groove 225 in the inside of the anchor body 200 at which point it locks into place. In one embodiment, the ridge 1115 is undercut 1122 providing even more security against reversing. Other locking mechanisms may be employed. A fully deployed spreader 1100 and anchor body 200 is depicted in FIG. 11G and FIG. 11H while FIG. 11I illustrates a face view of the fully deployed spreader 100 and anchor body 200.

As discussed above, the tines in the anchor may be in a low-profile streamlined position prior to insertion into bone. A spreader 1100 may be used after insertion to expand the tines such that their teeth 225 engage bone. The spreader 1100 may comprise any suitable shape configured to be inserted through the axial bore 215 in the anchor body 200 and make contact with the tines 225. The spreader 1100 may be at least partially positioned within the axial bore of the anchor prior to tine expansion as depicted in FIG. 11F. As the spreader 1100 is moved from a first lower position to a second upper position, the proximal end of the spreader 1100 is designed to spread or force the tines 220 from a first low-profile position (for example, an internal lateral position) to a second external lateral position. In one embodiment, the proximal end of the spreader 1100 may have ridges to assist in preventing slippage or mis-alignment.

The spreader 1100 will remain in the anchor with the tines in their fully spread position. The force provided by the tines' interaction with the bone keeps the spreader 1100 tightly engaged. Further protection against slipping or tilting of the spreader 1100 is provided by the optionally ridged sides of the spreader 1100. In one embodiment, the spreader 1100 may have ridges or indentations to assist in a tight fit such that accidental slipping or adjustments are minimized while deliberate withdrawals are possible after insertion into bone without inadvertent pull-outs. In one embodiment, one or more of the tines 220 have an indentation on a side facing the central axis of the anchor. A ridge on the spreader can then engage the indentation, thereby stabilizing the spreader 1100 and preventing the spreader 1100 from being advanced too far into the anchor. In an alternative embodiment, the spreader comprises an indentation (for example, an indentation in a ridge on the spreader 1100) that can engage with a protrusion on a side of a tine facing the central axis of the anchor. In addition, to stabilizing the spreader 1100 and preventing over insertion, this feature also prevents rotation of the spreader 1100 relative to the anchor.

FIG. 11J shows the alternative spreader 1100 and bone anchor 200 coupled with the loaded, assembled insertion tool 400. The sutures 550 and 555 (not shown in FIG. 11J) extend from the proximal end of the spreader 1100 and through the inner tube 500 (not shown) which is situated inside of the outer tube 600. In one embodiment, the insertion tool is the same as described above. That is, the sutures exit the inner tube 500 at its proximal end, which is engaged with the distal end of the actuator shaft 800 (not shown). The sutures exit the actuator shaft 800 at openings in the side of the shaft 800 where they exit the handle 700 at an aperture 770. The handle 700 comprises a cleat 750 for maintaining the lengths of suture loop.

Alternative Bone Anchor Embodiments

1. Alternative Locking Mechanism

Figure 12A:
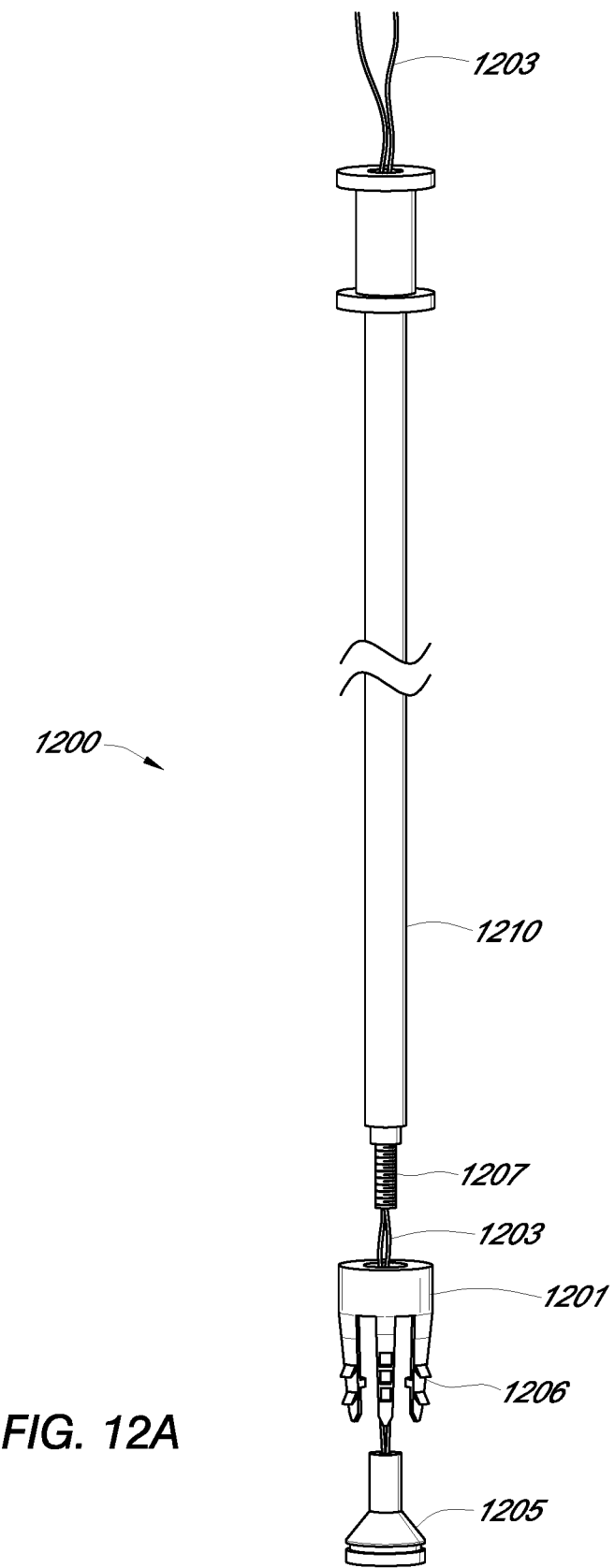
FIGS. 12A-12D depict an alternative embodiment of the anchor and insertion tool using a pull-through instead of a push-through motion.
Figure 12B:
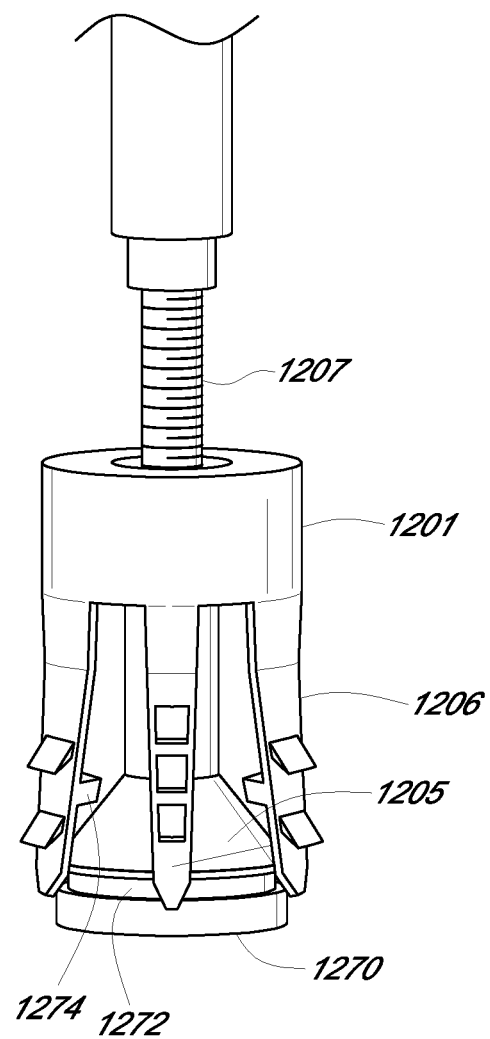

In one alternative embodiment depicted in FIGS. 12A-12D, the anchor body and spreader are similar to those described above, except that the spreader comprises the locking groove and the anchor body comprises protrusions to interface with the groove. FIG. 12A is an exploded view depicting the inserter tool and anchor with the spreader outside of the anchor body. As above, the anchor body 1201 is configured such that the spreader 1205 is inserted into the anchor body 1201 through the space between the tines in the distal portion of the anchor body 1201. In some embodiments, the spreader piece 1205 has pre-attached sutures 1203. The suture passes through the interior of the anchor inserter tool 1200. In some embodiments, the suture 1203 passes through the inserter tool 1200 and then out the top of the inserter for manual manipulation by a surgeon. In other embodiments, the suture 1203 is engaged with a pulling mechanism in the handle portion of the inserter. For example, the suture 1203 may be coupled to a reel or lever system that can pull up on the suture. Sutures may be fixed to the spreader 1205 or free running.

The inserter tool 1200 depicted in FIG. 12A is made of a rigid material and can be hollow. The inserter tool 1200 can comprise at least two concentric tubes. The inner tube 1207 is reversible coupled to the spreader 1205 such as by external threads engaging with corresponding internal threads in the spreader 1205. An outer tube 1210 can be used to interface with the anchor body 1201 and provide a distal anchor insertion force as well is keeping the anchor within the bone when a proximal pulling force is applied to the spreader 1205 by the inner tube 1207. The outer tube 1210 may comprise a shoulder or stopper piece (for example, FIG. 22 element 2205) at its distal end so that distal force may be provided by the inserter tool 1210 to the top of the anchor 1201 and to prevent the anchor 1201 from progressing too far upwards along the inserter tool 1200. During insertion of the anchor 1201, the spreader is positioned between distal ends of the tines 1206 as in FIG. 12B, with the spreader 1205 distal enough that the tines 1206 are not expanded. After insertion of the two components, the inner tube is pulled by the surgeon to force the spreader 1205 proximally and thereby expand the tines 1206. The inner tube is either unscrewed or deliberately broken away (such as by stripping of threads between the inner tube 1207 and the spreader 1205) to remove the inserter tool from the anchor. Where the inner tube 1207 is unscrewed from the spreader 1205, protrusions and corresponding indentations may be provided between the spreader 1205 and one or more tines 1206 to prevent rotation of the spreader 1205. Such a rotation prevention feature may not be required if the inner tube 1207 is detached by breaking away from the spreader 1205. The proximal pulling of the inner tube 1207 may be effected by either sliding the inner tube 1207 relative to the outer tube 1210 or by rotation with corresponding threads between the inner tube 1207 and the inside of the outer tube 1210 or other fixed portion of the inserter. Alternatively, the inserter described above with respect to FIGS. 4-10 may be used.

Figure 12C:
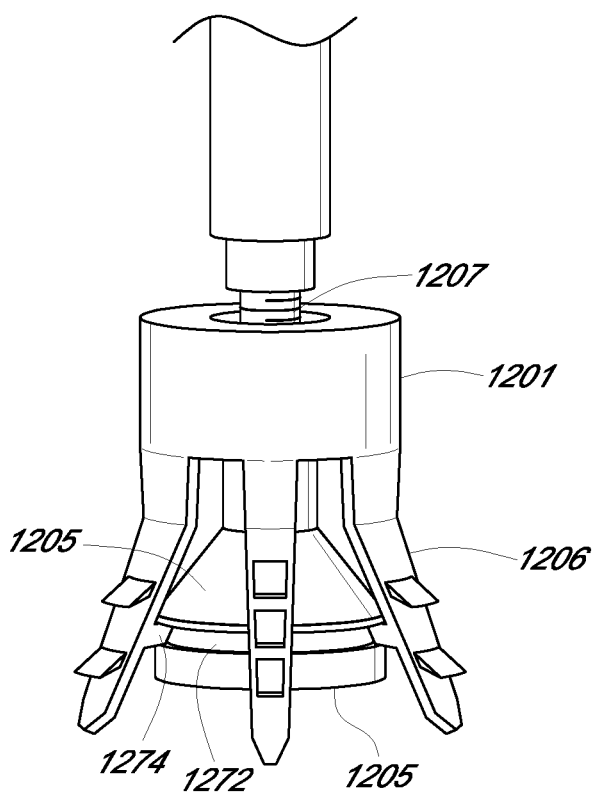
Figure 12D:
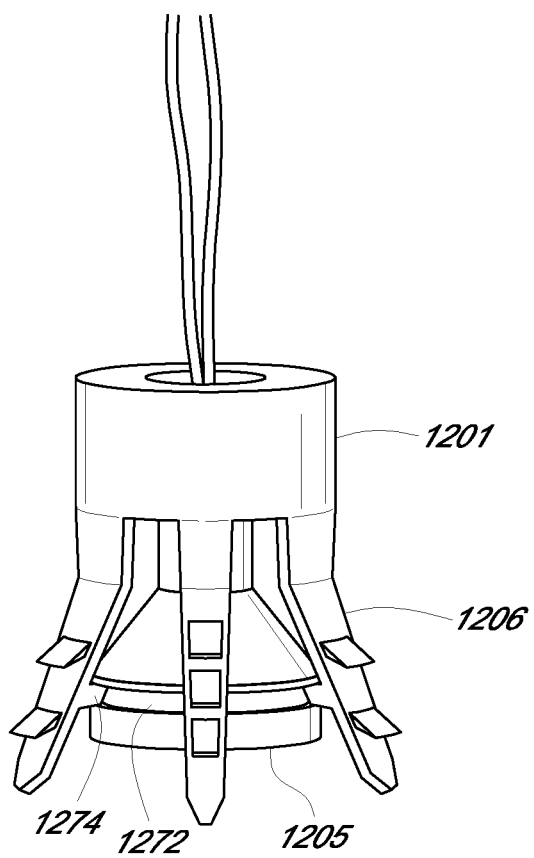

FIG. 12C depicts the fully engaged expanded anchor 1201 and FIG. 12D depicts the fully expanded anchor 1201 with the inserter tool removed and the suture 1203 remaining. As in the previous embodiments, the spreader 1205 will remain permanently located in the anchor 1201 to help prevent collapse, movement or slipping of the components and of the anchor 1201 as a whole. In one embodiment, illustrated in FIGS. 12B, 12C and 12D, protrusions 1274 are provided on the inside of the tines 1206 configured to snap into a groove 1272 located on the spreader 1205 when the tines 1206 are fully deployed. This feature provides improved stability of the spreader 1205.

2. Alternative Tine Configuration

Figure 13A:
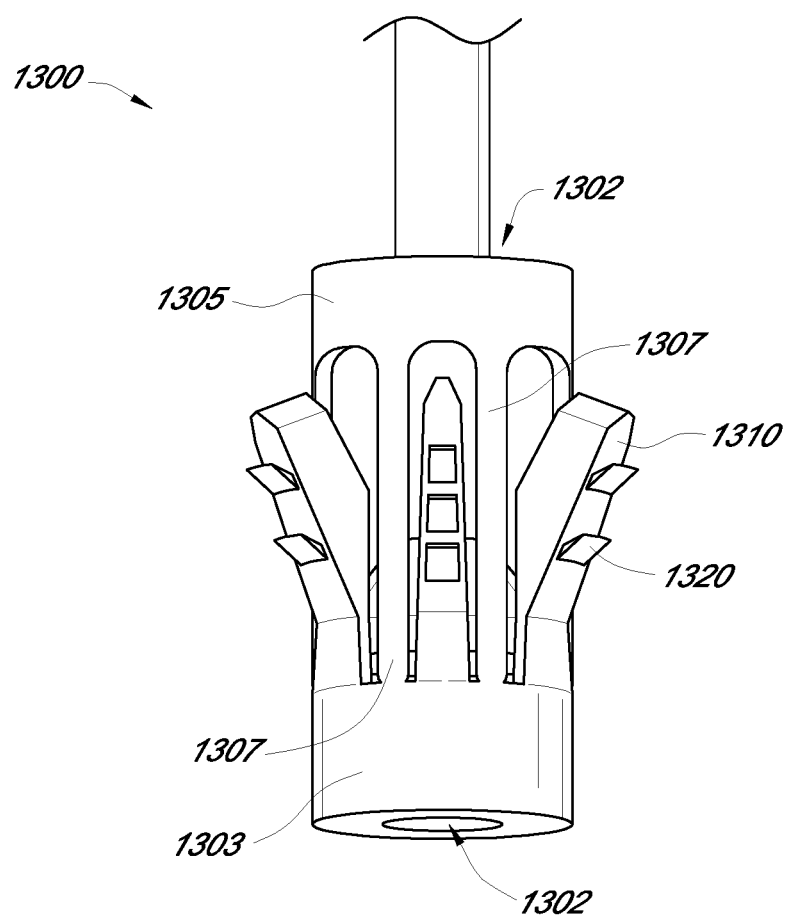
FIGS. 13A and 13B depict an alternative embodiment of the anchor and spreader in which the tines expand from the proximal end of the anchor.
Figure 13B:
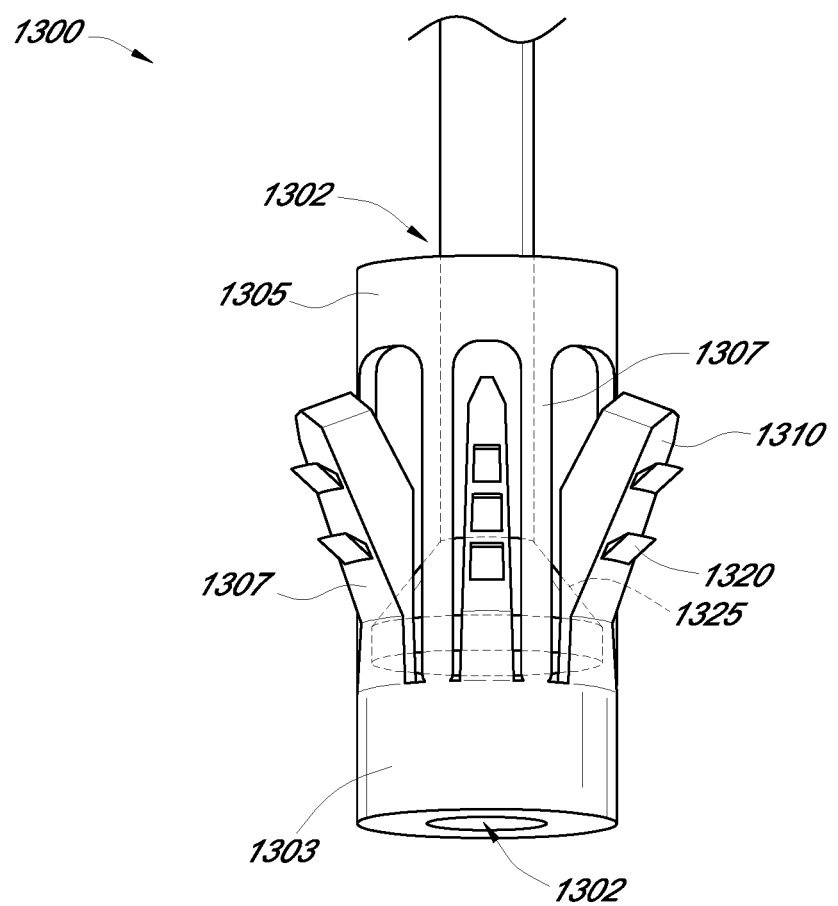

Another alternative embodiment is depicted in FIGS. 13A and 13B. In FIG. 13A, an anchor 1300 comprises an anchor body comprising a proximal portion 1305 and a distal portion 1303. the anchor body also comprises an axial bore 1302, anchor support legs 1307, tines 1310, and teeth 1320. The anchor further comprises a spreader 1325. This embodiment also comprises ridges, sutures, an insertion tool, spreader notch and tines groove, (not shown in FIG. 13) similar to that depicted in FIG. 12. In this embodiment, a spreader 1325 is initially positioned distally from the anchor and the tines expand in the proximal end rather than the distal end of the anchor. In FIG. 13B, the spreader is positioned within the distal portion 1303.

The anchor body 1305 comprises an axial bore 1302 and support legs 1307. The anchor body 1305 couples with the lower anchor 1303 such that the support legs 1307 fit alternately with the tines 1310 In this embodiment, the anchor 1300 is configured such that the spreader 1325 is inserted into the anchor body through the axial bore in the distal portion 1303 and into the space between the tines of the anchor 1300. As the spreader 1325 is deployed, the reverse taper of the tines cause the tines to expand from the distal end outward towards the proximal end and engage the bone. The expanded tines 1310 rest below undrilled portions of the bone cortex, thereby preventing the spreader 1325 from being pulled out. The use of teeth 1320 in the tines 1310 is therefore optional. The spreader 1325 can have pre-attached sutures, which may be used to secure soft tissue. The suture passes through a hollow tube of the insertion tool 1335 and then out of the top of the insertion tool 1335 for manual manipulation by a surgeon. An anchor insertion tool such as described above may be used to insert the anchor, deploy the spreader, and detach the insertion tool thereby leaving suture strands attached to the anchor 1350. Once fully expanded, a notch 1340 in the spreader engages a groove 1345 in the tines and becomes locked so that the spreader does not slip or reverse itself (as shown in FIG. 12). Alternatively, a ridge on the spreader may interface with a groove in the anchor body.

The distal end of anchor 1300 comprises tines 1310 extending upwards from the distal end of the anchor. The tines 1310 comprise teeth 1320, as previously described. The tines 1310 are narrower at their distal ends and gradually wider in a lateral direction at their proximal ends such that the inside surface of the tines tapers from its widest at the proximal end to the narrowest at the distal end. The distal end of the anchor comprises an axial bore. The spreader 1325 initially rests within the axial bore of the distal portion of the anchor body The anchors depicted in FIGS. 12 and 13 can be made of biocompatible or physiologically inert materials. Such materials include titanium and its alloys, stainless steel, and cobalt based alloys. Bioabsorbable materials can also be used. In some embodiments plastics such as polyetheretherketone (PEEK) or other suitable materials may be used.

The exact size and dimensions of the anchor can vary with its intended use and the patient size. The following overall dimensions are suited for the shoulder and knee joints of an adult human of average size, and can be modified for specific patients or uses. The diameter of the anchor can have, but is not limited to, a range from 3 to 10 mm.

3. Proximal Spreader Alternatives

In the following embodiments, the anchor generally comprises an anchor body and a plurality of bendable tines extending distally from the anchor body. However, the spreader is configured to expand the tines by being "pushed" into the anchor body in a distal direction instead of being "pulled" in the anchor body as in the embodiments described above. The tines may comprise a plurality of teeth. When the bendable tines are expanded (bent outward), the teeth can engage the bone to hold the anchor in place. Some embodiments described herein include suture attachment tabs. In some embodiments, the "push in" embodiment provides the ability to be backed out after installation without further damage to the surrounding tissue or bone, and to retain the tissue by multiple sutures.

Some embodiments provide deformable suture attachment tabs on the anchor that facilitate knotless attachment of sutures to the anchor within the surgical site. In other embodiments, suture may be pre-attached to various locations on the anchor.

Figure 14:
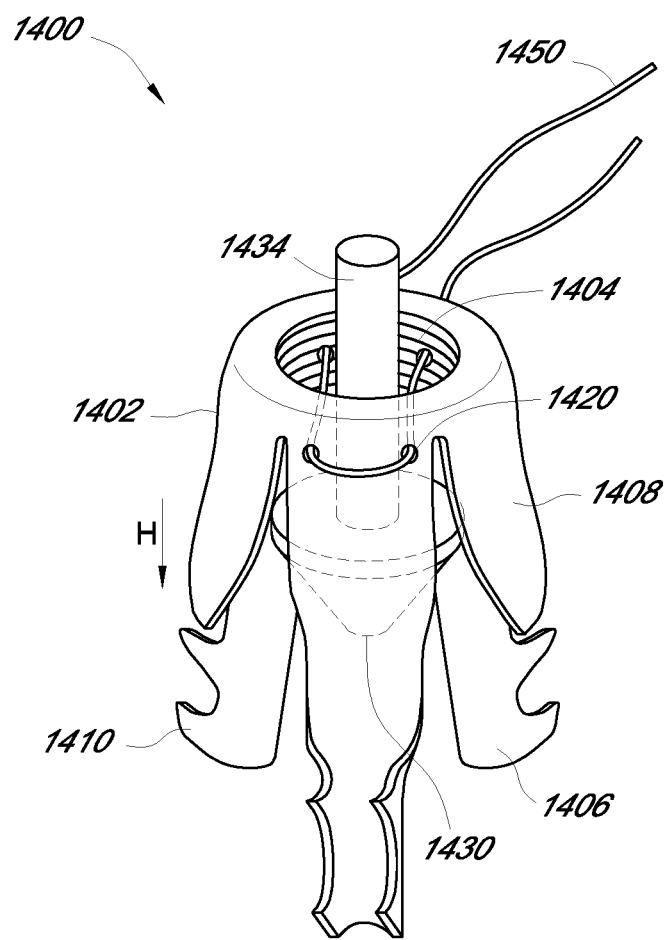
FIG. 14 depicts the anchor with tabs and tines.

FIG. 14 depicts a non-limiting example of an anchor structure 1400 with a proximal spreader configuration. The anchor body 1402 can generally have any shape, for example a circular shape, or a polygon of three or more sides. In the depicted embodiment, the anchor body 1402 has a circular shape with a axial bore 1404, which allows for insertion of a tine spreader 1430, described below. The axial bore 1404 can generally be any shape, for example, a circle shape or a polygon shape. Circular forms are preferred for the axial bore 1404

The distal end of the anchor body 1402 has a plurality of bendable tines 1406 extending therefrom, as shown in FIG. 14. In one embodiment, the anchor body 1402 has from about two to about six bendable tines 1406 extending therefrom. In a preferred embodiment, the anchor body 1402 has three bendable tines 1406 extending therefrom. The bendable tines 1406 may be integrally joined with the anchor body 1402, either by machining or injection molding a uniform piece of material or by stamping of a single sheet of flat material. Alternatively, the tines 1406 may be attached to the anchor body 1402 such as by welding or adhesives. In the depicted embodiment, the tines 1406 are formed by folding of a flat material where the fold is along the longitudinal direction of the tine 1406. Each bendable tine 1406 may comprise, along its outward-facing edge, one or more teeth 1410, preferably three to six in number, which can be engaged with the bone once the tines 1406 are spread apart after insertion of the anchor 1400. Each bendable tine's distal end can be formed to a slant or pointed edge. In other embodiments, the distal end of each bendable tine is either straight or any other effective shape.

The anchor is expandable at its distal end 1407 by the tines 1406 spreading outward. As the bendable tines 1406 are spread apart with the spreader 1430 (described below), the teeth 1410 of the bendable tines 1406 become engaged in bone material such that the anchor is securely attached to the bone. Distal expansion provides improved pull-out strength. Where multiple teeth 1410 are present, they may increase in size as they are positioned more distal from the anchor body 1402. The teeth 1410 are preferably tapered to sharpened points that are able to penetrate tissue and/or the interior matrix (cancellous portion) of the bone. Once expanded, the spreader 1430 remains in the anchor 1400.

The bendable tines 1406 are preferably symmetrically positioned about the anchor body 1402. In some embodiments, when the tines 1406 are in their un-expanded configuration, the distal ends 1407 of the bendable tines 1406 are in a first internal lateral position, as depicted in FIG. 14, such that they are parallel to or angled internal to the longitudinal axis. In one embodiment, the internal angle is from about 8° to about 15°. When in the internal lateral position, the teeth 1410 may be at or within the cylindrical, axially extending region defined by the axial body 1402. During and after insertion of a tine spreader, as the distal ends 1407 of the tines 1406 are moved to their second or external, more lateral position, the distance between the ends 1407 and the longitudinal axis of the anchor 1400 will increase to place the tines at or beyond the cylindrical axially extending region defined by the anchor body 1402.

The anchor body 1402 may also comprise bendable tabs 1408, which function as suture fasteners. The tabs 1408 may be integrally formed from the anchor body 1402 by cutting or drilling out of the anchor body 1402. The tabs may also be formed during the stamping process shown in and described in FIG. 25, below. Alternatively, the tabs 1408 may be attached to the anchor body by welding or adhesives.

A tab 1408 may be round, triangular, square, or be of a non-regular shape. The tab 1408 is connected to the anchor in at least one portion. The collapsing of a tab 1408 can be caused, for instance, by bending, pressing, or exerting sufficient force onto the tab by the bone so that at least part of it bends, thereby cinching a suture positioned behind the tab 1408 in place. In some embodiments, the deformation is reversible. That is, after a first deformation of the tab 1408 which causes the suture to become fixedly attached to the anchor, the removal of the collapsing force can allow the tab 1408 to bend outward, thereby allowing the suture to become releasable from the anchor. In some embodiments such deformations causing suture fixation and release can be performed multiple times. In other embodiments, such deformation can occur only once or a limited number of times. For example, in one embodiment, once the tab 1408 is deformed, it will not release even upon removal of the collapsing force.

In a preferred embodiment, the tabs are flush with the outer surface of the anchor body. Sutures 1450 can be slid around the side of the tab or optionally, can be threaded using a needle threader or any other mechanism. The nature of the suture thread is not critical.

In one embodiment, the tabs 1408 are flush with the anchor body outer surface. In other embodiments, the tabs 1408 extend laterally beyond the outside surface of the anchor body 1402 prior to insertion of the anchor 1400 into bone. In some embodiments, prior to complete insertion of the anchor 1400 into the bone, suture threads can be threaded or slid behind the tabs 1408 on the anchor body 1402. In some embodiments, an optional suture threading device can be used. The threading portion of the threading device may be a variety of shapes including curved or straight. When the anchor 1400 is inserted fully into bone, the suture can be held in place by pinching of the suture between the anchor body 1402 and bone and pinching of the suture between the tabs 1408 and the anchor body 1402. In some embodiments, contact with the bone can cause the tabs 1408 to bend inward, thereby providing further pinching the suture between the tabs 1408 and the anchor body 1402.

In the embodiment of FIG. 14, the tab 1408 is protruding outward, in a position that has not locked or fixedly secured a suture (not shown) in place yet. Applying pressure on the tab in direction of arrow H will collapse the tab onto the top of anchor 1400, thereby fixedly locking suture against the anchor 1400. This may be accomplished by pressing the anchor into a bone hole such that the sides of bone hole force the tabs 1408 inward. Alternatively, in some embodiments, the tabs 1408 may be collapsed prior to insertion of the anchor into bone by hand or by using an insertion tool as shown below.

In embodiments depicted in FIGS. 14, 17, and 18A-18B (described below), the anchor body 1402 may optionally have holes 1420, 1820 extending laterally through the anchor body 1402. Such holes may be used, for example, for threading of sutures and may be used in addition to or alternatively to other suture attachment features described herein, such as deformable tabs or suture attachment to the spreader 1430. In the embodiment depicted in FIG. 14, there are two options for securing the sutures 1450, holes 1420 and tabs 1408, of which either or both may be used. The holes in the anchor body 1402 that are configured to receive sutures 1450 may be used alone as an alternative to the tab configuration. In such a configuration, the tabs to do not have to be present. FIGS. 18A and 18B depict embodiments in which tabs are not present. In the illustrated embodiment in FIGS. 14, 15, 17, and 18A-18B, the opening may accommodate an insertion tool, a spreader and an optional cap, as described below.

Figure 15:
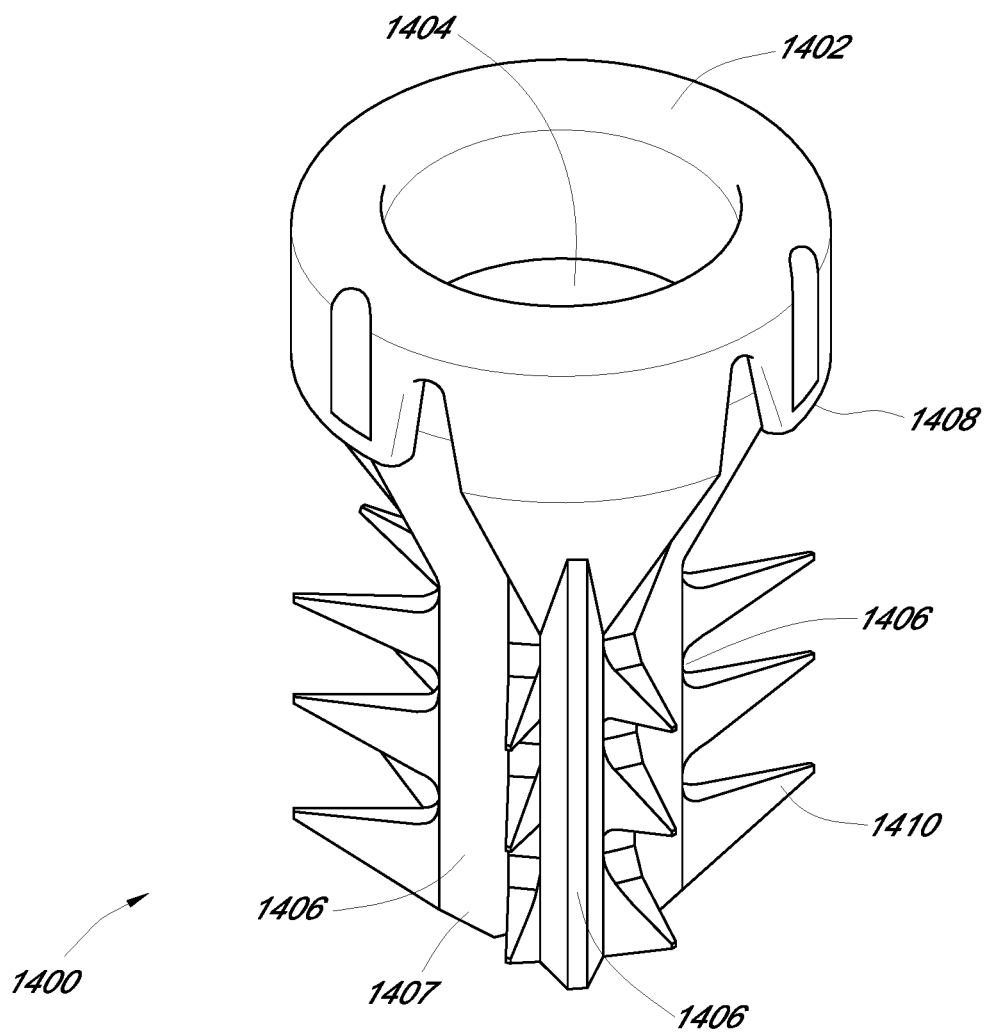
FIG. 15 depicts an alternative embodiment of the anchor.

As depicted in FIG. 15 which depicts another embodiment of the bone anchor 1400, the tabs 1408 can extend from the top of the anchor body 1402. As illustrated in FIG. 15, the tabs 1408 may essentially replace the outer surface of the anchor body 1402 in the positions at which they are located. In other embodiments, the tabs 1408 may extend outward from the outer surface of the anchor body 1402. In still other embodiments as depicted in FIG. 18, the tabs 102 may extend from the bottom end of the anchor body 1402. The tabs 1408 may be positioned at any locations circumferentially around the anchor body 1402. In some embodiments, the tabs 1408 are positioned between each tine 1406.

In some embodiments, the sutures can be threaded under the tabs 1408 before the anchor body 1402 is fully inserted into the bone whereby upon insertion the tabs will be pushed flat against the anchor body thereby securing or "pinching" the tabs into a secure position by collapsing the tab.

Figure 16:
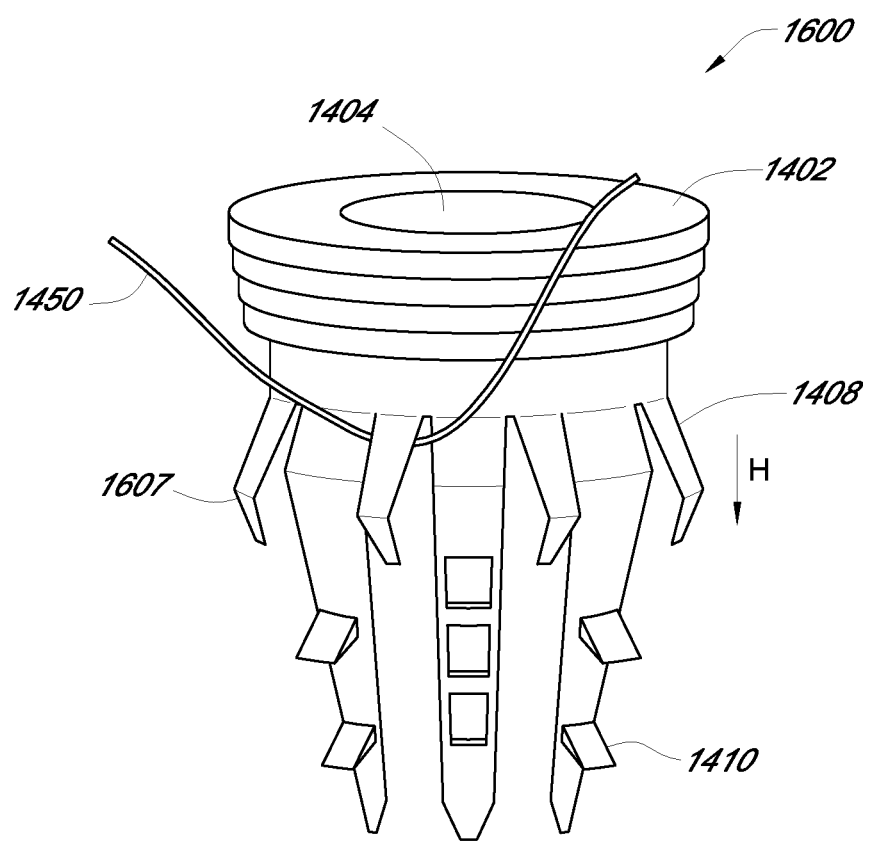
FIG. 16 depicts an anchor with bent tabs and tines.

FIG. 16 shows another embodiment 1600 of an anchor 1400. In this embodiment, laterally extending teeth 1410 are used to secure the anchor 1600 in the bone. The anchor also has flexible tabs 1408, which may be bendable or hinged, and capable of being collapsed into a locking state. In this embodiment, the tabs 1408 have intermediate bends 1607, which facilitates collapsing of the tab 1408 when the bone contacts the bend 1607. Collapsing the tab 1408 secures and locks any suture 1450 which has been placed beneath it, thereby capable of securing a suture to a bone by means of the anchor. Applying pressure on the tabs 1408 in direction of arrow H will collapse the tabs 1408 inward, thereby pinching the suture against other parts of the anchor 1600. Although this embodiment has four tabs visible, generally one or more such deformable tabs may be present. The tabs can be bent or collapsed by insertion of the anchor 1600 into bone or manually using a tool either prior to or during anchor insertion.

Although the suture capture tabs have been described with respect to the "push in" spreader embodiments, it will be appreciated that such tabs may also be used with the "pull up" embodiments described above.

As discussed above, the bendable tines 1406 in the anchor may be in a low-profile streamlined position prior to insertion into bone. A spreader 1430 may be used after insertion to expand the tines such that their teeth engage bone.

Figure 17:
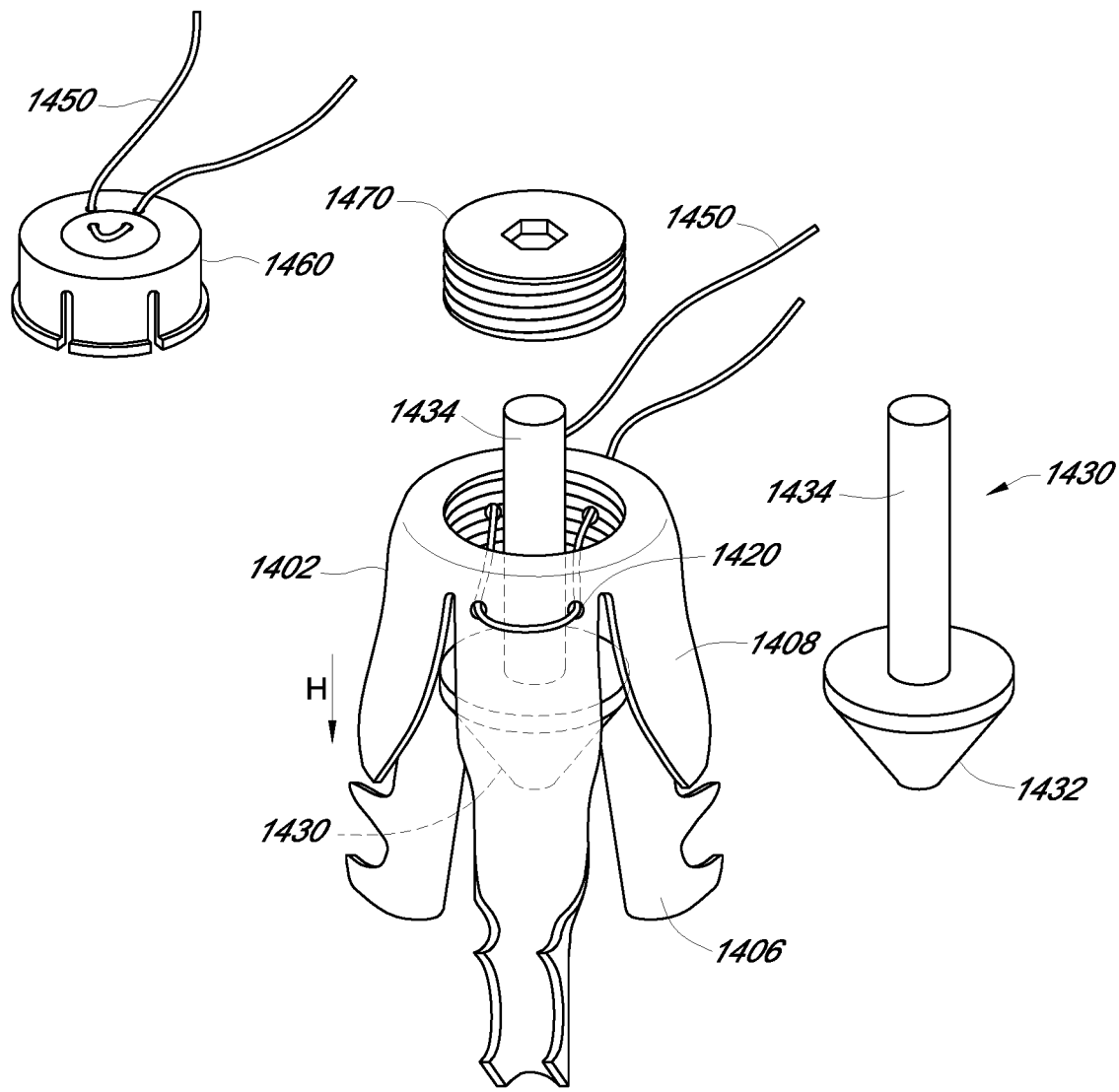
FIG. 17 depicts various embodiments of the spreader device and optional caps.

In the embodiment depicted in FIG. 17, the spreader 1430 is an elongated structure comprising a distally positioned head 1432 designed to contact the tines 1406 and a proximally positioned shaft 1434 that is designed to interface with an insertion tool or cap (described below). The spreader may comprise any suitable shape configured to be inserted through the axial bore 1404 in the anchor body 1402 and make contact with the bendable tines 1406. The spreader 1430 may be at least partially positioned within the axial bore 1404 of the anchor prior to tine expansion as depicted in FIG. 17. As the spreader 1430 is moved from a first upper position to a second lower position, the distal end of the spreader is designed to spread or force the tines 1406 from a first low-profile position (for example, an internal lateral position) to a second external lateral position.

The spreader 1430 of FIG. 17 is designed to be slidably received by the hole in the anchor body 1404. In such embodiments, the spreader 1430 can have a surface for receiving impact force and transmitting the force symmetrically down the length of the spreader 1430. The head 1432 can be flat or slightly concave to prevent slippage of the driver during use. In some embodiments, the head 1432 may have ridges to assist in preventing slippage or mis-alignment.

The spreader 1430, whether slidably received or threaded, will remain in the anchor 1400 with the tines 1406 in their fully spread position. The force provided by the tines' interaction with the bone keeps the spreader 1430 tightly engaged. Further protection against slipping or tilting of the spreader 1430 is provided by the optionally ridged sides of the spreader 1430 and by an optional cap 1460. 1470. In some embodiments, the spreader head 1432 may have ridges or indentations to assist in a tight fit such that accidental slipping or adjustments are minimized while deliberate withdrawals are possible after insertion into bone without inadvertent pull-outs. In one embodiment, one or more of the tines 1406 have an indentation on a side facing the central axis of the anchor 1400. A ridge on the spreader head 1432 can then engage the indentation, thereby stabilizing the spreader 1430 and preventing the spreader 1430 from being advanced too far into the anchor. In an alternative embodiment, the spreader head 1432 comprises an indentation (for example, an indentation in a ridge on the spreader head 1432) that can engage with a protrusion on a side of a tine facing the central axis of the anchor. In addition, to stabilizing the spreader and preventing over insertion, this feature also prevents rotation of the spreader 1430 relative to the anchor.

FIG. 17 further illustrates an optional cap 1460 or 1470 that may interface with the spreader 1430 to keep it straight and prevent it from being pushed out after it has expanded the tines 1406. The cap 1460 or 1470 can interface with the distal end of the shaft 1434 of the spreader 1430. In some embodiments, the distal end of the shaft 1434 engages a hole or other receptacle in the cap 1460 and 1470. The cap 1460 or 1470 can be secured to the anchor body 1402 of the anchor via threading 1470 or snaps 1460. The screwing or snapping in of the cap 1460 or 1470 may be accomplished by the insertion device, as outlined below, as a last step of tine 1406 expansion. The cap 1460 or 1470 can also be optionally threaded with sutures as an alternative to or in addition to the tabs or suture holes in the anchor body 1402. In such an embodiment, the cap may be pre-threaded with sutures 1450 prior to anchor insertion.

In another embodiment of a bone anchor 1800, the spreader 1830 is threaded as in FIG. 18A and driven by torque. The threads of the spreader engage corresponding internal threads in the hole of the anchor body 1802. In such an embodiment, the spreader 1830 can be single or multiply slotted or comprise a socket such as a hexagonal socket for receiving a complementary spreader rotational driver. In this case, the spreader 1830 can be screwed further into the anchor to cause expansion of the tines 1406, as depicted in FIG. 18B. When engaged with the insertion tool, with or without the optional cap as described below, the spreader 1830 will advance down the anchor towards the distal end as it is rotated. As the spreader advances towards the distal end, the body of the spreader 1830 spreads the bendable tines 1406 away from the anchor body. As the bendable tines 1406 expand, the tines become lodged in the bone thereby creating a locked position for the anchor 1800. One advantage of this embodiment is that the spreader 1830 can be reversed and the anchor 1800 removed from the bone. This configuration also allows the spreader 1830 to be screwed back out to allow for adjustment of the anchor or attached sutures.

In some embodiments when the cap 1460, 1470 is used as an alternative to the tabs 1408 to secure the sutures, the sutures are pre-threaded before insertion. As an alternative or as an addition to the suture securing method described above, a surgeon may choose to use the deformable suture securing tabs 1408. In one embodiment, a length of suture can be passed underneath the tab 1408 and tensioned in place. Then, the anchor is placed the rest of the way into the bone which pressure collapses the tab 1408 and fixedly secures the suture to the anchor.

4. Bone Anchor Insertion Tool for Proximal Spreader Alternative

Figure 19:
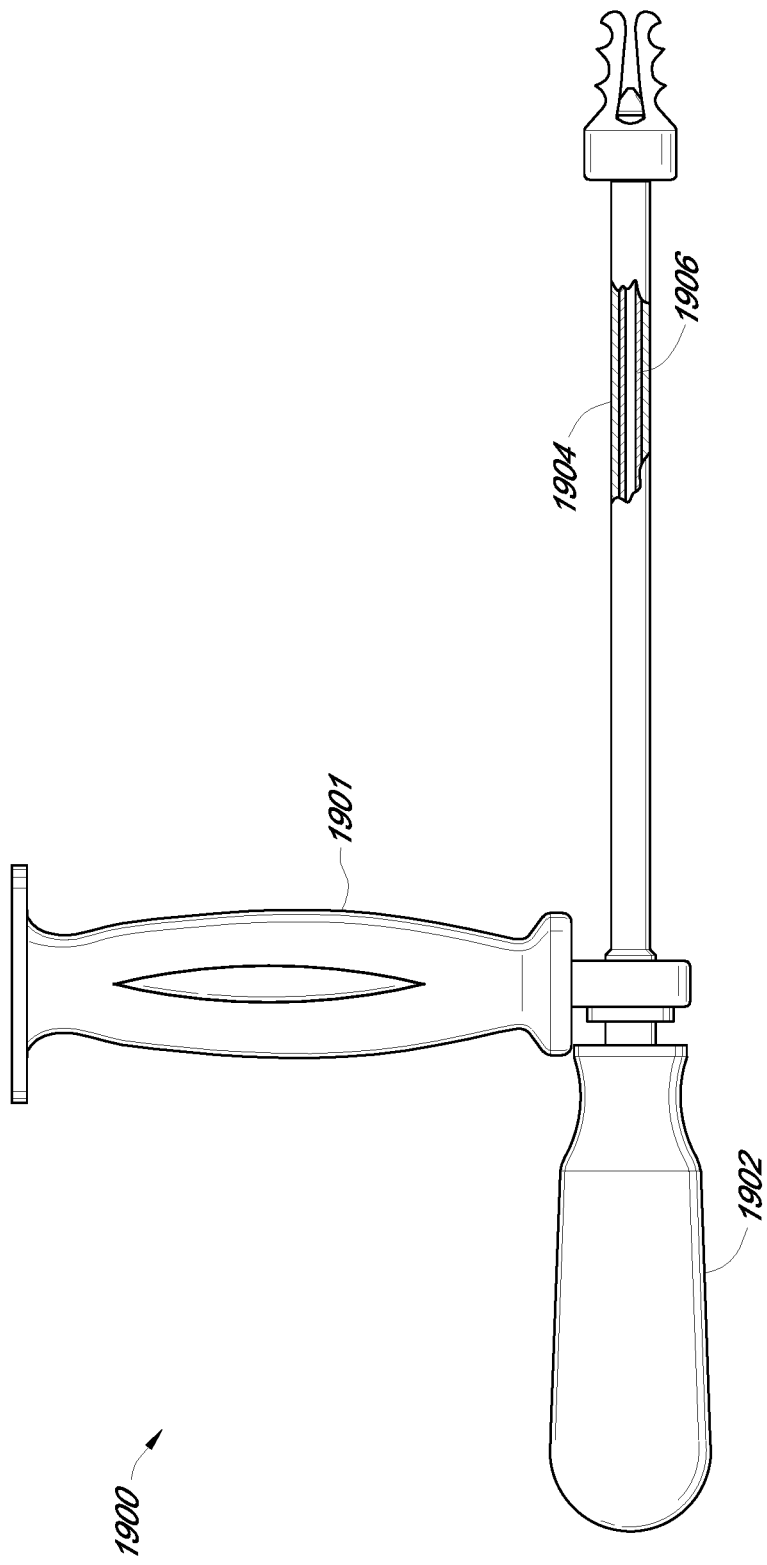
FIG. 19 depicts an embodiment of an insertion tool.
Figure 20A:
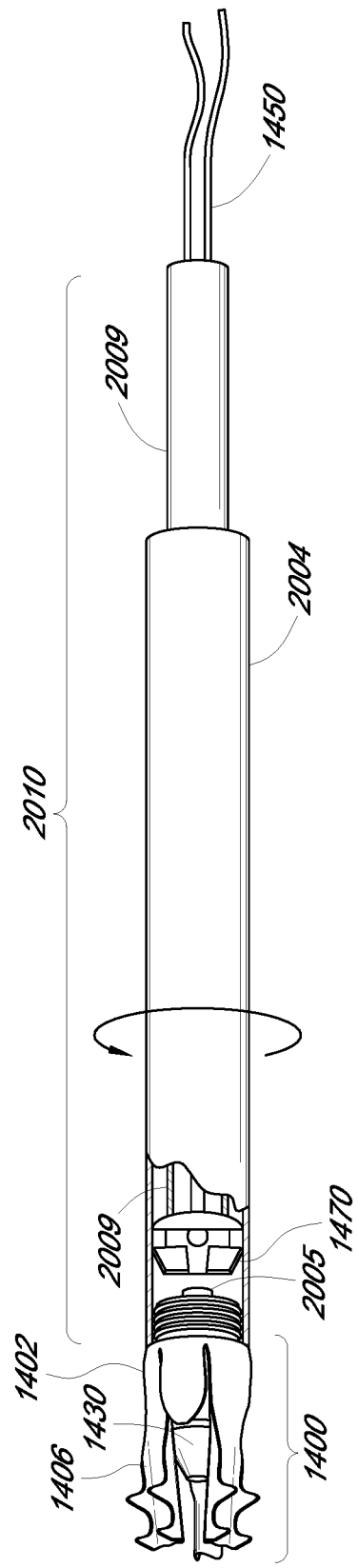
FIG. 20A depicts another embodiment of an insertion tool.
Figure 20B:
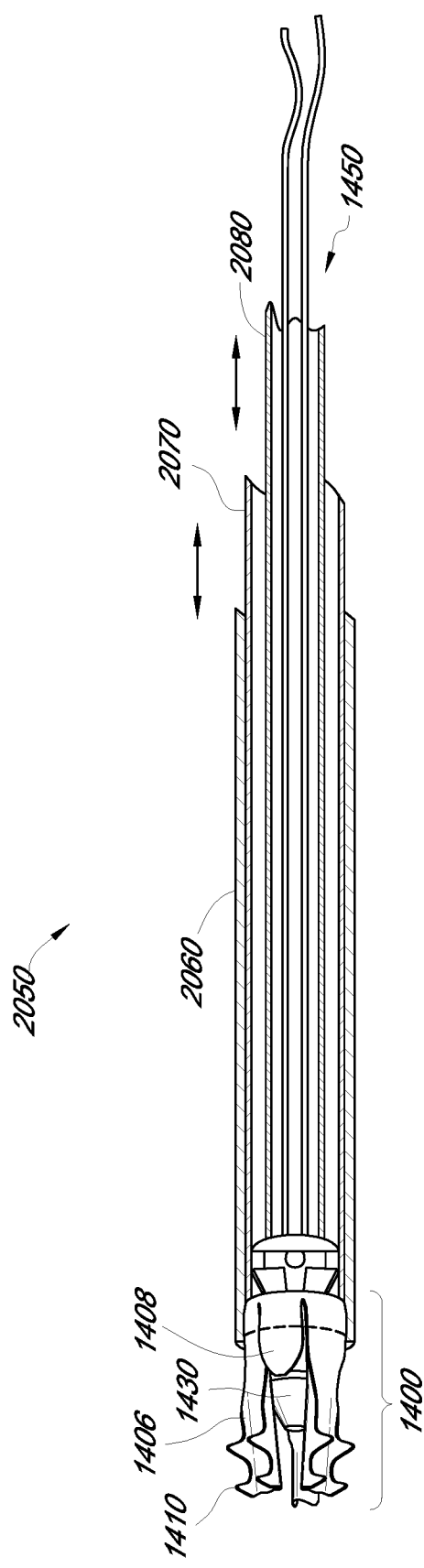
FIG. 20B depicts a cut-away view of an embodiment of an insertion tool.

The bone anchor device may be provided with an insertion tool designed to insert the bone anchor into bone and then deploy the spreader to expand the tines 1406 on the bone anchor. Some embodiments of the insertion tool are depicted in FIGS. 19, 20A and 20B. In general, the insertion tool comprises a handle portion at a proximal end that can be manipulated by a surgeon for inserting the bone anchor and deploying the spreader, and a bone anchor-engaging portion at a distal end that can attach to the anchor and move the spreader.

As described above, in some embodiments the spreader is advanced into the bone anchor by the inserter tool by screwing into threads located in the interior the anchor body, either using corresponding threads on the spreader itself as depicted in FIGS. 18A and 18B, or by a screw-in cap as depicted in FIG. 17 element 1470, or by corresponding threads on a portion of the inserter tool. In such embodiments, the handle portion of the insertion tool can comprise features that facilitate rotational motion applied by the surgeon.

For example, one embodiment of such an insertion tool is depicted in FIG. 19 which depicts the inserter tool 1900 from a side perspective. Insertion tool 1900 comprises a longitudinally aligned handle 1902 that allows the surgeon to apply an insertion force to the bone anchor. Insertion tool 1900 also comprises a laterally directed handle 1901 that can pivot around the longitudinal axis of the inserter 1900. This rotational motion can be used to rotate an inner pushing mechanism 1906, such as a tube or a rod that interfaces with a spreader or screw-in cap 1470 as described below.

In some embodiments, the insertion tool may comprise an outer tube that can be reversibly coupled to the bone anchor, such as by snapping onto or screwing onto threads on the outside of the anchor body. FIG. 20A depicts such an embodiment. Outer tube 2004 is reversibly coupled to the bone anchor 1400 via threads allowing the inserter tool 2010 to be attached to the bone anchor 1400. Alternatively, tongue and groove sliding locks or magnets may be used or any other suitable engagement structure. Engagement between the outer tube 2004 and the bone anchor allows the user to position and apply insertion force to the bone anchor 1400 using the longitudinal handle 2002. In FIG. 20A, the embodiment further comprises an inner tube 2009 which pushes the spreader 1430 distally in the bone anchor 1400. In the embodiment depicted in FIG. 20A, the inner tube 2009 engages with a cap 1470 which in turn interfaces with the shaft of the spreader 1430. Rotation of the inner tube or pushing mechanism 2009 rotates the spreader or cap to drive it into the bone anchor and spread the bendable tines 1406 using either a spreader or cap with threads that interface with the anchor body 1402 or by threads on the inner pushing mechanism 2009 engaging with the anchor body 1402. The inner pushing mechanism 2009 can interface with a spreader or screw-in cap hex structure or other driving feature. Alternatively, when the spreader 1430 is slidably received by the bone anchor 1400, the inserter 2010 of FIG. 20A may be designed such that rotation of the lateral handle 2001 advances the inner rod longitudinally, such as by threads within inserter 2010. In this case, the spreader and/or cap are advanced by the inner pushing mechanism 2009 pushing them downward. Any other suitable handle configuration or mechanism can be used to facilitate a surgeon applying rotational motion to the inner pushing mechanism 2009.

In other embodiments, where the spreader 1430 is slidably received by the bone anchor, the handle portion of the inserter may include features that allow the inner pushing mechanism 2009 to be slid distally relative to the outer tube 2004. For example, in one embodiment, the inserter 2010 comprises a longitudinal handle feature positioned distally from the longitudinal handle 2002 that can slide distally over the outer tube 2004. This feature may be coupled to the inner tube or pushing mechanism 2009 to facilitate the distal sliding of the mechanism.

In another embodiment, a cross-sectional view of which is depicted in FIG. 20B, the insertion tool 2050 which comprises an outer tube 2060, an advancing tube 2070 and an inner tube 2080, sutures 1450, an anchor 1400, tines 1406, teeth 1410, tabs 1408, and a cap 1470. In this embodiment, the slidably mounted outer sleeve 2060 fits over both the tube 2070 used to initially seat the bone anchor and also the inner pushing mechanism 2080 for driving the spreader, thereby providing three concentric elements for interfacing with the anchor and deploying the spreader 1430. After the anchor 1400 is inserted into the bone, the outer sleeve 2060 may be slid backward relative to the outer tube 2070 and inner rod 2080. The sleeve 2060 makes contact with the anchor body 1402 and properly positions and aligns the inserter tool 2050 relative to the anchor 1400. The sleeve 2060 is used to initially place the anchor in a pre-drilled hole and may optionally be reversibly attached to the anchor body 1402 by screwing onto threads or by snapping onto the anchor body 1402. The sleeve 2060 can also be used to hold the tabs 1408, if present, in an inward compressed position during insertion of the anchor so that the tabs 1408 do not interfere with the insertion. In some embodiments, slots may be provided in the sleeve 2060 so that sutures can be slid behind the tabs 1408 when the sleeve 2060 is in position over the anchor body 1402. After the anchor 1400 is positioned into the bone, the sleeve 2060 may be slid backwards and the anchor driven all the way into the hole by applying force to the driver tube 2080. Alternatively, the sleeve 2060 can remain in contact with the anchor body 1402 throughout anchor insertion. In some embodiments, the driver tube 2080 only contacts the anchor body 1402 during anchor insertion. In other embodiments, the driver tube 2080 is attached to the anchor body 1402 such as by snapping or screwing onto the anchor body 1402.

The inner pushing mechanism 2080 is positioned within the driver tube 2070 and can be slidably or rotationally driven to push the spreader 450 through the anchor body 1402 to expand the tines 1406. The inner pushing mechanism 2080 can either drive the spreader directly or, as depicted in FIG. 15, push a snap-in 4200 or screw-in cap 1470 into the anchor body 1402. The cap 1470 in turn simultaneously advances the spreader 1430. In some embodiments, the cap, for example a snap-in cap 1460, can optionally have pre-attached sutures. After insertion of the anchor and deployment of the spreader 1430, the inserter may be decoupled from the anchor such as by unscrewing or unsnapping the sleeve 2060 and/or the driver tube 2070 from the anchor body 1402.

Figure 21:
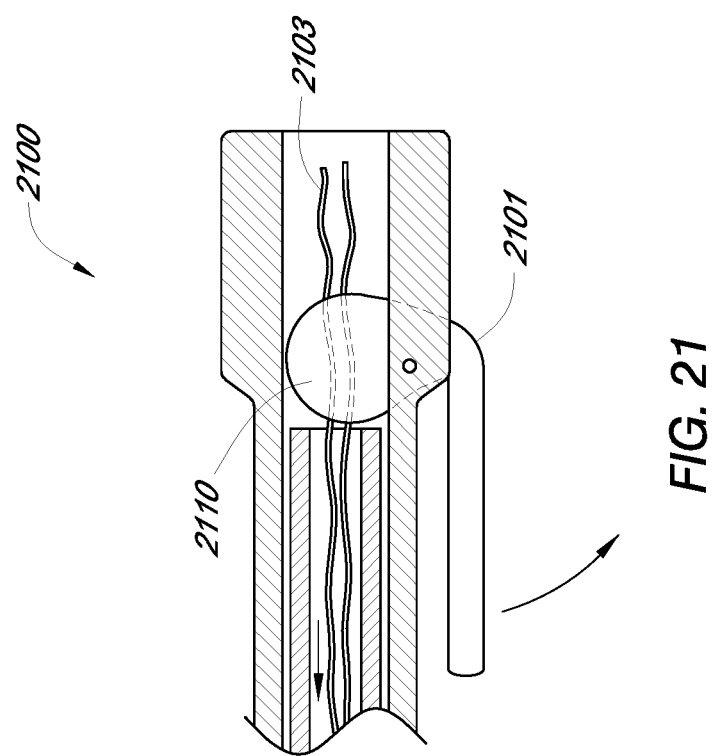
FIG. 21 depicts an insertion tool utilizing a cam and lever.

In another embodiment, depicted in FIG. 21, the inserter 2100 comprises a cam 2103 and lever 2101 configuration. The inserter tool 2100 has no moving parts. In this embodiment, the predrilled hole is made to receive the anchor (not shown) upon insertion. The surgeon then inserts the anchor (not shown). When the surgeon is ready to expand the tines of the anchor and engage with the bone, the surgeon would lift the lever 2101 and the cam would force the inner rod 2112 to move the spreader (not shown) distally thereby engaging the tines with the bone.

Figure 22:
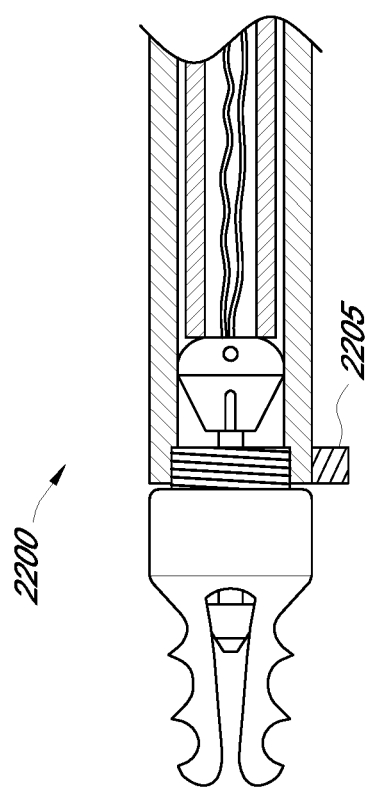
FIG. 22 depicts a stopper component on an embodiment of an insertion tool.

In some embodiments, the insertion tool comprises a laterally extending stopper, or flange 2205, as in FIG. 22. The stopper 2205 can be located on one side, both sides, or extend all the way around the inserter tool. The stopper 2205 rests on the top of the bone cortex once the anchor 1400 is inserted, thereby preventing over-insertion and providing more stability for the insertion tool during the driving of the spreader. In other embodiments, over-insertion is prevented by the precisely measuring the depth of the pre-drilled hole.

5. Suture Capture Alternative

Figure 23:
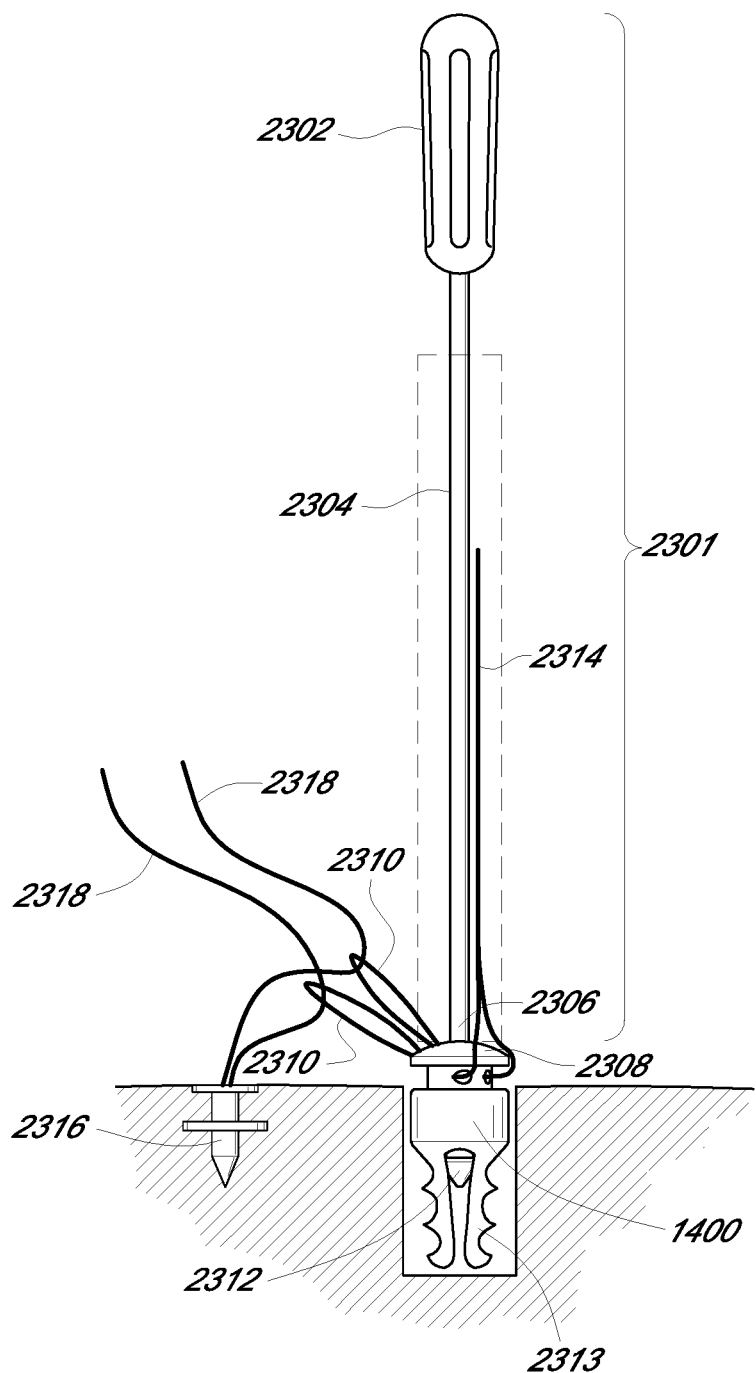
FIG. 23 depicts an embodiment of an anchor and cap using nitinol loops to thread the sutures.

In another embodiment, the sutures are attached to the bone anchor after it has been inserted into the bone, for instance inside the patient's shoulder or knee, as shown in FIG. 23. FIG. 23 depicts a one-piece suture capture anchor which permits the sutures to be threaded through the cap while the insertion tool is inside the body. This embodiment comprises an anchor 2300, an insertion tool 2301, a handle 2302, an outer tube 2304, an inner tube 2306, a cap 2308, one or more suture capture loops 2310, and sutures 2314. Using this anchor, suture that is already within the surgical site, such as from another already-inserted anchor or stitched to body tissue, may be captured at the point of anchor insertion.

The bone is prepped for the bone anchor 2300. The top of the insertion tool 2301 includes a handle 2302 attached to the outer tube 2304 and the inner tube 2306 to facilitate a surgeon applying force to the insertion tool 2301. The outer tube 2304 is reversibly coupled to the anchor 2300, such as by snapping onto or screwing onto threads on the anchor body of the anchor 2300. The inner tube 2306 engages with a cap 2308 which attaches by snapping or screwing to the shaft 2310 of the spreader 2312. The cap 2308 further comprises a series of nitinol loops 2310 which will thread the sutures 2314 once the anchor 2300 is engaged with the bone.

When the insertion tool 2301 is inserted into the body and the anchor 2300 is engaged with bone, the inner tube 2306 can advance the cap 2308 into the anchor such the surgeon can further snap or screw the cap 2308 into the anchor 1400. During initial insertion and positioning of the anchor 1400, the cap 2308 has nitinol loops 2310 positioned just inside suture holes through the cap 2308. The nitinol loops 2310 can then be advanced to receive and capture the sutures 2314. The sutures 2314 can be threaded through the loops 2310. When the nitinol loops 2310 are withdrawn and the sutures 2314 are pulled through the suture holes and back outside of the body where they are available to the surgeon for tensioning. The surgeon can make all of the tensioning adjustments he needs without having to have any loss of contact with the bone anchor body 1400.

Figure 24A:
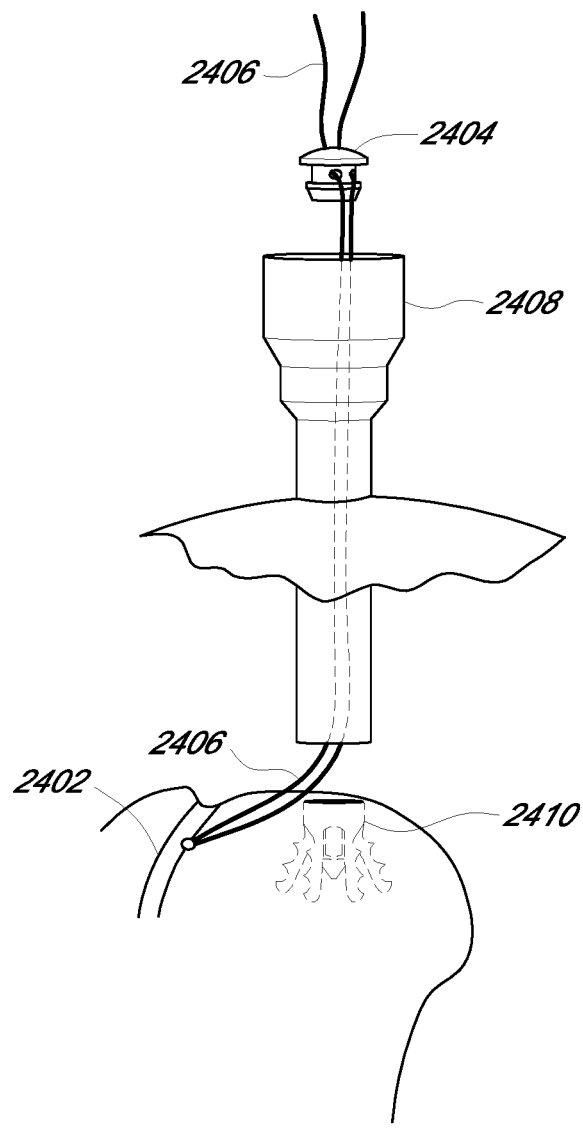
FIGS. 24A and 24B depict an alternative embodiment of the anchor using a slideable cap threaded with sutures to secure the sutures between the cap and the anchor.
Figure 24B:
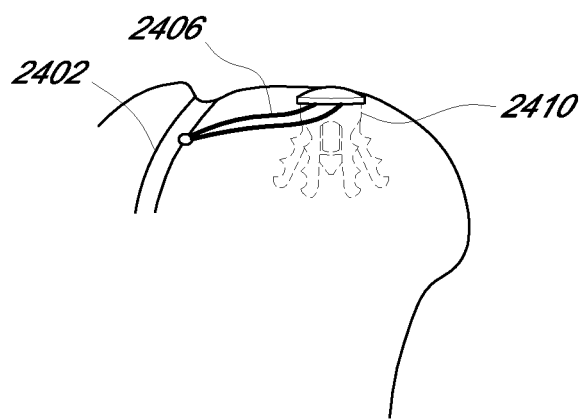

Another embodiment, shown as FIGS. 24A and 24B, shows a pre-threaded sliding cap embodiment. FIG. 24A illustrates the embodiment before the sutures are tensioned, and FIG. 24B illustrates the embodiment after the sutures are tensioned. The embodiment describes a first inserted anchor 2402, a cap 2404, sutures 2406, a cannula 2408, and a second inserted bone anchor 2410.

In this embodiment, the surgeon takes the sutures 2406 from a first inserted anchor 2402 of any type, which is already inserted and secured to bone, and threads the sutures 2406 through a capturing member such as a cap 2404 outside of the body, for instance, the shoulder. The cap 2404 is then advanced down the sutures 2406 through the cannula 2408, and snapped or otherwise fixedly attached to a pre-installed second bone anchor 2410 as previously described. This embodiment allows tensioning of the sutures 2406 2404 before final insertion of the cap 2404 into the anchor 2410, and thus the final capture of the sutures 2406. In some embodiments, the cap 2404 has ridges to ensure adequate suture pullout forces. In other embodiments, the cap has a positive locking that crushes the suture as the cap is forced into place. It will be appreciated that this anchor may be employed with any suture already available at the surgical site (for example, suture that has been stitched to body tissue).

Although a particular inserter device for inserting and manipulating the anchor 1400 has been described, it should be understood that other inserter designs may be used for manipulating the parts of anchor 1400 described above to insert the anchor into bone and secure suture material to the anchor. For example, it may be possible to use separate tools for inserting the anchor and securing the suture material. In some embodiments, the collapsing of the tabs 1408 so that they do not interfere with the insertion of the anchor may be accomplished by instruments other than the inserter. For instance, the tabs may be compressed during anchor insertion by forceps, fingers, a rod, or any other suitable mechanism, capable of deforming the tab.

Some embodiments include multi-component kits. The kits may include the tissue stabilizing device as described herein as a first component. Other components can include a drill and drill bits for forming a bone hole, sutures, and an inserter tool as described above. In some embodiments, the kit provides the anchor already engaged with the inserter tool ready for insertion. In some embodiments, the anchor is provided with pre-attached sutures, such as sutures attached to the various spreader cap designs described above.

Method of Manufacturing

In one embodiment, the anchors described in FIGS. 14-24 herein are manufactured by stamping of a sheet of flat material instead of by machining or molding. First, a flat form is produced. The flat form can be made of many different materials, for instance, such as metal (for instance, titanium or stainless steel), plastic or fiberglass. A pattern is then stamped out of the flat material. Alternatively, this flat form can be shaped using a laser, chemical etching or some other suitable method.

After stamping of the flat material, the shape of the anchor is achieved by bending or folding the flat sheet.

Figure 25:
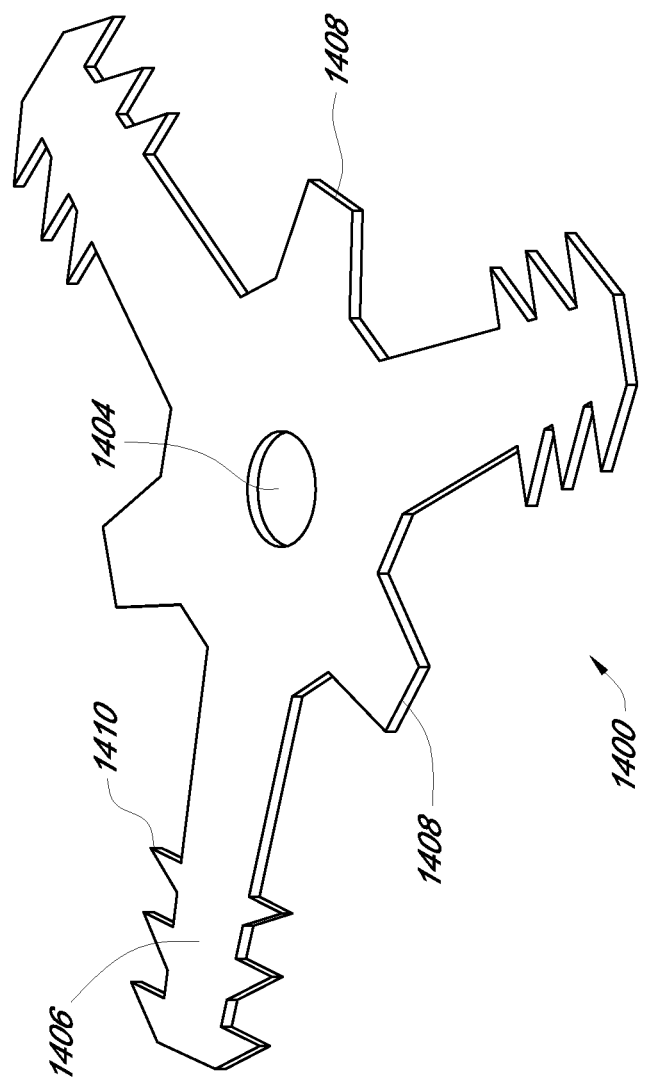
FIG. 25 depicts an embodiment of a bendable tine stamped from a single sheet of metal during the bendable tine manufacturing process.

FIG. 25 shows an embodiment of an anchor 1400 during an early stage in its manufacturing process. The anchor 1400 may be stamped from a single sheet of metal foil or other pliable material using stamping dies and methods that are common or well-known in the art. The shape of the stamped piece can include outlines for tabs 1408, adjustable tines 1406 with teeth 1410, and an axial bore 1404 for receiving an insertion tool. Initially the stamped sheet may be largely two-dimensional. In order to form the final anchor, the tines 1406 can be bent or folded in an upwards direction to form a three-dimensional anchor. The tabs 1408 can also be slightly bent upwards in order to form projecting protrusions. They can be fully bent such that they are substantially perpendicular to the central plane of the anchor when a suture is ready to be locked in place, in the various manners described previously. The embodiment shown, the anchor has three spiked tines 1406 and three tabs 1408; however, various numbers of tines and tabs can be used. The resulting anchor will have the shape depicted in FIG. 14.

In some embodiments, the anchor is made of polymeric materials and is formed by conventional machining using, for example, a CNC turret machine. The anchor could also be injection molded.

Surgical Methods

Various embodiments include methods for attaching soft tissue to bone. In one embodiment, the methods include using the suture anchors described above.

In the preferred method, the procedure is performed arthroscopically; however, use of the anchor is not limited to any particular technique. Techniques for preparing an anchor insertion site, anchor insertion, and suture handling are well-known in the art. For purposes of exemplification, the details of one particular technique are provided below.

Figure 26A:
FIG. 26A shows a single-row rotator cuff repair using two suture anchors.

One method uses a 6 mm PEEK suture anchor, although different sizes and materials may be used. In one embodiment, the bone surface may be prepared with a drill bit or awl that creates a hole in the bone large enough to receive the anchor. The cut hole can be either straight or angled to walls to form a Morse taper. One embodiment, as shown in FIG. 26, anchors either having 2 or 4 suture strands (as described above) are used to perform a single row soft tissue repair (for example, a torn rotator cuff repair). FIG. 26A depicts an arthroscopic repair using a single-row simple-suture technique with two anchors placed laterally to the soft tissue. In the case of massive tears, 3 anchors may be used. Each anchor is typically loaded with either one strand (i.e., in 2-limb anchor) or two strands (i.e., in 4 limb anchor) of No. 2, nonabsorbable, ultra-high molecular weight polyethylene suture, although any suitable suture material may be used. For rotator cuff repair, the anchors typically are inserted 5 mm to 10 mm apart at the lateral edge of the rotator cuff insertion footprint at 45° to the surface of the bone. One half of the suture strands (i.e., one strand for 2-limb anchors or 2 strands for 4-limb anchors) is passed through the tendon ~10 mm from the free edge. The sutures are typically tied by hand using a slipknot, followed by 3 alternating half hitches.

Figure 26B:
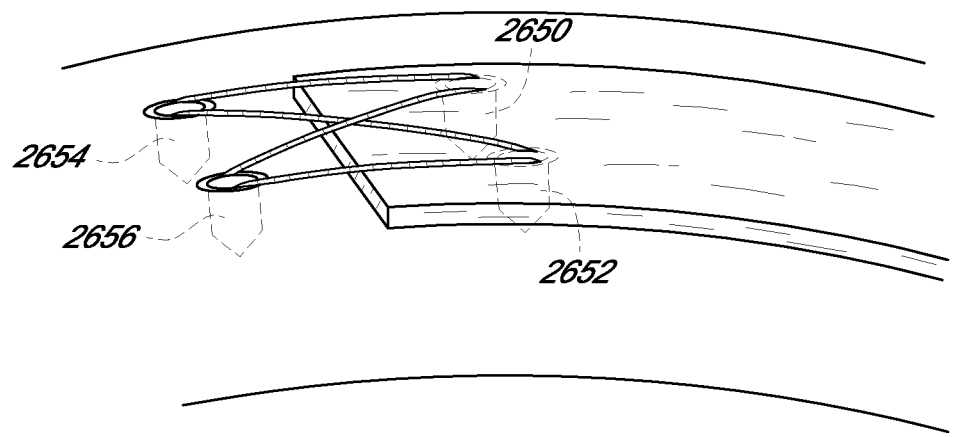
FIG. 26B shows a double-row rotator cuff repair using four suture anchors.

In other embodiments, suture capture anchors such as described in U.S. Patent Application Publication No. 2006-0004364, which is incorporated herein by reference in its entirety, may be used in combination with the anchors described herein to create a variety of anchor and suture patterns. In such embodiments, suture may be run from one of the anchors disclosed herein over soft tissue before being secured to a suture capture anchor. In one embodiment, a double-row technique such as that depicted in FIG. 26B is used wherein the medial row utilizes the anchors described herein and the lateral row utilizes suture capture anchors. Two-strand or four-strand suture anchors 2650 and 2652 may be inserted beneath the soft tissue along the medial row. The sutures may then be passed over the soft tissue and captured with suture-capture anchors 2654 and 2656 along the lateral row. In some embodiments (for example when four-strand suture anchors are used) some suture strands may also be tied over the soft tissue. In certain embodiments, including those depicted in FIGS. 26A and 26B, multiple anchors and sutures may be used to produce geometries such as depicted in FIG. 26B and variations thereof.

In one embodiment, a hole is predrilled into the bone. In various embodiments, the hole diameter is the same size, slightly larger, or slightly smaller than the diameter of the anchor. The smaller diameter hole provides an initial resistance to removal and stabilizes the anchor prior to deployment of the spreader. It will be appreciated that other means may be used to initially secure the anchor 100 to bone. For example, angled protrusions may be used that provide greater resistance to removal of the anchor base 100 than to insertion. The protrusions may be static or deployable once the anchor is inserted.

In another embodiment, the bone surface is optionally prepared with a awl or trocar that has a cutting surface that matches the anchor. This distal end has an external size and configuration to create a hole in bone that complements the external configuration of the anchor body 200 when its tines 220 are in the first position. The hole created by the trocar should be the same size or just slightly smaller than the external size of the anchor 100 when in the undeployed position of FIG. 1B. The trocar can be made of any material that can be sterilized, be formed into a cutting edge, and withstand the impact force needed to penetrate bone. Metal alloys such as stainless steel are preferred. The overall diameters of the trocar are not critical and need only be long enough to reach into the joint and extend outside a suitable distance for receiving the impact force, or for drill attachment to a chuck. An overall length of eight to twelve inches with an outside diameter of 0.3 to 1.5 cm is suitable for the anticipated uses.

Prior to anchor insertion, the spreader and the anchor can be mounted on an insertion tool. Alternatively, the insertion tool may be provided with the anchor pre-attached.

In one embodiment, healing of damaged soft tissue and promotion of its reattachment to bone may be aided through the use of a suture augment. Such an augment may be placed in contact with the soft tissue including the region where the tissue is damaged. In one embodiment, the suture augment is used to bridge gaps or span a defect between soft tissue including ligaments and tendons as well as gaps between the ligament or tendon to bone insertion points. Types of suture augments; various geometries of augments, sutures, and anchors; and methods for inserting and positioning augments are described in U.S. Application Publication No. 2007-0288023, which is incorporated herein by reference in its entirety.

In embodiments comprising a suture tab, sutures may be threaded or slid behind the tabs of the anchor, either within the surgical site or outside of the body. In some embodiments, the sutures may be wrapped in front and behind the anchor or wrapped around tines of anchor to create a more tortuous path and therefore increased pullout strength. In some embodiments, suture may alternatively or also be pre-threaded through passageways formed through the anchor body of the anchor, through the spreader, or through a spreader cap. The anchor can then be pushed into the pre-drilled bone hole and deployed while exerting downward pressure on the insertion tool. Generally, the anchor will be hand-driven, although machine-driven embodiments are possible as well. Finally, the spreader can be deployed using the various methods described above. As used herein, "suture" refers to any flexible structure that can be stretched between two or more anchors and includes, without limitation, traditional suture material, single or multiple stranded threads, or a mesh structure.

The suture attachment methods described in the previous paragraphs can be done either before the anchor is inserted into the hole or else when the anchor is partially inserted but before the tabs and/or anchor body (some embodiments will not have tabs) are positioned below the surface of the bone.

In some embodiments, either before or after suture is coupled to the anchor, it is passed over the top of the soft tissue so that the suture can press the soft tissue against the bone. In some embodiments, multiple lengths of suture attached to the anchor may be used.

The surgical procedures for which the anchors described herein are particularly suited are repairs to the shoulder and knee joints such as reconstructing anterior cruciate ligament (ACL) deficiencies and for repairing dislocating shoulders and torn rotator cuffs. However, the anchor is universally applicable to most efforts which warrant reattachment of soft tissue to bone. The brief description of surgical procedures herein are not intended to be the only way the embodiments described herein could be used and are presented for illustration purposes and not by way of limitation.

To place the anchor in its optimal position, one first conceptualizes the goals of repair to identify the location where the anchor will provide maximum security and adequate (isometric) function. The pathology is then reprobed to locate tissue to be captured. The anchor also provides for secure fixation in reconstruction cases, wherein autografts or allografts are used.

The surgeon then prepares the concavity for implanting the anchor by a limited synovectomy, burr notchplasty, and then by exposing bone. The bone may be prepared with a tap or punch or drill or an appropriate hole for the bone anchor.

For example, in the case of a knee surgery, the surgeon then places the anchor into the anteromedial knee wound through an accommodating cannula.

The anchor is then driven into the prepared concavity into the pre-drilled starter hold, while the knee is flexed at about 30°, and the assistant surgeon holds the tibia up towards the femur. The spreader is then driven down or pulled up, thus expanding the prongs inside the bone, locking the anchor into place. The optional use of sutures completes the repair. The surgeon tensions the sutures and checks the joint clinically for stability and impingement. In embodiments, where suture tabs are used, the tensioning of the sutures may be conducted prior to complete insertion of the anchor. In other embodiments, the sutures may be threaded or pre-threaded through the anchor body and/or spreader caps (such as depicted in FIG. 17).

In one embodiment, a length of suture can be passed underneath the tab and tensioned in place. Then the anchor is placed the rest of the way into the bone which pressure collapses the tab and fixedly secure the suture to the anchor. In yet another embodiment the suture can be pre-tensioned before finally seating the snap-in or screw-in cap into the anchor.

In a final step, the surgeon checks the joint motion, implant and joint stability, and rules out any impingement of the implant against mobile surfaces.

Example in a Rotator Cuff Repair Procedure

Figure 27A:
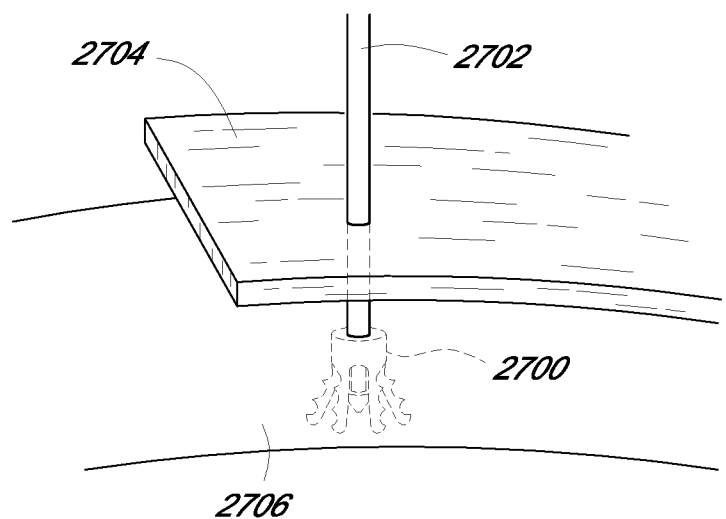
FIGS. 27A-27E depict manipulation of an embodiment of a suture anchor using a suture anchor inserter to insert the suture anchor into bone and attach suture material to the suture anchor.
Figure 27B:
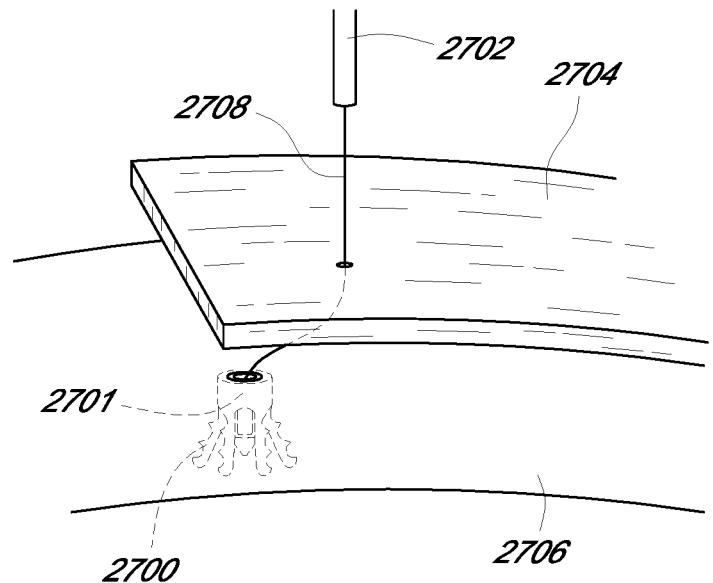
Figure 27C:
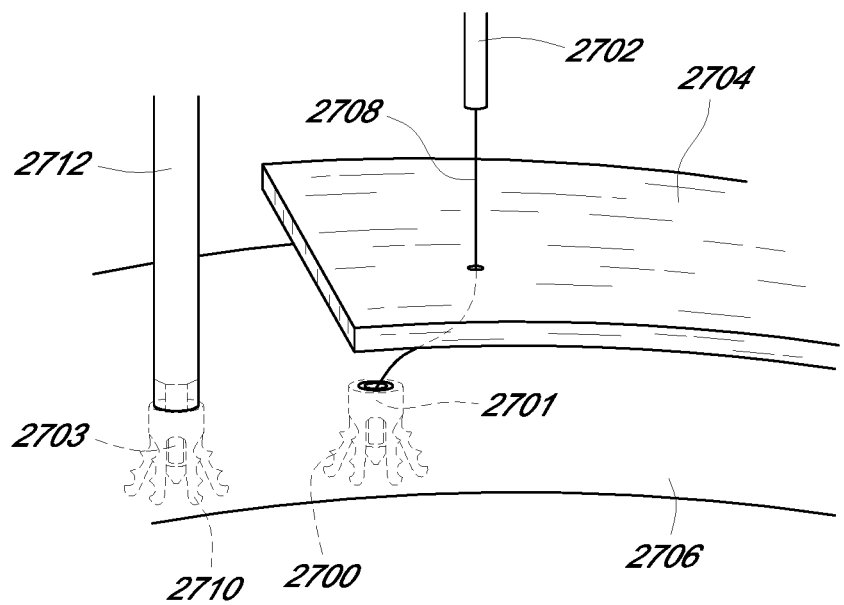

One specific application in which the anchors described above may be utilized is a rotator cuff repair procedure, as depicted in FIGS. 27A through 27E. In this embodiment, a torn rotator cuff is repaired using a two-point fixation technique where suture is attached between medial and lateral anchors. In the depicted embodiment, the medial anchor is an anchor that is inserted through the rotator cuff tissue and driven into underlying bone. In FIG. 27A, the anchor 2700 is inserted through soft tissue 2704 that has become detached from underlying bone 2706 and driven into underlying bone. In FIG. 27B, the anchor 2700 is then deployed to secure it into bone and its inserter 2702 is detached, leaving a suture 2708 attached to the bone anchor and extending through the soft tissue 2704. The anchor may be inserted into bone 2706 by tapping on the inserter 2702 with a hammer or by any other suitable means of applying axial force. FIG. 27C depicts the deployed anchor with attached suture. Any of the anchors described herein having pre-attached sutures may be used for the medial anchor in this embodiment. In other embodiments, an anchor such as described in U.S. Patent Application Publication No. 2007-0142835, which is incorporated herein by reference in its entirety, may be used for the medial.

Figure 27D:
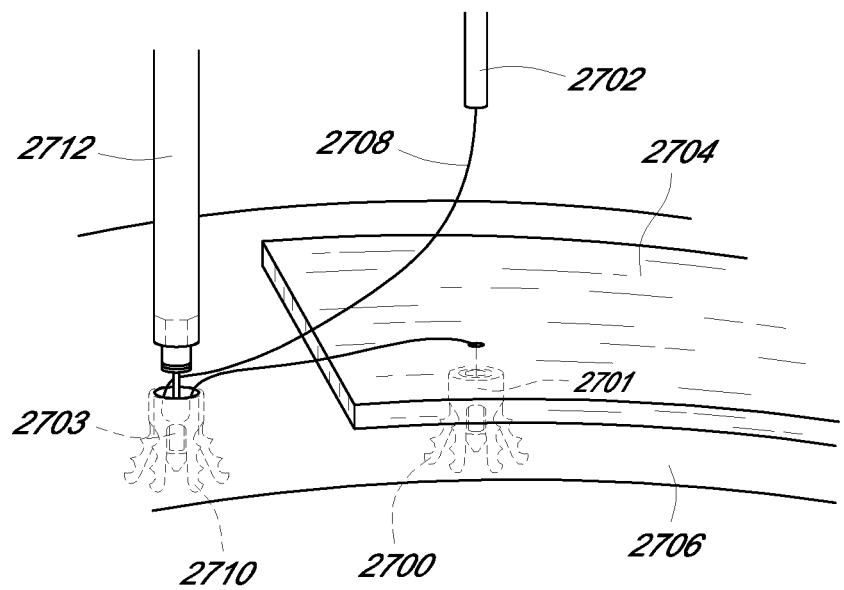
Figure 27E:
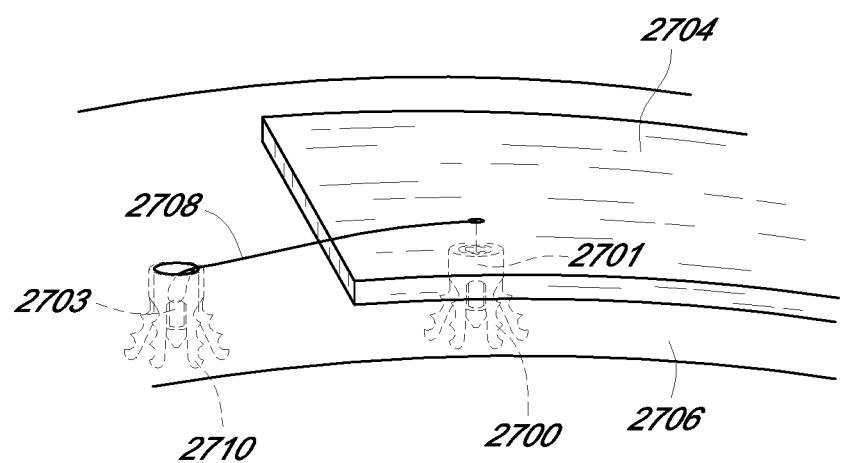
Figure 28A:
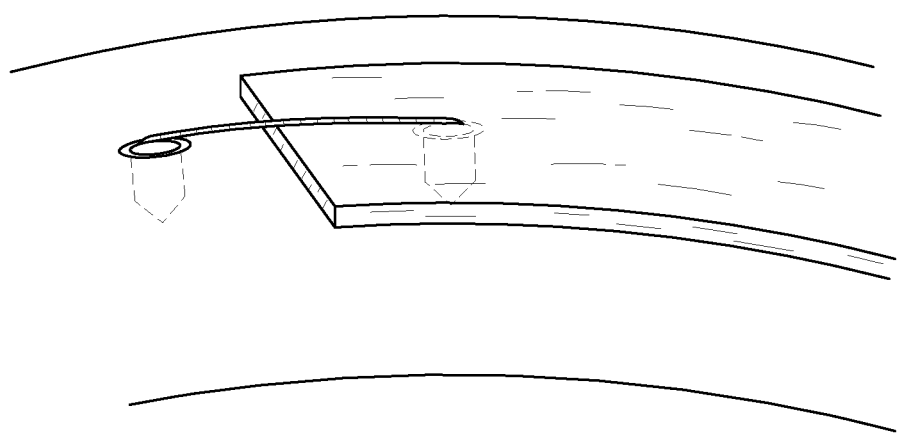
FIGS. 28A-28D depict various geometries produced by the use of multiple anchors, anchors, and sutures.
Figure 28B:
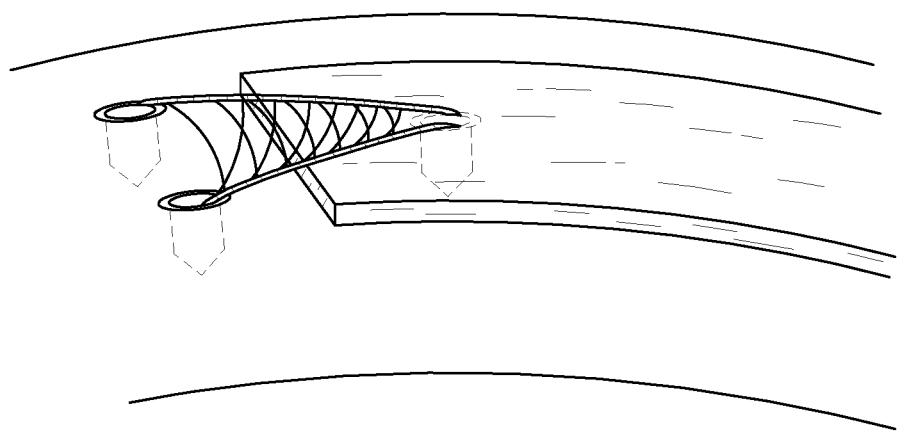
Figure 28C:
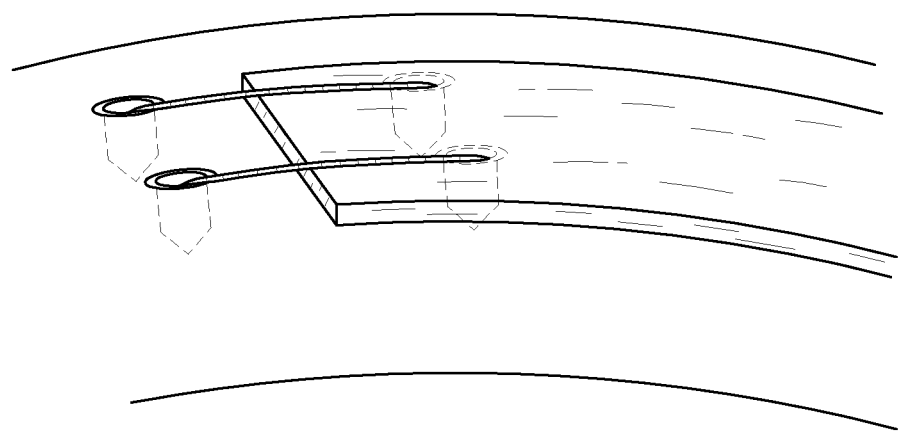
Figure 28D:
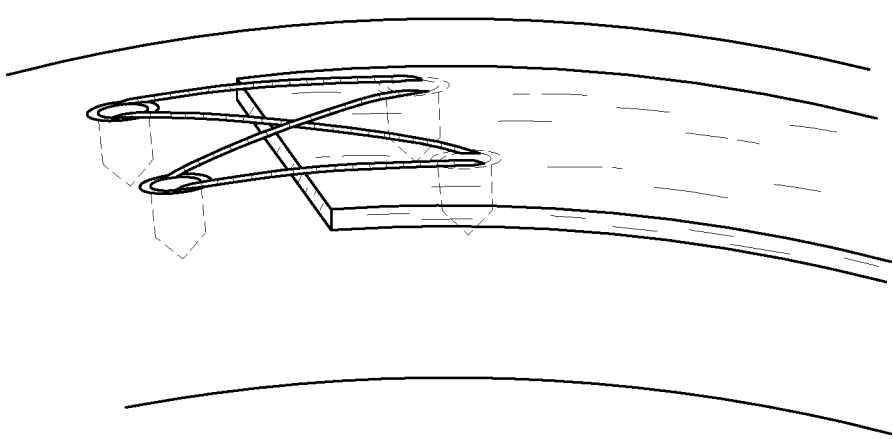

Next, as depicted in FIG. 27D, an anchor 2710, such as described above, is positioned within the surgical site laterally from the soft tissue 2704 using an inserter 2712 The suture 2708 is passed over the soft tissue 2704, tensioned, and secured to the anchor 2710. Any of the anchors described herein permitting suture attachment after anchor insertion may be used for the medial anchor in this embodiment. In one embodiment, the suture 2708 is secured by positioning it behind bendable tabs 2703 prior to complete insertion of the anchor 2710 into the bone. In other embodiments, the suture 2708 is attached to the anchor 2710 using suture passages in the anchor body of the anchor 2710 or attaching it to the spreader or spreader cap. After the anchor 2710 is inserted into the bone, the spreader may be deployed as described above. The result, FIG. 27E, is a length of suture 2708 stretched between the two bone anchors 2702 and 2710 that press the soft tissue 2704 against the bone In other embodiments, suture capture anchors such as described U.S. Patent Application Publication No. 2006-0004364, which is incorporated herein by reference in its entirety, may be used for the lateral anchor 2706.

Multiple anchors, anchors, and sutures may be used to produce geometries such as depicted in FIG. 28A-28D and variations thereof.

Some embodiments include multi-component kits. The kits may include the anchor as described herein as a first component. Other components can include a drill and drill bits for forming a bone hole, sutures, and an inserter tool as described above. In some embodiments, the kit provides the anchor already engaged with the inserter tool ready for insertion. In some embodiments, the anchor is provided with pre-attached sutures, such as sutures attached to the various spreader designs described above.

In some embodiments, a pre-attached delivery handle is provided. In some embodiments, the insertion tool or delivery handle is disposable. In other embodiments, the insertion tool can be sterilized, reloaded and reused.

Although particular inserter devices for inserting and manipulating anchors have been described, it should be understood that other inserter designs may be used for manipulating the parts of anchors described above to insert the anchor into bone and secure tissue to the bone.

It will be appreciated by those of skill in the art that the embodiments of the suture anchors and inserter tools provide a system for easy attachment of a tendon or other tissue to bone. The anchors may be inserted into bone with minimal disruption of surrounding tissue. Only an access route having the diameter of the outer portion of a insertion tool and the anchor body is required. Furthermore, the anchor can be securely attached to the bone without having to insert additional instrumentation into the site or without performing any cumbersome attachment maneuvers such as traditional knot tying.

It will be appreciated that there are numerous stitches, suture threading patterns, and anchor patterns that may be used to secure soft tissue to bone by the methods and devices described herein. These variations as well as variations in the design of the above described anchor devices and inserter devices are within the scope of the present disclosure.

All publications and patent applications cited in this specification are herein incorporated by reference as if each individual publication or patent application were specifically and individually indicated to be incorporated by reference.

Although the foregoing embodiment has been described in some detail by way of illustration and example for purposes of clarity of understanding, it will be readily apparent to those of ordinary skill in the art in light of the teachings of this embodiment that certain changes and modifications may be made thereto without departing from the spirit or scope of the appended claims.

What is claimed is:

1. A method of attaching tissue to bone, the method comprising:
   inserting a bone anchor comprising an anchor body and a spreader in a pre-formed bone hole using an insertion tool, the insertion tool coupled to the spreader, and wherein a suture extends through at least one spreader axial bore positioned through a most distal surface thereof, wherein the most distal surface faces a distal direction, and forms a loop on a most distal end of the spreader;
   proximally advancing the spreader at least partially into an axial bore of the anchor body using the insertion tool, causing the anchor body to expand against bone;
   disengaging the insertion tool from the bone anchor;
   passing the suture which is secured to the spreader through the tissue; and
   fixedly securing the suture on top of the tissue.

2. The method of claim 1, wherein the bone anchor is fully inserted and secured to the bone before the insertion tool is disengaged from the bone anchor.

\* \* \* \* \*